(12) United States Patent  (10) Patent No.: US 8,759,520 B2
East et al.  (45) Date of Patent: Jun. 24, 2014

(54) COMPOUNDS FOR TREATING CANCER

(75) Inventors: Stephen Peter East, Wallingford (GB); Mark Whittaker, Abingdon (GB); Osamu Ichihara, Didcot (GB); Adrian Kotei Kotey, Didcot (GB); Smantha Jayne Bamford, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 62 days.

(21) Appl. No.: 13/132,429

(22) PCT Filed: Dec. 8, 2009

(86) PCT No.: PCT/GB2009/002848
§ 371 (c)(1),
(2), (4) Date: Sep. 12, 2011

(87) PCT Pub. No.: WO2010/067067
PCT Pub. Date: Jun. 17, 2010

(65) Prior Publication Data
US 2011/0312969 A1    Dec. 22, 2011

(30) Foreign Application Priority Data

Dec. 8, 2008  (EP) .................................... 08253914
Aug. 14, 2009  (GB) .................................. 0914322.3

(51) Int. Cl.
C07D 403/00 (2006.01)
C07D 235/04 (2006.01)
C07D 211/06 (2006.01)
C07D 401/00 (2006.01)

(52) U.S. Cl.
USPC ..... 544/366; 544/358; 548/304.7; 548/307.4; 546/197; 546/273.4

(58) Field of Classification Search
USPC ................ 544/366, 358; 548/304.7; 546/197
See application file for complete search history.

(56) References Cited

U.S. PATENT DOCUMENTS 6,238,878 B1 * 5/2001 Jakobsen et al. ................ 435/13
2005/0159427 A1 7/2005 Bruncko et al.

FOREIGN PATENT DOCUMENTS

| WO | 9928313 A1 | 6/1999 |
| WO | 0077246 A2 | 12/2000 |
| WO | 2007084728 A2 | 7/2007 |
| WO | 2008130970 A1 | 10/2008 |

OTHER PUBLICATIONS

International Search Report, Form PCT/ISA/220, for corresponding PCT/GB2009/002848; date of mailing: Jan. 20, 2010.

* cited by examiner

*Primary Examiner* — Shirley V Gembeh
(74) *Attorney, Agent, or Firm* — Michael P. Morris; Alan R. Stempel

(57) ABSTRACT

Compounds of general formula (I): wherein $R^1$, $R^2$, $R^3$, $R^4$, $R^5$, $R^6$, X and Y are as defined herein are inhibitors of Bcl-2 and are useful for treating diseases characterized by abnormal cell growth and/or dysregulated apoptosis.

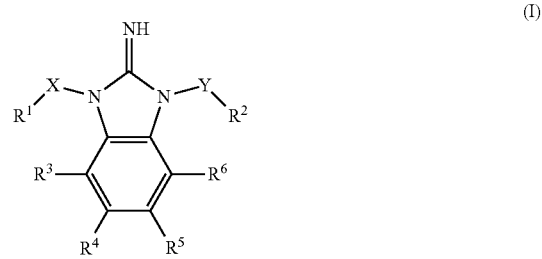

10 Claims, 1 Drawing Sheet

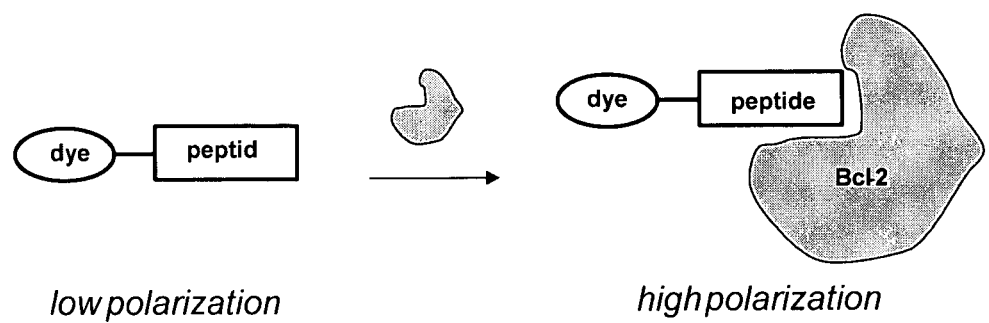

COMPOUNDS FOR TREATING CANCER

The present invention relates to compounds which are inhibitors of pro-survival B-cell lymphoma 2 (Bcl-2) proteins and which are therefore of use in the treatment of cancers, in particular solid tumours and hematopoietic malignancies, for example leukaemia and lymphoma. More particularly, the invention relates to iminobenzimidazole compounds.

The B cell lymphoma 2 (Bcl-2) family of proteins is composed of both pro-apoptotic (pro-death) and anti-apoptotic members, with the anti-apoptotic (pro-survival) family members including Bcl-2, Bcl-xL and Mcl-1. Pro-survival family members such as these bind to and sequester their pro-death counterparts. Cancer cells frequently overexpress the pro-survival Bcl-2 family members to suppress the apoptotic signal and promote survival or confer resistance to chemotherapy. Anti-apoptotic family protein members are also associated with a number of other diseases. Inhibition of pro-survival Bcl-2 family members is therefore an attractive target for therapeutic intervention.

Bcl-2 inhibitors are known in the art and, for example, WO2005/049593, WO2005/049594 US 2005/0159427, US 2006/0128706, US 2006/0258657, US 2007/0015787 and US 2007/0072860 all relate to compounds which are inhibitors of anti-apoptotic proteins of the Bcl-2 family. These compounds comprise an aromatic ring system derivatised with a group —$SO_2$—NH—C(O)—Z. In WO2005/049593, Z is a substituted phenyl or pyridyl group and in WO2005/049594, US 2005/0159427, US 2006/0128706, US 2006/0258657, US 2007/0015787 and US 2007/0072860, Z is a phenyl or heteroaryl which may be fused to another ring.

WO2007/040650 also relates to inhibitors of anti-apoptosis proteins; in this case the compounds comprise a phenyl ring derivatised with a group —$SO_2$—NH—C(O)-phenyl-piperazine-$R^0$, where $R^0$ is a bicyclic group, as well as an $SO_2CF_2X^3$ group, where $X^3$ is halo, and a secondary amine group.

WO2006/127364 relates to similar compounds to those of the above having a phenyl ring derivatised with a group —$SO_2$—NH—C(O)—$Z^1$, in which $Z^1$ is a phenyl or heteroaryl group.

Bruncko et al, *J. Med. Chem.*, (2007), 50, 641-662 relates to compounds which are dual inhibitors of Bcl-2 and Bcl-xL anti-apoptotic proteins.

The present invention relates to anti-apoptosis inhibiting compounds of an alternative structure.

Therefore, in a first aspect of the present invention there is provided a compound of general formula (I):

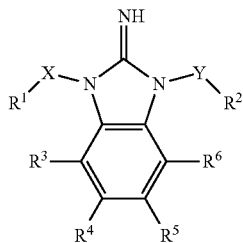

wherein
X is $(CH_2)_m$ optionally substituted with one or more substituents selected from, methyl and ethyl and additionally, when m is greater than 1, from OH and halo;
m is an integer from 1 to 4;

$R^1$ is $R^7$, $OR^7$, $SR^7$, $NHR^7$
$R^7$ is H, aryl or heteroaryl optionally substituted with halo, —$NO_2$, —CN, —$R^8$, —$OR^8$, —C(O)$OR^8$, —C(O)$R^8$, —C(O)N($R^8$)$_2$, —C(O)NH$SO_2R^8$, —$SOR^8$, —$SO_2R^8$, —$SO_2$N($R^8$)$_2$, —N($R^8$)$_2$, —$NR^8$C(O)$R^8$, each $R^8$ is independently H or $C_1$-$C_4$ alkyl;
Y is $(CH_2)_n$
n is an integer from 1 to 6;
$R^2$ is H, N($R^9$)$_2$, C(O)$R^9$, C(O)$OR^9$, C(O)N($R^9$)$_2$, $OR^9$, $SR^9$, $SOR^9$, $SO_2R^9$ or $R^{10}$
each $R^9$ is independently H or $C_1$-$C_6$ alkyl;
$R^{10}$ is carbocyclyl, heterocyclyl, aryl or heteroaryl, any of which may be substituted with one or more substituents chosen from halo, $C_1$-$C_6$ alkyl, —$OR^{11}$, —C(O)$OR^{11}$, —C(O)$R^{11}$, —N($R^{11}$)$_2$, —($C_1$-$C_6$ alkyl)-NH—($C_1$-$C_4$ alkyl)C(O)$NHR^{12}$ and $R^{12}$;
$R^{11}$ is H or $C_1$-$C_6$ alkyl
$R^{12}$ is -carbocyclyl, -heterocyclyl, -aryl, -heteroaryl, —$C_1$-$C_6$ alkyl(carbocyclyl), —$C_1$-$C_6$ alkyl(heterocyclyl), —$C_1$-$C_6$ alkyl(aryl) or —$C_1$-$C_6$ alkyl(heteroaryl group), any of which may optionally be substituted with one or more substituents chosen from halo, CN, $NO_2$, O($C_1$-$C_6$ alkyl), $C_1$-$C_6$ alkyl and $R^{13}$
$R^{13}$ is -carbocyclyl, -heterocyclyl, -aryl, -heteroaryl, —$C_1$-$C_6$ alkyl(carbocyclyl), —$C_1$-$C_6$ alkyl(heterocyclyl), —$C_1$-$C_6$ alkyl(aryl) or —$C_1$-$C_6$ alkyl(heteroaryl), any of which is optionally substituted with one or more substituents chosen from halo and $C_1$-$C_6$ alkyl, -carbocyclyl, -heterocyclyl, -aryl, -heteroaryl, any of which may optionally be substituted with one or more substituents chosen from halo, CN, $NO_2$, O($C_1$-$C_4$ alkyl) and $C_1$-$C_4$ alkyl;
$R^3$, $R^4$, $R^5$ and $R^6$ are each independently selected from hydrogen, halogen, $C_1$-$C_6$ alkyl, —$OR^{14}$, —C(O)N($R^{14}$)$_2$, —S(O)$R^{14}$, —S(O)$_2R^{14}$, —S(O)$_2$N($R^{14}$)$_2$, —N($R^{14}$)$_2$, —$NR^{14}$C(O)$R^{14}$, —C(O)$OR^{14}$, —C(O)$R^{14}$, —$SR^{14}$, $NO_2$ and CN;
$R^{14}$ is hydrogen or $C_1$-$C_6$ alkyl, phenyl or a 5- or 6-membered heteroaryl group, wherein the alkyl, phenyl and heteroaryl groups may optionally be substituted with one or more substituents chosen from halo, $CF_3$, CN, $NO_2$, $OCH_3$, and, for phenyl and heteroaryl groups, $C_1$-$C_4$ alkyl;
provided that:
when $R^1$ is phenyl optionally substituted with halo, trifluoromethyl, trifluoromethoxy or —N($R^8$)$_2$, $R^2$ is not phenyl optionally substituted with halo, trifluoromethyl, trifluoromethoxy or —N($R^{11}$)$_2$;
when X—$R^1$ is methyl, $R^2$ is not a heteroaryl group optionally substituted by one or more substituents chosen from methyl, oxo, phenyl and chlorophenyl;
or a tautomer, enantiomer or pharmaceutically acceptable salt, hydrate, solvate, complex or prodrug thereof for use in the treatment of diseases and conditions mediated by anti-apoptotic proteins of the Bcl-2 family.

In particular, the compounds of general formula (I) and their tautomers, enantiomers, pharmaceutically acceptable salts, hydrates, solvates, complexes and prodrugs thereof are useful for the treatment of diseases characterised by abnormal cell growth and/or dysregulated apoptosis. These include diseases and conditions such as cancer for example, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia , esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

The invention further relates to the use of a compound of general formula (I) in the preparation of an agent for the treatment of one or more of the above-named diseases or conditions.

In addition the invention comprises a method of treating one of the above named diseases or conditions, the method comprising administering to a patient in need of such treatment an effective amount of a compound of general formula (I).

The compound of formula (I) may be used alone or in combination with another agent for use in the treatment of one of the above conditions.

Compounds of similar general formula are known but are not known to be inhibitors of anti-apoptosis proteins.

For example, WO 2002/088094 relates to iminobenzimidazole compounds which are PAR1 thrombin receptor antagonists. The document suggests that the compounds would be useful for inhibiting platelet aggregation and other cellular responses to thrombin.

WO 2003/105779 relates to compounds of the formula:

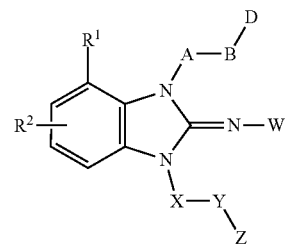

where $R^1$ and $R^2$ can each be a wide variety of substituents. These compounds are said to have analgesic and anaesthetic activity and to be useful for the treatment of conditions including neuropathic pain, epilepsy, convulsions, brain or spinal cord ischaemia, brain or spinal cord trauma or stroke. There is no suggestion that the compounds could be of use in the treatment of proliferative conditions.

Ramström et al, *J. Med. Chem.*, (2004), 47, 2264-2275 relates to iminobenzimidazole compounds which are said to have potential as antibiotics.

WO 2006/074991 discloses iminobenzimidazole compounds of the formula:

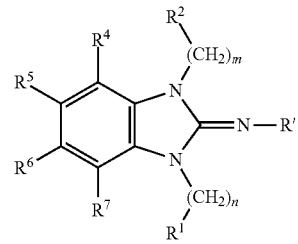

where $R^1$ and $R^2$ are both phenyl groups and which are said to be modulators of small conductance calcium-activated potassium channels. The activities of these compounds are said to include the treatment of cancer.

WO 2007/084728 relates to compounds of the general formula:

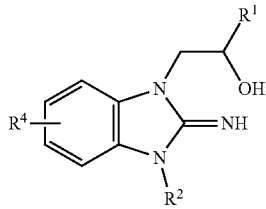

The substituents A, B, D, X, Y, Z, $R^1$ and $R^2$ can be chosen from a large number of groups. However, in all of the compounds exemplified in the document:

i. the group X-Y-Z represents —$CH_2$—C(O)-phenyl, —$CH_2$—C(O)-heterocyclyl or —$CH_2$—C(O)—NR'R";

ii. the group X-Y-Z represents —$CH_2$-heterocyclyl or —$CH_2CH_2$-heterocyclyl and the group A-B-D is methyl; or iii. the group X-Y-Z represents $CH_2$CON(R)-phenyl.

The compounds are said to be of use for treating a number of diseases, including, for example, cancers of the lung, breast, stomach, colon, pancreas, ovaries, prostate, rectum and haematopoietic malignancies such as leukaemia and lymphoma.

WO 00/77246 relates to compounds which are useful as TF antagonists and anti-coagulants and to a method of identifying compounds which are useful in treating TF/FVIIa-related diseases or disorders, for example tumour metastasis.

WO 99/28313 relates to compounds that do not have a thiol moiety and which inhibit farnesyl-protein transferase. The compounds are said to be useful for the treatment of cancer. Hu et al, *J. Pharm. Exp. Ther.*, 328(3), 866-872 (2009) relates to the use of compounds designated BEPP and BECC to induce double stranded RNA-dependent protein kinase-dependent apoptosis, suggesting that the compounds will be of use in the treatment of cancer.

In the present invention, the term "$C_1$-$C_6$ alkyl" relates to a straight or branched fully saturated hydrocarbon chain having from one to six carbon atoms and optionally substituted with one or more halo atoms. Examples include methyl, trifluoromethyl, ethyl, 1,2-dichloroethyl, n-propyl, isopropyl, n-butyl, t-butyl, i-butyl and n-hexyl. The term "$C_1$-$C_4$ alkyl" has a similar meaning except that it relates to alkyl groups having from one to four carbon atoms in the chain.

The term "aryl" refers to a ring system having from 5 to 12 ring carbon atoms and which may comprise a single ring, which is aromatic in character or two or three fused rings, at least one of which has aromatic character. Examples include phenyl and naphthyl. The terms "5- or 6-membered aryl" and "$C_5$-$C_6$ aryl" should be similarly construed except that they refer to a ring which has 5 or 6 ring carbon atoms.

The term "heteroaryl" refers to a ring system having from 5 to 12 ring atoms, wherein at least one ring atom is N, O or S, and which may comprise a single ring, which is aromatic in character or two or three fused rings, at least one of which has aromatic character. Examples of heteroaryl ring systems include pyridine, pyrimidine, pyrazine, pyridazine, furan, thiophene, indole, isoindole, benzofuran, benzimidazole, benzimidazoline, benzodioxyl, benzodioxane, quinoline, isoquinoline, tetrahydroisoquinoline, quinazoline, thiazole, benzthiazole, thiadiazole, oxazole, isoxazole, benzoxazole, indazole and imidazole ring systems. The term "5- or 6-membered heteroaryl" should be similarly construed except that it refers to a ring which has 5 or 6 ring atoms.

The term "carbocyclyl" refers to a non-aromatic ring system having from 3 to 12 ring carbon atoms and up to three rings, which may be fused or bridged. The ring system may contain one or more carbon-carbon double bonds. Examples include cyclopropyl, cyclobutyl, cyclopentyl, cyclohexyl, cyclohexenyl, norbornyl, adamantyl, decahydronaphthyl. The term "$C_5$-$C_6$ carbocyclyl" should be similarly construed except that it refers to a carbocyclic ring with 5 or 6 ring atoms.

The term "heterocyclyl" refers to a non-aromatic ring system having from 5 to 12 ring atoms, at least one of which is N, O or S, and up to three rings, which may be fused or bridged. The ring system may contain one or more carbon-carbon double bonds. Examples include pyrroline, pyrrolidine, tetrahydrofuran, tetrahydropyran, morpholine, piperidine, piperazine, imidazoline, oxazoline, dioxolane, diazepam, decahydroquinoline and decahydroisoquinoline. The term "$C_5$-$C_6$ heterocyclyl" should be similarly construed except that it refers to a heterocyclic ring with 5 or 6 ring atoms.

The term "halo" refers to fluoro, chloro, bromo and iodo.

Appropriate pharmaceutically and veterinarily acceptable salts of the compounds of general formula (I) include basic addition salts such as sodium, potassium, calcium, aluminium, zinc, magnesium and other metal salts as well as choline, diethanolamine, ethanolamine, ethyl diamine and other well known basic addition salts.

Where appropriate, pharmaceutically acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts which are not pharmaceutically or veterinarily acceptable may still be valuable as intermediates.

Prodrugs are any covalently bonded compounds which release the active parent drug according to general formula (I) in vivo. Examples of prodrugs include alkyl esters when the compounds of general formula (I) contain a carboxylic acid functional group.

In particularly suitable compounds of the present invention, independently or in any combination: X is $(CH_2)_m$, where m is 1 to 3 and which, when m is 2 or 3, is optionally substituted with OH; $R^1$ is $R^7$, $OR^7$ or $SR^7$, where $R^7$ is aryl or heteroaryl optionally substituted as set out above but is more usually phenyl optionally substituted with halo, $C(O)OR^8$ or $C(O)NHSO_2R^8$.

In still more suitable compounds, however, $R^1$ is $OR^7$ or $SR^7$, where $R^7$ is phenyl optionally substituted with halo, $C(O)OR^8$ or $C(O)NHSO_2R^8$. Halo substituents will generally be at the phenyl 4-position, with fluoro being the most suitable halo substituent. $C(O)OR^8$ or $C(O)NHSO_2R^8$ will typically be in either the 3- or the 4-position of the phenyl group.

When $R^7$ is phenyl substituted with $C(O)OR^8$, $R^8$ is typically hydrogen, methyl or ethyl and when $R^7$ is phenyl substituted with $C(O)NHSO_2R^8$, $R^8$ is usually methyl or ethyl.

Specific examples of X groups include $CH_2$, $(CH_2)_2$, $(CH_2)_3$ and $CH_2CH(OH)$—$CH_2$.

In one embodiment of the invention, $R^2$ is a group $R^{10}$, where $R^{10}$ is a 5- or 6-membered aryl or heteroaryl group which may optionally be substituted by halo, particularly bromo, or $C(O)OCH_3$. In this embodiment, $R^2$ is suitably phenyl and any halo substituent is suitably in the 4-position, while a $C(O)OCH_3$ substituent may be in the 3-position.

In an alternative embodiment, $R^2$ is a group $R^{10}$, where $R^{10}$ is a 5- or 6-membered aryl or heteroaryl group, substituted by a group $R^{12}$, where $R^{12}$ is as defined above. Suitably in this embodiment, the group $R^{10}$ is a phenyl, pyridyl or thiazole group.

In suitable compounds of this embodiment, $R^{12}$ is a 5- or 6-membered carbocyclic or heterocyclic group optionally substituted by one or more substituents including a group $R^{13}$; or $R^{12}$ is —($C_1$-$C_4$ alkyl)($C_5$-$C_6$ carbocyclyl) or —($C_1$-$C_4$ alkyl)($C_5$-$C_6$ heterocyclyl) optionally substituted with a group $R^{13}$.

Compounds in which $R^{12}$ is a 5- or 6-membered carbocyclic or heterocyclic group substituted by one or more substituents including a group $R^{13}$ are particularly suitable, with compounds in which $R^{12}$ is a 5- or 6-membered carbocyclic or heterocyclic group substituted by a group $R^{13}$ being of particular interest.

In particularly suitable compounds, the aryl or heteroaryl group $R^{10}$ is substituted with a group $R^{12}$ which is selected from 5- or 6-membered carbocyclyl and heterocyclyl groups, with 5- or 6-membered heterocyclyl groups being particularly suitable, especially piperazine groups and in particular 1,4-piperazine. When $R^{12}$ is a 1,4-piperazinyl group, it is preferred that any $R^{13}$ substituent is positioned at the 4-position.

Suitable $R^{13}$ groups include $C_5$-$C_6$ carbocyclyl, $C_5$-$C_6$ aryl, —$CH_2$($C_5$-$C_6$ carbocyclyl) and —$CH_2$($C_5$-$C_6$ aryl), with examples of carbocyclyl and aryl groups including phenyl and cyclohexenyl. These $R^{13}$ groups may have one or more substituents as set out above, and, in particular halo, methyl, ethyl and aryl, which may in turn be substituted with halo.

However, compounds in which $R^{13}$ is optionally substituted —$CH_2$($C_5$-$C_6$ carbocyclyl) and optionally substituted —$CH_2$($C_5$-$C_6$ aryl) have been proved to be more active than their counterparts in which $R^{13}$ is $C_5$-$C_6$ carbocyclyl and $C_5$-$C_6$ aryl, with compounds in which $R^{13}$ is optionally substituted benzyl or cyclohexenylmethyl being preferred.

Suitable substituents for the group $R^{13}$ include one or more halo or methyl groups. However, more active $R^{13}$ groups are substituted with a 5- or 6-membered aryl or heteroaryl group, for example a phenyl group, which may, in turn be substituted with halo, for example chloro, fluoro or bromo. These particularly active $R^{13}$ groups may contain one or more halo or methyl substituents in addition to the $C_5$-$C_6$ aryl or heteroaryl group.

Examples of preferred $R^{13}$ groups include —CH$_2$(biphenyl), for example —CH$_2$(2-biphenyl), optionally substituted with halo and —CH$_2$(2-phenyl-1,2-cyclohexenyl) optionally substituted with one or two methyl groups, for example in the 5-position of the cyclohexenyl ring and/or optionally substituted with one or more halo substituents.

In the compounds of this embodiment, Y is usually CH$_2$.

Particularly suitable compounds for use in the first aspect of the invention include:

1. 1-Benzyl-3-pyridin-2-ylmethyl-1,3-dihydro-benzoimidazol-2-ylideneamine;
2. 1-Benzyl-3-pyridin-3-ylmethyl-1,3-dihydro-benzoimidazol-2-ylideneamine;
3. 1-Benzyl-3-pyridin-4-ylmethyl-1,3-dihydro-benzoimidazol-2-ylideneamine;
4. 1-Benzyl-3-(tetrahydro-pyran-4-ylmethyl)-1,3-dihydro-benzoimidazol-2-ylideneamine;
5. 1-(4-Bromo-benzyl)-3-[3-(4-fluoro-phenoxy)-propyl]-1,3-dihydro-benzoimidazol-2-ylideneamine;
6. 1-(3-Bromo-benzyl)-3-[3-(4-fluoro-phenoxy)-propyl]-1,3-dihydro-benzoimidazol-2-ylideneamine;
7. 1-(4-Bromo-benzyl)-3-(2-phenylsulfanyl-ethyl)-1,3-dihydro-benzoimidazol-2-ylideneamine;
8. {3-[3-(4-Fluoro-phenoxy)-propyl]-2-imino-2,3-dihydro-benzoimidazol-1-yl}-acetic acid ethyl ester;
9. 1-[3-(4-Chloro-phenoxy)-propyl]-3-pyridin-4-ylmethyl-1,3-dihydro-benzoimidazol-2-ylideneamine;
10. 1-(3-Chloro-benzyl)-3-[3-(4-fluoro-phenoxy)-propyl]-1,3-dihydro-benzoimidazol-2-ylideneamine;
11. 1-(3,4-Dichloro-benzyl)-3-[3-(4-fluoro-phenoxy)-propyl]-1,3-dihydro-benzoimidazol-2-ylideneamine;
12. 1-(4-Bromo-benzyl)-3-[3-(4-chloro-phenoxy)-propyl]-1,3-dihydro-benzoimidazol-2-ylideneamine;
13. 1-(4-Bromo-benzyl)-3-(2,3-dihydro-benzo[1,4]dioxin-2-ylmethyl)-1,3-dihydro-benzoimidazol-2-ylideneamine;
14. 1-(4-Bromo-benzyl)-3-[3-(4-nitro-phenoxy)-propyl]-1,3-dihydro-benzoimidazol-2-ylideneamine;
15. 3-{3-[3-(4-Fluoro-phenoxy)-propyl]-2-imino-2,3-dihydro-benzoimidazol-1-ylmethyl}-benzoic acid methyl ester;
16. 1-(4'-Fluoro-biphenyl-4-ylmethyl)-3-[3-(4-fluoro-phenoxy)-propyl]-1,3-dihydro-benzoimidazol-2-ylideneamine;
17. 1-[4-(4-Biphenyl-2-ylmethyl-piperazin-1-yl)-benzyl]-3-methyl-1,3-dihydro-benzoimidazol-2-ylideneamine;
18. 1-Benzyl-3-[4-(4-biphenyl-2-ylmethyl-piperazin-1-yl)-benzyl]-1,3-dihydro-benzoimidazol-2-ylideneamine;
19. 1-{4-[4-(4-Chloro-benzyl)-piperazin-1-yl]-benzyl}-3-[3-(4-fluoro-phenoxy)-propyl]-1,3-dihydro-benzoimidazol-2-ylideneamine;
20. 1-{4-[4-(2-Chloro-benzyl)-piperazin-1-yl]-benzyl}-3-[3-(4-fluoro-phenoxy)-propyl]-1,3-dihydro-benzoimidazol-2-ylideneamine;
21. 1-{4-[4-(3-Chloro-benzyl)-piperazin-1-yl]-benzyl}-3-[3-(4-fluoro-phenoxy)-propyl]-1,3-dihydro-benzoimidazol-2-ylideneamine;
22. 1-[4-(4-Benzyl-piperazin-1-yl)-benzyl]-3-[3-(4-fluoro-phenoxy)-propyl]-1,3-dihydro-benzoimidazol-2-ylideneamine;
23. 1-(4-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
24. 1-{4-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;
25. 1-[4-(4-Biphenyl-2-ylmethyl-piperazin-1-yl)-benzyl]-3-[3-(4-fluoro-phenoxy)-propyl]-1,3-dihydro-benzoimidazol-2-ylideneamine;
26. 1-[3-(4-Biphenyl-2-ylmethyl-piperazin-1-yl)-benzyl]-3-[3-(4-fluoro-phenoxy)-propyl]-1,3-dihydro-benzoimidazol-2-ylideneamine;
27. 1-{3-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;
28. 1-[4-(4-Biphenyl-2-ylmethyl-piperazin-1-yl)-benzyl]-3-(3-phenoxy-propyl)-1,3-dihydro-benzoimidazol-2-ylideneamine;
29. 1-[3-(4-Biphenyl-2-ylmethyl-piperazin-1-yl)-benzyl]-3-(3-phenoxy-propyl)-1,3-dihydro-benzoimidazol-2-ylideneamine;
30. 1-{4-[4-(4'-Chloro-biphenyl-2-ylmethyl)-piperazin-1-yl]-benzyl}-3-(3-phenoxy-propyl)-1,3-dihydro-benzoimidazol-2-ylideneamine;
31. 1-(3-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
32. 1-(4-{4-[2-(4-Chloro-phenyl)-5,5-dimethyl-cyclohex-1-enylmethyl]-piperazin-1-yl}-benzyl)-3-(3-phenoxy-propyl)-1,3-dihydro-benzoimidazol-2-ylideneamine;
33. 1-{4-[4-(4'-Chloro-biphenyl-2-ylmethyl)-piperazin-1-yl]-benzyl}-3-(2-phenylsulfanyl-ethyl)-1,3-dihydro-benzoimidazol-2-ylideneamine;
34. 1-(2-Chloro-thiazol-4-ylmethyl)-3-[3-(4-fluoro-phenoxy)-propyl]-1,3-dihydro-benzoimidazol-2-ylideneamine;
35. 1-[2-(4-Biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine;
36. 1-{2-[4-(4'-Chloro-biphenyl-2-ylmethyl)-piperazin-1-yl]-thiazol-4-ylmethyl}-3-[3-(4-fluoro-phenoxy)-propyl]-1,3-dihydro-benzoimidazol-2-ylideneamine;
37. 1-(2-{4-[2-(4-Chloro-phenyl)-5,5-dimethyl-cyclohex-1-enylmethyl]-piperazin-1-yl}-thiazol-4-ylmethyl)-3-[3-(4-fluoro-phenoxy)-propyl]-1,3-dihydro-benzoimidazol-2-ylideneamine;
38. 1-[2-(4-Biphenyl-2-ylmethyl-piperazin-1-yl)-benzyl]-3-[3-(4-fluoro-phenoxy)-propyl]-1,3-dihydro-benzoimidazol-2-ylideneamine;
39. 1-{4-[4-(4-Chloro-benzyl)-piperazin-1-ylmethyl]-benzyl}-3-[3-(4-fluoro-phenoxy)-propyl]-1,3-dihydro-benzoimidazol-2-ylideneamine;
40. 1-[3-(4-Fluoro-phenoxy)-propyl]-3-[4-(4-phenyl-piperazin-1-ylmethyl)-benzyl]-1,3-dihydro-benzoimidazol-2-ylideneamine;
41. 1-{4-[4-(3-Chloro-phenyl)-piperazin-1-ylmethyl]-benzyl}-3-[3-(4-fluoro-phenoxy)-propyl]-1,3-dihydro-benzoimidazol-2-ylideneamine;
42. 1-{4-[4-(4-Chloro-phenyl)-piperazin-1-ylmethyl]-benzyl}-3-[3-(4-fluoro-phenoxy)-propyl]-1,3-dihydro-benzoimidazol-2-ylideneamine;
43. N-(2-Chloro-phenyl)-2-(4-{3-[3-(4-fluoro-phenoxy)-propyl]-2-imino-2,3-dihydro-benzoimidazol-1-ylmethyl}-benzylamino)-acetamide;
44. 1-{4-[4-(2-Chloro-phenyl)-piperazin-1-ylmethyl]-benzyl}-3-[3-(4-fluoro-phenoxy)-propyl]-1,3-dihydro-benzoimidazol-2-ylideneamine;

45. N-(4-Chloro-phenyl)-2-(4-{3-[3-(4-fluoro-phenoxy)-propyl]-2-imino-2,3-dihydro-benzoimidazol-1-ylmethyl}-benzylamino)-acetamide;
46. 1-[4-(4-Benzyl-piperazin-1-ylmethyl)-benzyl]-3-[3-(4-fluoro-phenoxy)-propyl]-1,3-dihydro-benzoimidazol-2-ylideneamine;
47. 1-{4-[4-(3-Chloro-benzyl)-piperazin-1-ylmethyl]-benzyl}-3-[3-(4-fluoro-phenoxy)-propyl]-1,3-dihydro-benzoimidazol-2-ylideneamine;
48. 1-{4-[4-(2-Chloro-benzyl)-piperazin-1-ylmethyl]-benzyl}-3-[3-(4-fluoro-phenoxy)-propyl]-1,3-dihydro-benzoimidazol-2-ylideneamine;
49. 1-[4-(4-Biphenyl-2-ylmethyl-piperazin-1-ylmethyl)-benzyl]-3-[3-(4-fluoro-phenoxy)-propyl]-1,3-dihydro-benzoimidazol-2-ylideneamine;
50. N-(3-Chloro-phenyl)-2-(4-{3-[3-(4-fluoro-phenoxy)-propyl]-2-imino-2,3-dihydro-benzoimidazol-1-ylmethyl}-benzylamino)-acetamide;
51. 2-(4-{3-[3-(4-Fluoro-phenoxy)-propyl]-2-imino-2,3-dihydro-benzoimidazol-1-ylmethyl}-benzylamino)-N-phenyl-acetamide;
52. 1-(6-Chloro-pyridin-3-ylmethyl)-3-[3-(4-fluoro-phenoxy)-propyl]-1,3-dihydro-benzoimidazol-2-ylideneamine;
53. 1-[6-(4-Benzyl-piperazin-1-yl)-pyridin-3-ylmethyl]-3-[3-(4-fluoro-phenoxy)-propyl]-1,3-dihydro-benzoimidazol-2-ylideneamine;
54. 1-{6-[4-(3-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
55. 1-{6-[4-(4-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
56. 1-[6-(4-Biphenyl-2-ylmethyl-piperazin-1-yl)-pyridin-3-ylmethyl]-3-[3-(4-fluoro-phenoxy)-propyl]-1,3-dihydro-benzoimidazol-2-ylideneamine;
57. 1-16-[4-(2-Chloro-benzyl)-piperazin-1-A-pyridin-3-ylmethyl]-3-[3-(4-fluoro-phenoxy)-propyl]-1,3-dihydro-benzoimidazol-2-ylideneamine;
58. 3-(4-Bromo-benzyl)-1-[3-(4-fluoro-phenoxy)-propyl]-5-methyl-1,3-dihydro-benzoimidazol-2-ylideneamine;
59. 3-(4-Bromo-benzyl)-5-fluoro-1-[3-(4-fluoro-phenoxy)-propyl]-1,3-dihydro-benzoimidazol-2-ylideneamine;
60. 1-(4-Bromo-benzyl)-3-[3-(4-fluoro-phenoxy)-propyl]-5-trifluoromethyl-1,3-dihydro-benzoimidazol-2-ylideneamine;
61. 1-(4-Bromo-benzyl)-5-fluoro-3-[3-(4-fluoro-phenoxy)-propyl]-1,3-dihydro-benzoimidazol-2-ylideneamine;
62. 3-[4-(4-Biphenyl-2-ylmethyl-piperazin-1-yl)-benzyl]-1-[3-(4-fluoro-phenoxy)-propyl]-5-methyl-1,3-dihydro-benzoimidazol-2-ylideneamine;
63. 3-[4-(4-Biphenyl-2-ylmethyl-piperazin-1-yl)-benzyl]-5-fluoro-1-[3-(4-fluoro-phenoxy)-propyl]-1,3-dihydro-benzoimidazol-2-ylideneamine;
64. 3-(4-{4-[2-(4-Chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine;
65. 3-{3-[3-(4-Bromo-benzyl)-2-imino-2,3-dihydro-benzoimidazol-1-yl]-propoxy}-benzoic acid ethyl ester;
66. 4-{3-[3-(4-Bromo-benzyl)-2-imino-2,3-dihydro-benzoimidazol-1-yl]-propoxy}-benzoic acid methyl ester;
67. 4-{3-[3-(3-Bromo-benzyl)-2-imino-2,3-dihydro-benzoimidazol-1-yl]-propoxy}-benzoic acid methyl ester;
68. 3-{3-[3-(3-Bromo-benzyl)-2-imino-2,3-dihydro-benzoimidazol-1-yl]-propoxy}-benzoic acid ethyl ester;
69. 3-(3-{3-[4-(4-Biphenyl-2-ylmethyl-piperazin-1-yl)-benzyl]-2-imino-2,3-dihydro-benzoimidazol-1-yl}-propoxy)-benzoic acid ethyl ester;
70. 3-(3-{3-[4-(4-Biphenyl-2-ylmethyl-piperazin-1-yl)-benzyl]-2-imino-2,3-dihydro-benzoimidazol-1-yl}-propoxy)-benzoic acid;
71. 3-[3-(3-Benzyl-2-imino-2,3-dihydro-benzoimidazol-1-yl)-propoxy]-benzoic acid ethyl ester;
72. 3-{3-[3-(4-Fluoro-phenoxy)-propyl]-2-imino-2,3-dihydro-benzo imidazol-1-ylmethyl}-benzoic acid;
73. 3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid ethyl ester;
74. 3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid;
75. 3-{3-[3-(3-{4-[2-(4-Chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid;
76. 1-[3-(3-Bromo-benzyl)-2-imino-2,3-dihydro-benzoimidazol-1-yl]-3-(4-fluoro-phenoxy)-propan-2-ol;
77. 1-[3-(4-Bromo-benzyl)-2-imino-2,3-dihydro-benzoimidazol-1-yl]-3-(4-fluoro-phenoxy)-propan-2-ol;
78. 1-(3-Benzyl-2-imino-2,3-dihydro-benzoimidazol-1-yl)-3-phenoxy-propan-2-ol;
79. 1-(3-Benzyl-2-imino-2,3-dihydro-benzoimidazol-1-yl)-3-o-tolyloxy-propan-2-ol;
80. 1-(3-Benzyl-2-imino-2,3-dihydro-benzoimidazol-1-yl)-3-(4-chloro-phenoxy)-propan-2-ol;
81. 1-(3-Benzyl-2-imino-2,3-dihydro-benzoimidazol-1-yl)-3-(4-nitro-phenoxy)-propan-2-ol;
82. 1-{3-[3-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
83. 1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
84. 3-{3-[3-(3-Bromo-benzyl)-2-imino-2,3-dihydro-benzoimidazol-1-yl]-propoxy}-benzoic acid;
85. 3-{3-[3-(4-Bromo-benzyl)-2-imino-2,3-dihydro-benzoimidazol-1-yl]-propoxy}-benzoic acid;
86. N-(3-{3-[3-(3-Bromo-benzyl)-2-imino-2,3-dihydro-benzoimidazol-1-yl]-propoxy}-benzoyl)-methanesulfonamide;
87. 1-Benzyl-3-[3-(4-bromo-phenoxy)-propyl]-1,3-dihydro-benzoimidazol-2-ylideneamine;
88. 1-(3-Benzyl-2-imino-2,3-dihydro-benzoimidazol-1-yl)-3-(4-methoxy-phenoxy)-propan-2-ol;
89. 1-(3-Benzyl-2-imino-2,3-dihydro-benzoimidazol-1-yl)-3-(2-methoxy-phenoxy)-propan-2-ol;
90. 1-(3-Benzyl-2-imino-2,3-dihydro-benzoimidazol-1-yl)-3,3-dimethyl-butan-2-one;
91. 2-(3-Benzyl-2-imino-2,3-dihydro-benzoimidazol-1-yl)-1-furan-2-yl-ethanol;
92. 2-(3-Benzyl-2-imino-2,3-dihydro-benzoimidazol-1-yl)-1-phenyl-ethanol;
93. 1-(3-Butyl-2-imino-2,3-dihydro-benzoimidazol-1-yl)-3-(2-methoxy-phenoxy)-propan-2-ol;
94. 1-(2-Methyl-benzyl)-3-(3-phenoxy-propyl)-1,3-dihydro-benzoimidazol-2-ylideneamine;
95. 1-Benzyl-3-[2-(2-methoxy-phenoxy)-ethyl]-1,3-dihydro-benzoimidazol-2-ylideneamine;
96. 1-(2-Fluoro-benzyl)-3-(3-phenoxy-propyl)-1,3-dihydro-benzoimidazol-2-ylideneamine
97. 1-Benzyl-3-[3-(4-fluoro-phenoxy)-propyl]-1,3-dihydro-benzoimidazol-2-ylideneamine;

98. 1-(2-Imino-3-pentyl-2,3-dihydro-benzoimidazol-1-yl)-3-(2-methoxy-phenoxy)-propan-2-ol;
99. 1-(3-Benzyl-2-imino-2,3-dihydro-benzoimidazol-1-yl)-3-p-tolyloxy-propan-2-ol;
100. 1-[2-Imino-3-(4-methyl-benzyl)-2,3-dihydro-benzoimidazol-1-yl]-3-phenoxy-propan-2-ol;
101. 1-(3-Hexyl-2-imino-2,3-dihydro-benzoimidazol-1-yl)-3-(2-methoxy-phenoxy)-propan-2-ol;
102. 1-[3-(2-Chloro-benzyl)-2-imino-2,3-dihydro-benzoimidazol-1-yl]-3-phenoxy-propan-2-ol;
103. 1-[3-(4-Chloro-benzyl)-2-imino-2,3-dihydro-benzoimidazol-1-yl]-3-phenoxy-propan-2-ol;
104. 1-[3-(4-tert-Butyl-benzyl)-2-imino-2,3-dihydro-benzoimidazol-1-yl]-3-phenoxy-propan-2-ol;
105. 1-[3-(4-Chloro-benzyl)-2-imino-2,3-dihydro-benzoimidazol-1-yl]-3-(4-chloro-phenoxy)-propan-2-ol ;
106. 1-(3-Benzyl-2-imino-2,3-dihydro-benzoimidazol-1-yl)-3-(2,4-dichloro-phenoxy)-propan-2-ol;

or a tautomer, enantiomer or pharmaceutically acceptable salt, hydrate, solvate, complex or prodrug thereof.

Some of the compounds of general formula (I) are new and these include compounds of general formula (I) in which $R^2$ is a group $R^{10}$, where $R^{10}$ is a 5- or 6-membered aryl or heteroaryl group substituted by a group $R^{12}$, where $R^{12}$ is as defined above and is, in turn, substituted by a group $R^{13}$ as defined above.

In suitable novel compounds, $R^{12}$ is a 5- or 6-membered carbocyclic or heterocyclic group, —($C_1$-$C_4$ alkyl)($C_5$-$C_6$ carbocyclyl) or —($C_1$-$C_4$ alkyl)($C_5$-$C_6$ heterocyclyl) which, in turn is substituted by a group $R^{13}$ as defined above.

In especially suitable compounds, the aryl or heteroaryl group $R^{10}$ is substituted with a group $R^{12}$ which is selected from 5- or 6-membered carbocyclyl and heterocyclyl groups, with 5- or 6-membered heterocyclyl groups being particularly suitable, especially piperazine groups and in particular 1,4-piperazine. When $R^{12}$ is a 1,4-piperazinyl group, it is preferred that the $R^{13}$ substituent is positioned at the 4-position.

Suitable $R^{13}$ groups include $C_5$-$C_6$ carbocyclyl, $C_5$-$C_6$ aryl, —$CH_2$($C_5$-$C_6$ carbocyclyl) and —$CH_2$($C_5$-$C_6$ aryl), with examples of carbocyclyl and aryl groups including phenyl and cyclohexenyl. These $R^{13}$ groups may have one or more substituents as set out above, and, in particular halo, methyl, ethyl and aryl, which may in turn be substituted with halo.

However, compounds in which $R^{13}$ is optionally substituted —$CH_2$($C_5$-$C_6$ carbocyclyl) and optionally substituted —$CH_2$($C_5$-$C_6$ aryl) have been proved to be more active than their counterparts in which $R^{13}$ is $C_5$-$C_6$ carbocyclyl and $C_5$-$C_6$ aryl, with compounds in which $R^{13}$ is optionally substituted benzyl or cyclohexenylmethyl being preferred.

Suitable substituents for the group $R^{13}$ include one or more halo or methyl groups. However, more active $R^{13}$ groups are substituted with a 5- or 6-membered aryl or heteroaryl group, for example a phenyl group, which may, in turn be substituted with halo, for example chloro, fluoro or bromo. These particularly active $R^{13}$ groups may contain one or more halo or methyl substituents in addition to the $C_5$-$C_6$ aryl or heteroaryl group.

Examples of preferred $R^{13}$ groups include —$CH_2$(biphenyl), for example —$CH_2$(2-biphenyl), optionally substituted with halo and —$CH_2$(2-phenyl-1,2-cyclohexenyl) optionally substituted with one or two methyl groups, for example in the 5-position of the cyclohexenyl ring and optionally substituted with one or more halo substituents.

Suitably, in these compounds, as with the compounds of the first aspect of the invention, independently or in any combination:

X is $(CH_2)_m$, where m is 1 to 3 and which, when m is 2 or 3, is optionally substituted with OH;
$R^1$ is $OR^7$ or $SR^7$, where $R^7$ is phenyl optionally substituted with halo, $C(O)OR^8$.

In addition to the novel compounds of the second aspect of the invention, some of the other compounds used in the first aspect of the invention are also new. Novel compounds of the present invention include:

1. 1-Benzyl-3-pyridin-2-ylmethyl-1,3-dihydro-benzoimidazol-2-ylideneamine;
2. 1-Benzyl-3-pyridin-3-ylmethyl-1,3-dihydro-benzoimidazol-2-ylideneamine;
3. 1-Benzyl-3-pyridin-4-ylmethyl-1,3-dihydro-benzoimidazol-2-ylideneamine;
4. 1-Benzyl-3-(tetrahydro-pyran-4-ylmethyl)-1,3-dihydro-benzoimidazol-2-ylideneamine;
5. 1-(4-Bromo-benzyl)-3-[3-(4-fluoro-phenoxy)-propyl]-1,3-dihydro-benzoimidazol-2-ylideneamine;
6. 1-(3-Bromo-benzyl)-3-[3-(4-fluoro-phenoxy)-propyl]-1,3-dihydro-benzoimidazol-2-ylideneamine;
7. 1-(4-Bromo-benzyl)-3-(2-phenylsulfanyl-ethyl)-1,3-dihydro-benzoimidazol-2-ylideneamine;
8. {3-[3-(4-Fluoro-phenoxy)-propyl]-2-imino-2,3-dihydro-benzoimidazol-1-yl}-acetic acid ethyl ester;
9. 1-[3-(4-Chloro-phenoxy)-propyl]-3-pyridin-4-ylmethyl-1,3-dihydro-benzoimidazol-2-ylideneamine;
10. 1-(3-Chloro-benzyl)-3-[3-(4-fluoro-phenoxy)-propyl]-1,3-dihydro-benzoimidazol-2-ylideneamine;
11. 1-(3,4-Dichloro-benzyl)-3-[3-(4-fluoro-phenoxy)-propyl]-1,3-dihydro-benzoimidazol-2-ylideneamine;
12. 1-(4-Bromo-benzyl)-3-[3-(4-chloro-phenoxy)-propyl]-1,3-dihydro-benzoimidazol-2-ylideneamine;
13. 1-(4-Bromo-benzyl)-3-(2,3-dihydro-benzo[1,4]dioxin-2-ylmethyl)-1,3-dihydro-benzo imidazol-2-ylideneamine;
14. 1-(4-Bromo-benzyl)-3-[3-(4-nitro-phenoxy)-propyl]-1,3-dihydro-benzoimidazol-2-ylideneamine;
15. 3-{3-[3-(4-Fluoro-phenoxy)-propyl]-2-imino-2,3-dihydro-benzo imidazol-1-ylmethyl}-benzoic acid methyl ester;
16. 1-(4'-Fluoro-biphenyl-4-ylmethyl)-3-[3-(4-fluoro-phenoxy)-propyl]-1,3-dihydro-benzoimidazol-2-ylideneamine;
17. 1-[4-(4-Biphenyl-2-ylmethyl-piperazin-1-yl)-benzyl]-3-methyl-1,3-dihydro-benzoimidazol-2-ylideneamine;
18. 1-Benzyl-3-[4-(4-biphenyl-2-ylmethyl-piperazin-1-yl)-benzyl]-1,3-dihydro-benzoimidazol-2-ylideneamine;
19. 1-{4-[4-(4-Chloro-benzyl)-piperazin-1-yl]-benzyl}-3-[3-(4-fluoro-phenoxy)-propyl]-1,3-dihydro-benzoimidazol-2-ylideneamine;
20. 1-{4-[4-(2-Chloro-benzyl)-piperazin-1-yl]-benzyl}-3-[3-(4-fluoro-phenoxy)-propyl]-1,3-dihydro-benzoimidazol-2-ylideneamine;
21. 1-{4-[4-(3-Chloro-benzyl)-piperazin-1-yl]-benzyl}-3-[3-(4-fluoro-phenoxy)-propyl]-1,3-dihydro-benzoimidazol-2-ylideneamine;
22. 1-[4-(4-Benzyl-piperazin-1-yl)-benzyl]-3-[3-(4-fluoro-phenoxy)-propyl]-1,3-dihydro-benzoimidazol-2-ylideneamine;
23. 1-(4-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
24. 1-{4-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;

25. 1-[4-(4-Biphenyl-2-ylmethyl-piperazin-1-yl)-benzyl]-3-[3-(4-fluoro-phenoxy)-propyl]-1,3-dihydro-benzoimidazol-2-ylideneamine;
26. 1-[3-(4-Biphenyl-2-ylmethyl-piperazin-1-yl)-benzyl]-3-[3-(4-fluoro-phenoxy)-propyl]-1,3-dihydro-benzoimidazol-2-ylideneamine;
27. 1-{3-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;
28. 1-[4-(4-Biphenyl-2-ylmethyl-piperazin-1-yl)-benzyl]-3-(3-phenoxy-propyl)-1,3-dihydro-benzoimidazol-2-ylideneamine;
29. 1-[3-(4-Biphenyl-2-ylmethyl-piperazin-1-yl)-benzyl]-3-(3-phenoxy-propyl)-1,3-dihydro-benzoimidazol-2-ylideneamine;
30. 1-{4-[4-(4'-Chloro-biphenyl-2-ylmethyl)-piperazin-1-yl]-benzyl}-3-(3-phenoxy-propyl)-1,3-dihydro-benzoimidazol-2-ylideneamine;
31. 1-(3-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
32. 1-(4-{4-[2-(4-Chloro-phenyl)-5,5-dimethyl-cyclohex-1-enylmethyl]-piperazin-1-yl}-benzyl)-3-(3-phenoxy-propyl)-1,3-dihydro-benzoimidazol-2-ylideneamine;
33. 1-{4-[4-(4'-Chloro-biphenyl-2-ylmethyl)-piperazin-1-yl]-benzyl}-3-(2-phenylsulfanyl-ethyl)-1,3-dihydro-benzoimidazol-2-ylideneamine;
34. 1-(2-Chloro-thiazol-4-ylmethyl)-3-[3-(4-fluoro-phenoxy)-propyl]-1,3-dihydro-benzoimidazol-2-ylideneamine;
35. 1-[2-(4-Biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine;
36. 1-{2-[4-(4'-Chloro-biphenyl-2-ylmethyl)-piperazin-1-yl]-thiazol-4-ylmethyl}-3-[3-(4-fluoro-phenoxy)-propyl]-1,3-dihydro-benzoimidazol-2-ylideneamine;
37. 1-(2-{4-[2-(4-Chloro-phenyl)-5,5-dimethyl-cyclohex-1-enylmethyl]-piperazin-1-yl}-thiazol-4-ylmethyl)-3-[3-(4-fluoro-phenoxy)-propyl]-1,3-dihydro-benzoimidazol-2-ylideneamine;
38. 1-[2-(4-Biphenyl-2-ylmethyl-piperazin-1-yl)-benzyl]-3-[3-(4-fluoro-phenoxy)-propyl]-1,3-dihydro-benzoimidazol-2-ylideneamine;
39. 1-{4-[4-(4-Chloro-benzyl)-piperazin-1-ylmethyl]-benzyl}-3-[3-(4-fluoro-phenoxy)-propyl]-1,3-dihydro-benzoimidazol-2-ylideneamine;
40. 1-[3-(4-Fluoro-phenoxy)-propyl]-3-[4-(4-phenyl-piperazin-1-ylmethyl)-benzyl]-1,3-dihydro-benzoimidazol-2-ylideneamine;
41. 1-{4-[4-(3-Chloro-phenyl)-piperazin-1-ylmethyl]-benzyl}-3-[3-(4-fluoro-phenoxy)-propyl]-1,3-dihydro-benzoimidazol-2-ylideneamine;
42. 1-{4-[4-(4-Chloro-phenyl)-piperazin-1-ylmethyl]-benzyl}-3-[3-(4-fluoro-phenoxy)-propyl]-1,3-dihydro-benzoimidazol-2-ylideneamine;
43. N-(2-Chloro-phenyl)-2-(4-{3-[3-(4-fluoro-phenoxy)-propyl]-2-imino-2,3-dihydro-benzoimidazol-1-ylmethyl}-benzylamino)-acetamide;
44. 1-{4-[4-(2-Chloro-phenyl)-piperazin-1-ylmethyl]-benzyl}-3-[3-(4-fluoro-phenoxy)-propyl]-1,3-dihydro-benzoimidazol-2-ylideneamine;
45. N-(4-Chloro-phenyl)-2-(4-{3-[3-(4-fluoro-phenoxy)-propyl]-2-imino-2,3-dihydro-benzoimidazol-1-ylmethyl}-benzylamino)-acetamide;
46. 1-[4-(4-Benzyl-piperazin-1-ylmethyl)-benzyl]-3-[3-(4-fluoro-phenoxy)-propyl]-1,3-dihydro-benzoimidazol-2-ylideneamine;
47. 1-{4-[4-(3-Chloro-benzyl)-piperazin-1-ylmethyl]-benzyl}-3-[3-(4-fluoro-phenoxy)-propyl]-1,3-dihydro-benzoimidazol-2-ylideneamine;
48. 1-{4-[4-(2-Chloro-benzyl)-piperazin-1-ylmethyl]-benzyl}-3-[3-(4-fluoro-phenoxy)-propyl]-1,3-dihydro-benzoimidazol-2-ylideneamine;
49. 1-[4-(4-Biphenyl-2-ylmethyl-piperazin-1-ylmethyl)-benzyl]-3-[3-(4-fluoro-phenoxy)-propyl]-1,3-dihydro-benzoimidazol-2-ylideneamine;
50. N-(3-Chloro-phenyl)-2-(4-{3-[3-(4-fluoro-phenoxy)-propyl]-2-imino-2,3-dihydro-benzoimidazol-1-ylmethyl}-benzylamino)-acetamide;
51. 2-(4-{3-[3-(4-Fluoro-phenoxy)-propyl]-2-imino-2,3-dihydro-benzoimidazol-1-ylmethyl}-benzylamino)-N-phenyl-acetamide;
52. 1-(6-Chloro-pyridin-3-ylmethyl)-3-[3-(4-fluoro-phenoxy)-propyl]-1,3-dihydro-benzoimidazol-2-ylideneamine;
53. 1-[6-(4-Benzyl-piperazin-1-yl)-pyridin-3-ylmethyl]-3-[3-(4-fluoro-phenoxy)-propyl]-1,3-dihydro-benzoimidazol-2-ylideneamine;
54. 1-{6-[4-(3-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
55. 1-{6-[4-(4-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
56. 1-[6-(4-Biphenyl-2-ylmethyl-piperazin-1-yl)-pyridin-3-ylmethyl]-3-[3-(4-fluoro-phenoxy)-propyl]-1,3-dihydro-benzoimidazol-2-ylideneamine;
57. 1-{6-[4-(2-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
58. 3-(4-Bromo-benzyl)-1-[3-(4-fluoro-phenoxy)-propyl]-5-methyl-1,3-dihydro-benzoimidazol-2-ylideneamine;
59. 3-(4-Bromo-benzyl)-5-fluoro-1-[3-(4-fluoro-phenoxy)-propyl]-1,3-dihydro-benzoimidazol-2-ylideneamine;
60. 1-(4-Bromo-benzyl)-3-[3-(4-fluoro-phenoxy)-propyl]-5-trifluoromethyl-1,3-dihydro-benzoimidazol-2-ylideneamine;
61. 1-(4-Bromo-benzyl)-5-fluoro-3-[3-(4-fluoro-phenoxy)-propyl]-1,3-dihydro-benzoimidazol-2-ylideneamine;
62. 3-[4-(4-Biphenyl-2-ylmethyl-piperazin-1-yl)-benzyl]-1-[3-(4-fluoro-phenoxy)-propyl]-5-methyl-1,3-dihydro-benzoimidazol-2-ylideneamine;
63. 3-[4-(4-Biphenyl-2-ylmethyl-piperazin-1-yl)-benzyl]-5-fluoro-1-[3-(4-fluoro-phenoxy)-propyl]-1,3-dihydro-benzoimidazol-2-ylideneamine;
64. 3-(4-{4-[2-(4-Chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine;
65. 3-{3-[3-(4-Bromo-benzyl)-2-imino-2,3-dihydro-benzoimidazol-1-yl]-propoxy}-benzoic acid ethyl ester;
66. 4-{3-[3-(4-Bromo-benzyl)-2-imino-2,3-dihydro-benzoimidazol-1-yl]-propoxy}-benzoic acid methyl ester;
67. 4-{3-[3-(3-Bromo-benzyl)-2-imino-2,3-dihydro-benzoimidazol-1-yl]-propoxy}-benzoic acid methyl ester;
68. 3-{3-[3-(3-Bromo-benzyl)-2-imino-2,3-dihydro-benzoimidazol-1-yl]-propoxy}-benzoic acid ethyl ester;
69. 3-(3-{3-[4-(4-Biphenyl-2-ylmethyl-piperazin-1-yl)-benzyl]-2-imino-2,3-dihydro-benzoimidazol-1-yl}-propoxy)-benzoic acid ethyl ester;
70. 3-(3-{3-[4-(4-Biphenyl-2-ylmethyl-piperazin-1-yl)-benzyl]-2-imino-2,3-dihydro-benzoimidazol-1-yl}-propoxy)-benzoic acid;

71. 3-[3-(3-Benzyl-2-imino-2,3-dihydro-benzoimidazol-1-yl)-propoxy]-benzoic acid ethyl ester;
72. 3-{3-[3-(4-Fluoro-phenoxy)-propyl]-2-imino-2,3-dihydro-benzoimidazol-1-ylmethyl}-benzoic acid;
73. 3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid ethyl ester;
74. 3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid;
75. 3-{3-[3-(3-{4-[2-(4-Chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid;
76. 1-[3-(3-Bromo-benzyl)-2-imino-2,3-dihydro-benzoimidazol-1-yl]-3-(4-fluoro-phenoxy)-propan-2-ol;
77. 1-[3-(4-Bromo-benzyl)-2-imino-2,3-dihydro-benzoimidazol-1-yl]-3-(4-fluoro-phenoxy)-propan-2-ol;
81. 1-(3-Benzyl-2-imino-2,3-dihydro-benzoimidazol-1-yl)-3-(4-nitro-phenoxy)-propan-2-ol;
82. 1-{3-[3-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
83. 1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
84. 3-{3-[3-(3-Bromo-benzyl)-2-imino-2,3-dihydro-benzoimidazol-1-yl]-propoxy}-benzoic acid;
85. 3-{3-[3-(4-Bromo-benzyl)-2-imino-2,3-dihydro-benzoimidazol-1-yl]-propoxy}-benzoic acid;
86. N-(3-{3-[3-(3-Bromo-benzyl)-2-imino-2,3-dihydro-benzoimidazol-1-yl]-propoxy}-benzoyl)-methanesulfonamide;

or a tautomer, enantiomer or pharmaceutically acceptable salt, hydrate, solvate, complex or prodrug thereof.

Of these, Compound Nos 5, 15, 18, 20-33, 35-38, 46-47, 56, 62, 64, 69-70, 73-75, 77, 82-83 and 86 are particularly useful in the present invention, with compounds Nos 5, 15, 18, 20-33, 35-38, 46-47, 56, 62, 64, 69-70, 73-75, 77, 82-83 and 86 being preferred.

A further group of useful compounds includes Compound Nos 18-33, 35-42, 44, 46-49, 53-57, 62-64, 69, 70, 73-75, 82 and 83, with Compounds Nos 18, 23-33, 35-38, 49, 56, 62-64, 69, 70, 73-75, 82, 83 being particularly suitable.

Compounds of general formula (I) in which $R^2$ is $N(R^9)_2$, $C(O)R^9$, $C(O)OR^9$, $C(O)N(R^9)_2$, $OR^9$, $SR^9$, $SOR^9$, $SO_2R^9$ or a group $R^{10}$ and $R^{10}$ is carbocyclyl, heterocyclyl, aryl or heteroaryl, any of which may be substituted with one or more substituents chosen from halo, $C_1$-$C_6$ alkyl, —$OR^{11}$, —$C(O)OR^{11}$, —$C(O)R^{11}$ and —($C_1$-$C_6$ alkyl)-NH—($C_1$-$C_4$ alkyl)C(O)NHR^{12}$ may be prepared from compounds of general formula (II):

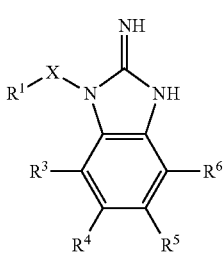

(II)

wherein $R^1$, X, $R^3$, $R^4$, $R^5$ and $R^6$ are as defined in general formula (I) by reaction with a compound of general formula (III):

(III)

wherein $R^{10}$ is carbocyclyl, heterocyclyl, aryl or heteroaryl, any of which may be substituted with one or more substituents chosen from halo, $C_1$-$C_6$ alkyl, —$OR^{11}$, —$C(O)OR^{11}$, —$C(O)R^{11}$ and —($C_1$-$C_6$ alkyl)-NH—($C_1$-$C_4$ alkyl)C(O)NHR^{12}$;
Y is as defined above for general formula (I); and
$L^1$ is a leaving group, for example halo and particularly bromo.

Compounds of general formula (III) are known and are readily available or can be synthesised by known methods.

The reaction may be carried out in a polar solvent such as 2-butanone and at elevated temperature, for example between 50° C. and 100° C.

Some compounds of general formula (II) are also known and are readily available or can be synthesised by known methods. These include compounds of general formula (II) in which X is $CH_2$ and $R^1$ is H or phenyl.

Other compounds of general formula (II) may be synthesised from compounds of general formula (IV)

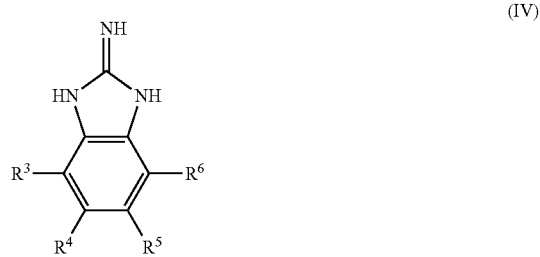

(IV)

wherein $R^3$, $R^4$, $R^5$ and $R^6$ are as defined in general formula (I);
by reaction with a compound of general formula (V):

(V)

wherein $R^1$ and X are as defined in general formula (I) and $L^2$ is a leaving group, for example a halo group such as bromo.

The reaction may be carried out in a polar organic solvent such as ethanol and in the presence of a base such a potassium hydroxide.

Compounds of general formulae (IV) and (V) are known and are readily available or can be synthesised by known methods.

Compounds of general formula (I) may also be synthesised from compounds of general formula (VI):

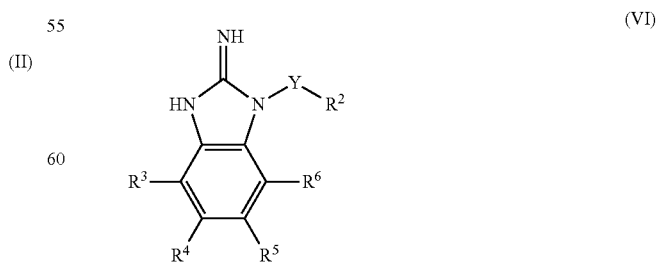

(VI)

wherein $R^2$, Y, $R^3$, $R^4$, $R^5$ and $R^6$ are as defined in general formula (I) by reaction with a compound of general formula (V) as defined above. The reaction typically takes place in an organic solvent such as 2-butanone.

Alternatively, for a compound of general formula (I) in which X is substituted with OH, and m is 3 or more, the compound of general formula (VI) may be reacted with a compound of general formula (VII):

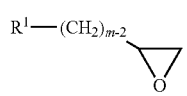
(VII)

wherein $R^1$ and m are as defined for general formula (I).

The reaction is typically carried out in a polar organic solvent such as ethanol.

These methods are particularly useful when $R^2$ is a carbocyclyl, heterocyclyl, aryl or heteroaryl group $R^{10}$ optionally substituted with one or more substituents chosen from halo, $C_1$-$C_6$ alkyl, $-OR^{11}$, $-C(O)OR^{11}$, $-C(O)R^{11}$ and $-(C_1$-$C_6$ alkyl)-NH—$(C_1$-$C_4$ alkyl)C(O)NHR$^{12}R^{10}$.

Compounds of general formulae (VII) are known and are readily available or can be prepared by known methods.

Some compounds of general formula (VI) are also readily available or may be prepared by known methods. In other cases, compounds of general formula (VI) may be prepared from compounds of general formula (IV) as defined above by reaction with compounds of general formula (III) as defined above, typically in a polar organic solvent such as ethanol and in the presence of a base such as potassium hydroxide Alternatively, compounds of general formula (VI) may be prepared by the reaction of a compound of general formula (VIII)

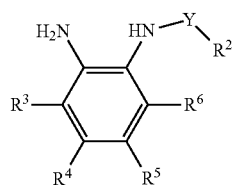
(VIII)

wherein $R^2$, Y, $R^3$, $R^4$, $R^5$ and $R^6$ are as defined in general formula (I) by reaction with cyanogen bromide in a polar solvent such as ethanol.

Compounds of general formula (VIII) may be prepared by reduction of a compound of general formula (IX):

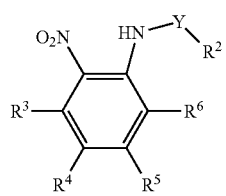
(IX)

wherein $R^2$, Y, $R^3$, $R^4$, $R^5$ and $R^6$ are as defined in general formula (I) using any suitable reducing agent, for example iron and ammonium chloride in an aqueous solvent, for example a mixture of t-butanol and water.

A compound of general formula (IX) may be prepared from a compound of general formula (X)

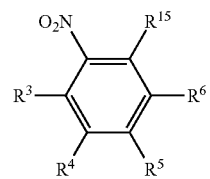
(X)

wherein $R^2$, Y, $R^3$, $R^4$, $R^5$ and $R^6$ are as defined in general formula (I) and $R^{15}$ is halo, especially fluoro; by reaction with a compound of general formula (XI):

(XI)

wherein $R^2$ and Y are as defined for general formula (I), the reaction may be conducted in a polar organic solvent such as ethanol and preferably under an inert atmosphere such as nitrogen at the reflux temperature of the chosen solvent.

In some cases, during the synthesis of compounds of general formula (I), protection of the imine group is advantageous, for example by conversion of the H to BOC. Therefore, compounds of general formula (I) may also be prepared from compounds of general formula (XII):

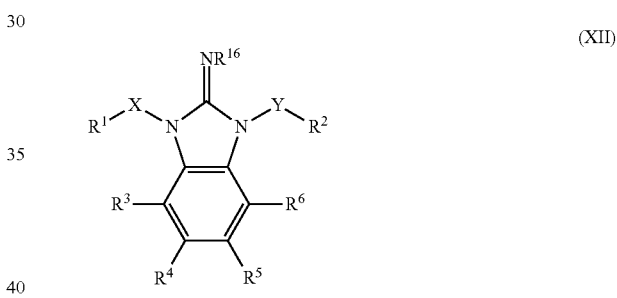
(XII)

where $R^1$, X, $R^2$, Y, $R^3$, $R^4$, $R^5$ and $R^6$ are as defined for general formula (I) and $R^{16}$ is a protecting group such as BOC.

Compounds of general formula (I) may be converted to other compounds of general formula (I). For example, compounds of general formula (Ia):

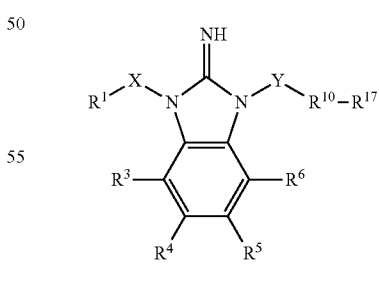

in which $R^1$, X, Y, $R^3$, $R^4$, $R^5$ and $R^6$ are as defined in general formula (I) and $R^2$ is a group $R^{10}$ wherein $R^{10}$ is carbocyclyl, heterocyclyl, aryl or heteroaryl, substituted by at least one halo substituent $R^{17}$ as shown;

may be converted to compounds of general formula (Ib)

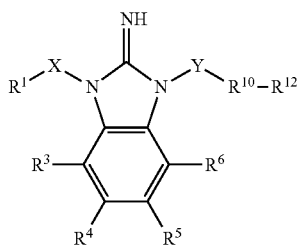

in which $R^1$, X, Y, $R^3$, $R^4$, $R^5$ and $R^6$ are as defined in general formula (I) and $R^2$ is a group $R^{10}$ wherein $R^{10}$ is carbocyclyl, heterocyclyl, aryl or heteroaryl, in which the bromo substituent of general formula (Ia) is replaced with a substituent $R^{12}$ as defined in general formula (I).

$R^{17}$ is usually bromo and the conversion may be achieved by reaction of the compound of general formula (Ia) with a compound of general formula (XII):

$$R^{12}-H \quad \quad \quad (XII)$$

wherein $R^{12}$ is as defined for general formula (I), but especially a heterocyclyl group such as piperazine.

The reaction conditions may vary depending upon the $R^1$, $R^2$, X and Y groups in the starting compound of general formula (Ia) and the $R^{12}$ group in the compound of general formula (XII). Several examples of this type of reaction are given in the Examples section below, in particular Examples 2-6, 8-11, 13 and 15.

This method is particularly suitable for the preparation of compounds of general formula (Ib) in which $R^{12}$ is substituted by a group $R^{13}$ as defined in general formula (I), for example where $R^{12}$ is a piperazinyl group substituted with a 5- or 6-membered carbocyclyl or aryl group such as cyclohexenyl or phenyl, which in turn, is substituted with an aryl group such as phenyl.

In some cases it is advantageous to protect the imine group of the starting compound of general formula (Ia). This is particularly the case when stronger reaction conditions need to be used, for example when the starting compound of general formula (Ia) is a compound in which $R^{10}$ is 2-bromophenyl. Protecting groups for imino moieties are well known and are discussed, for example in "Protecting Groups in Organic Synthesis", Theodora W. Greene and Peter G. M. Wuts, published by John Wiley & Sons Inc. Suitable protecting groups include tertiary butyl carbamate (BOC).

In a further embodiment, a compound of general formula (I) in which $R^1$ or $R^2$ has an ester substituent (i.e. a substituent $C(O)OR^8$ for $R^1$ or as substituent $C(O)OR^9$ or $C(O)OR^{11}$ for $R^2$) may be converted to a compound of general formula (I) in which $R^1$ or $R^2$ has a carboxylic acid substituent by hydrolysis. Alkaline hydrolysis is particularly suitable, for example using a strong base such as sodium hydroxide. This type of reaction is exemplified in Examples 14, and 16-18 below.

A compound of general formula (I) in which $R^1$ has a carboxylic acid substituent may be converted to the equivalent compound of general formula (I) in which $R^1$ is substituted with $C(O)NHSO_2R^8$ by reaction with the appropriate alkane sulfonamide. This type of reaction is illustrated by Example 20 below.

Compounds of general formula (I) will generally be administered in a pharmaceutical composition and compositions comprising novel compounds of the invention are also novel. Therefore in a further aspect of the invention there is provided a pharmaceutical composition comprising a compound according to the second aspect of the invention or a tautomer, enantiomer or pharmaceutically acceptable salt, hydrate, solvate, complex or prodrug thereof together with a pharmaceutically acceptable excipient.

The carrier, or, if more than one be present, each of the carriers, must be acceptable in the sense of being compatible with the other ingredients of the composition and not deleterious to the recipient.

The compositions include formulations suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy. The route of administration will depend upon exact nature of the condition to be treated.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a novel compound of general formula (I) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit anti-apoptotic Bcl-2 proteins. The precise amount of a compound of general formula (I) which is therapeutically effective, and the route by which such compound is best administered, is readily determined by one of ordinary skill in the art by comparing the blood level of the agent to the concentration required to have a therapeutic effect.

The invention will now be described in greater detail with reference to the following non limiting examples and the drawing in which:

FIG. 1 is a schematic drawing of the Bcl-2: Bak (72-87) interaction assay based on fluorescence polarisation.

In the Examples, the following terms are used.

| Abbreviations | |
|---|---|
| BINAP | 2,2'-bis(diphenylphosphino)-1,1'-binaphthyl |
| d | day |
| dba | dibenzylideneacetone |
| DMAP | 4-dimethylaminopyridine |
| dppf | 1,1'-bis(diphenylphosphino)ferrocene |
| EDC | (1-ethyl-3-(3-dimethyllaminopropyl) carbodiimide hydrochloride) |
| Et | ethanol |
| h | hour |
| HOBt | N-hydroxybenzotriazole |
| HPLC | high performance liquid chromatography |
| HPLC-MS | liquid chromatography mass spectrometry |
| min | minutes |
| NMR | nuclear magnetic resonance |
| rt | room temperature |
| TFA | trifluoroacetic acid |
| TLC | thin layer chromatography |

Analytical Methods

The analytical methods used to characterise compounds comprised HPLC-MS and $^1$H NMR.

HPLC-MS Analysis Conditions

| Column | Waters Atlantis dC18 100 × 2.1 mm, 3 µm column 40° C. |
|---|---|
| Mobile phase | A - 0.1% Formic acid (water) B - 0.1% Formic acid (acetonitrile) |
| Flow rate | 0.6 ml/min |
| Injection volume | 3 µl |
| Detector | 215 nm (nominal) |

| Gradient | Time (mins) | % Organic |
|---|---|---|
| | 0.00 | 5 |
| | 5.00 | 100 |
| | 5.40 | 100 |
| | 5.42 | 5 |
| | 7.00 | 5 |

HPLC-MS Preparative Conditions

| Column | Waters SunFire Prep C18 OBD 5 um 19 × 100 mm |
|---|---|
| Mobile phase | A, TFA (aq) 0.1% B, TFA (CH$_3$CN) 0.1% |
| Flow rate | 26 ml/min |
| Injection volume | 1000 µl |
| Detector | 215 nm (nominal) |

| Gradient | Time (mins) | % Organic |
|---|---|---|
| | 0.00 | 10 |
| | 1 | 10 |
| | 7.5 | 100 |
| | 9 | 100 |
| | 9.1 | 10 |

Example 1

Synthesis of 1-benzyl-3-pyridin-2-ylmethyl-1,3-dihydro-benzoimidazol-2-ylideneamine (Compound 1)

Compound 1 was synthesised according to the Scheme 1 set out below.

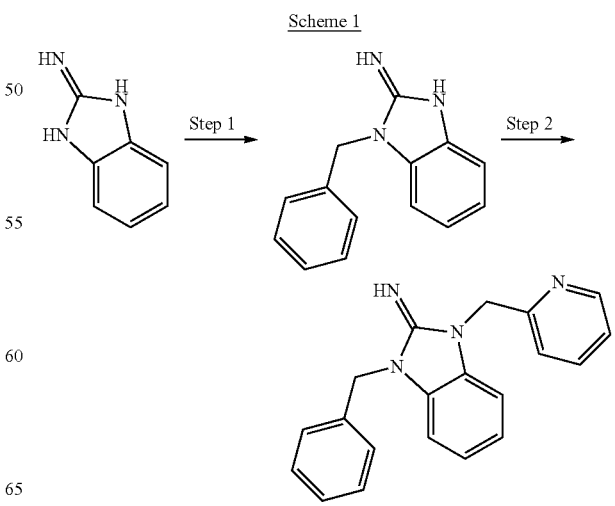

Scheme 1

Step 1 Synthesis of 1-benzyl-1,3-dihydro-benzoimidazol-2-ylideneamine

To a suspension of 1,3-dihydro-benzoimidazol-2-ylidene amine (5.0 g, 37.6 mmol) in EtOH (15 ml) at rt was added KOH (2.53 g, 45.1 mmol). The reaction was stirred for 1 h before benzyl bromide (4.92 ml, 41.4 mmol) was introduced and then the reaction was stirred for 2 d. After this time, the mixture was concentrated under reduced pressure and purified by chromatography on silica eluting with MeOH/dichloromethane (1.5-5% gradient). This provided 1-benzyl-1,3-dihydro-benzoimidazol-2-ylideneamine (4.47 g, 50%). HPLC-MS 224 [M+1]$^+$.

Using a similar procedure with 1,3-dihydro-benzoimidazol-2-ylidene amine and the appropriate alkyl bromide reagent the compounds in Table 1 were prepared. The following modifications are noted:

- 1-(3-Bromo-benzyl)-1,3-dihydro-benzoimidazol-2-ylideneamine: The crude product was partitioned between dichloromethane and saturated NaHCO$_3$ and stirred for 10 min. After this time the organic phase was separated, dried (Na$_2$SO$_4$), filtered and concentrated under reduced pressure to give the title compound which was used without further purification.
- 1-[3-(4-Fluoro-phenoxy)-propyl]-1,3-dihydro-benzoimidazol-2-ylideneamine: The reaction was stirred for 7 d.
- 1-(3-Phenoxy-propyl)-1,3-dihydro-benzoimidazol-2-ylideneamine: The reaction was stirred for 3 d at rt.
- 1-(2-Phenylsulfanyl-ethyl)-1,3-dihydro-benzoimidazol-2-ylideneamine: The reaction was stirred for 2.5 d.

TABLE 1

| Structure | Name | HPLC-MS | Yield |
|---|---|---|---|
| 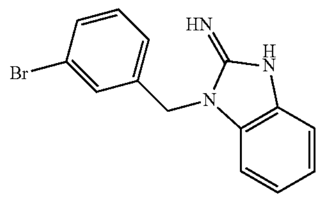 [SMILES: N=c1[nH]c2ccccc2n1Cc1cccc(Br)c1] | 1-(3-Bromo-benzyl)-1,3-dihydro-benzoimidazol-2-ylideneamine | 301, 303 [M + 1]$^+$ | 65% |
| 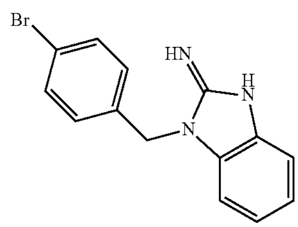 [SMILES: N=c1[nH]c2ccccc2n1Cc1ccc(Br)cc1] | 1-(4-Bromo-benzyl)-1,3-dihydro-benzoimidazol-2-ylideneamine | 301, 303 [M + 1]$^+$ | 69% |
| 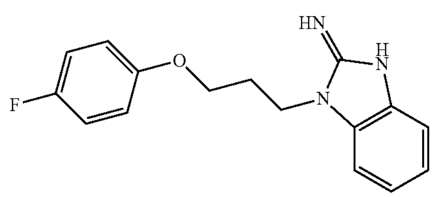 [SMILES: N=c1[nH]c2ccccc2n1CCCOc1ccc(F)cc1] | 1-[3-(4-Fluoro-phenoxy)-propyl]-1,3-dihydro-benzoimidazol-2-ylideneamine | 286 [M + 1]$^+$ | 55% |
| 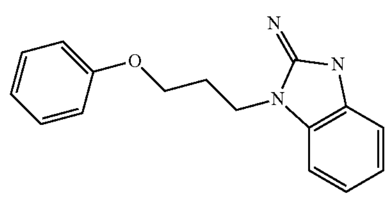 [SMILES: N=c1[nH]c2ccccc2n1CCCOc1ccccc1] | 1-(3-Phenoxy-propyl)-1,3-dihydro-benzoimidazol-2-ylideneamine | 268 [M + 1]$^+$ | 48% |
| 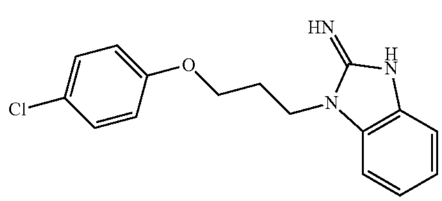 [SMILES: N=c1[nH]c2ccccc2n1CCCOc1ccc(Cl)cc1] | 1-[3-(4-Chloro-phenoxy)-propyl]-1,3-dihydro-benzoimidazol-2-ylideneamine | 302, 304 [M + 1]$^+$ | 18% |

TABLE 1-continued

| Structure | Name | HPLC-MS | Yield |
|---|---|---|---|
| 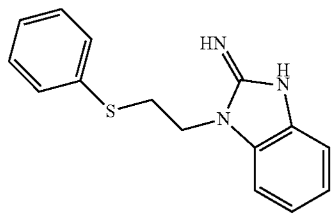 [SMILES: N=c1[nH]c2ccccc2n1CCSc1ccccc1] | 1-(2-Phenylsulfanyl-ethyl)-1,3-dihydro-benzoimidazol-2-ylideneamine | 270 [M + 1]+ | 40% |

Step 2 Synthesis of 1-benzyl-3-pyridin-2-ylmethyl-1,3-dihydro-benzoimidazol-2-ylideneamine (Compound 1)

A suspension of 1-benzyl-1,3-dihydro-benzoimidazol-2-ylideneamine (150 mg, 0.67 mmol), 2-bromomethylpyridine, hydrobromide salt (170 mg, 0.67 mmol) and Na$_2$CO$_3$ (71 mg, 0.67 mmol) in EtOH (3 ml) was heated to 80° C. in a sealed tube. After 5 h, the reaction was cooled to rt and filtered.

The collected solids were washed with additional EtOH and the combined filtrate and washings were concentrated under reduced pressure. Purification by chromatography on silica eluting with 8% MeOH/dichloromethane provided 1-benzyl-3-pyridin-2-ylmethyl-1,3-dihydro-benzoimidazol-2-ylideneamine (17 mg, 22%). HPLC-MS 315 [M+1]+.

Using a similar procedure with 1-benzyl-1,3-dihydro-benzoimidazol-2-yfideneamine and the appropriate alkylating reagent the compounds in Table 2 were prepared. The following modifications are noted:

For compound 4 the alkylating agent used was toluene-4-sulfonic acid tetrahydro-pyran-4-ylmethyl ester.

TABLE 2

| Cpd | Structure | Name | HPLC-MS | Yield |
|---|---|---|---|---|
| 2 | 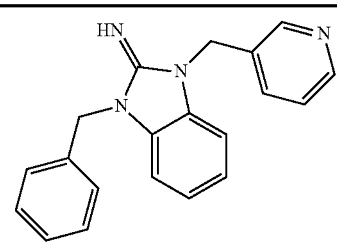 | 1-Benzyl-3-pyridin-3-ylmethyl-1,3-dihydro-benzoimidazol-2-ylideneamine | 315 [M + 1]+ | 5% |
| 3 | 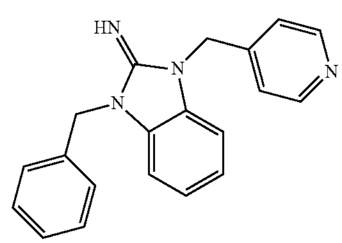 [SMILES: N=c1n(Cc2ccccc2)c2ccccc2n1Cc1ccncc1] | 1-Benzyl-3-pyridin-4-ylmethyl-1,3-dihydro-benzoimidazol-2-ylideneamine | 315 [M + 1]+ | 8% |
| 4 | 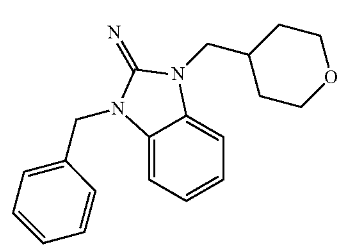 [SMILES: N=c1n(Cc2ccccc2)c2ccccc2n1CC1CCOCC1] | 1-Benzyl-3-(tetrahydro-pyran-4-ylmethyl)-1,3-dihydro-benzoimidazol-2-ylideneamine | 322 [M + 1]+ | 6% |

Example 2

Synthesis of 1-(4'-fluoro-biphenyl-4-ylmethyl)-3-[3-(4-fluoro-phenoxy)-propyl]-1,3-dihydro-benzoimidazol-2-ylideneamine (Compound 16)

The title compound was synthesised according to Scheme 2.

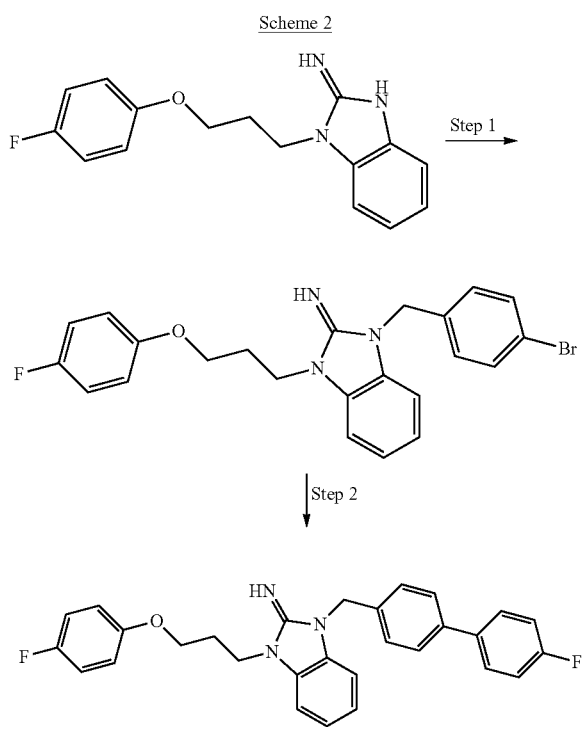 [SMILES: N=c1[nH]c2ccccc2n1CCCOc1ccc(F)cc1 ; N=c1n(CCCOc2ccc(F)cc2)c2ccccc2n1Cc1ccc(Br)cc1 ; N=c1n(CCCOc2ccc(F)cc2)c2ccccc2n1Cc1ccc(-c2ccc(F)cc2)cc1]

Scheme 2

Step 1 Synthesis of 1-(4-bromo-benzyl)-3-[3-(4-fluoro-phenoxy)-propyl]-1,3-dihydro-benzoimidazol-2-ylideneamine (Compound 5)

To a solution of 1-[3-(4-fluoro-phenoxy)-propyl]-1,3-dihydro-benzoimidazol-2-ylideneamine (0.40 g, 1.40 mmol) in 2-butanone (30 ml) was added 4-bromobenzyl bromide (0.52 g, 2.1 mmol). The reaction was heated to 90° C. for 16 h. After this time, the resulting suspension was cooled to rt and filtered. The collected solid was washed with additional 2-butanone and then the solid was partitioned between dichloromethane and a saturated solution of NaHCO₃. The biphasic mixture was stirred at rt for 10 min and then the organic layer was separated. The aqueous phase was extracted with additional dichloromethane and the combined organic fractions were washed with H₂O, dried (Na₂SO₄), filtered and concentrated under reduced pressure to provide 1-(4-bromo-benzyl)-3-[3-(4-fluoro-phenoxy)-propyl]-1,3-dihydro-benzoimidazol-2-ylideneamine as a white solid (0.532 g, 83%). HPLC-MS 454, 456 [M+1]⁺.

Using a similar procedure with the appropriate intermediates from Table 1 and the appropriate alkyl bromide the compounds in Table 3 were prepared. The following modifications are noted:

- 1-(3-Bromo-benzyl)-3-[3-(4-fluoro-phenoxy)-propyl]-1,3-dihydro-benzoimidazol-2-ylideneamine was prepared from 1-[3-(4-fluoro-phenoxy)-propyl]-1,3-dihydro-benzoimidazol-2-ylideneamine and 3-bromobenzyl bromide
- 1-(4-Bromo-benzyl)-3-(3-phenoxy-propyl)-1,3-dihydro-benzoimidazol-2-ylideneamine was prepared from 1-(3-Phenoxy-propyl)-1,3-dihydro-benzoimidazol-2-ylideneamine and 4-bromobenzyl bromide
- 1-(4-Bromo-benzyl)-3-(3-phenoxy-propyl)-1,3-dihydro-benzoimidazol-2-ylideneamine was prepared from 1-(3-Phenoxy-propyl)-1,3-dihydro-benzoimidazol-2-ylideneamine and 3-bromobenzyl bromide
- 1-(4-Bromo-benzyl)-3-(2-phenylsulfanyl-ethyl)-1,3-dihydro-benzoimidazol-2-ylideneamine was prepared from 1-(2-Phenylsulfanyl-ethyl)-1,3-dihydro-benzoimidazol-2-ylideneamine and 4-bromobenzyl bromide
- 1-(4-Bromo-benzyl)-3-[3-(4-chloro-phenoxy)-propyl]-1,3-dihydro-benzoimidazol-2-ylideneamine was prepared from 1-[3-(4-chloro-phenoxy)-propyl]-1,3-dihydro-benzoimidazol-2-ylideneamine and 4-bromobenzyl bromide
- 1-(2-Bromo-benzyl)-3-[3-(4-fluoro-phenoxy)-propyl]-1,3-dihydro-benzoimidazol-2-ylideneamine: compound was isolated as the hydrobromide salt (no basic work-up was used)
- 1-[3-(4-Chloro-phenoxy)-propyl]-3-pyridin-4-ylmethyl-1,3-dihydro-benzoimidazol-2-ylideneamine and 1-(4-Bromo-benzyl)-3-[3-(4-chloro-phenoxy)-propyl]-1,3-dihydro-benzoimidazol-2-ylideneamine: EtOH was used as the solvent for the reaction and Na₂CO₃ (3 equivalents) were used in the reaction
- 3-{3-[3-(4-Fluoro-phenoxy)-propyl]-2-imino-2,3-dihydro-benzoimidazol-1-ylmethyl}-benzoic acid methyl ester: compound was isolated as the hydrobromide salt.

TABLE 3

| Cpd | Structure | Name | HPLC-MS | Yield |
|---|---|---|---|---|
| 6 | 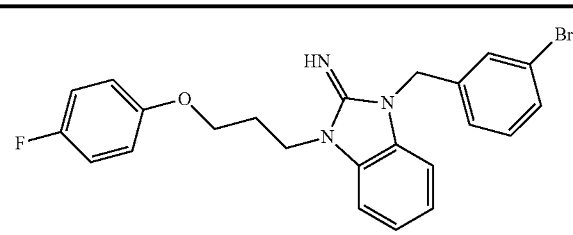 | 1-(3-Bromo-benzyl)-3-[3-(4-fluoro-phenoxy)-propyl]-1,3-dihydro-benzoimidazol-2-ylideneamine | 454, 456 [M + 1]⁺ | 80% |

TABLE 3-continued

| Cpd | Structure | Name | HPLC-MS | Yield |
|---|---|---|---|---|
| | | 1-(2-Bromo-benzyl)-3-[3-(4-fluoro-phenoxy)-propyl]-1,3-dihydro-benzoimidazol-2-ylideneamine | 454, 456 [M + 1]$^+$ | 95% |
| | | 1-(4-Bromo-benzyl)-3-(3-phenoxy-propyl)-1,3-dihydro-benzoimidazol-2-ylideneamine | 436, 438 [M + 1]$^+$ | 17% |
| | | 1-(3-Bromo-benzyl)-3-(3-phenoxy-propyl)-1,3-dihydro-benzoimidazol-2-ylideneamine | 436, 438 [M + 1]$^+$ | 53% |
| 7 | 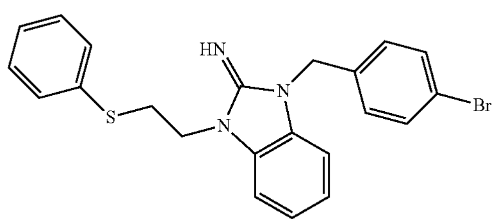 [SMILES: N=c1n(CCSc2ccccc2)c2ccccc2n1Cc1ccc(Br)cc1] | 1-(4-Bromo-benzyl)-3-(2-phenylsulfanyl-ethyl)-1,3-dihydro-benzoimidazol-2-ylideneamine | 438, 440 [M + 1]$^+$ | 78% |
| 8 | 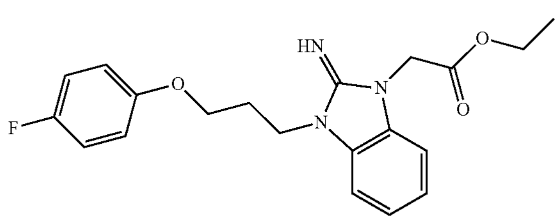 [SMILES: CCOC(=O)Cn1c(=N)n(CCCOc2ccc(F)cc2)c2ccccc21] | {3-[3-(4-Fluoro-phenoxy)-propyl]-2-imino-2,3-dihydro-benzoimidazol-1-yl}-acetic acid ethyl ester | 372 [M + 1]$^+$ | 67% |
| 9 | 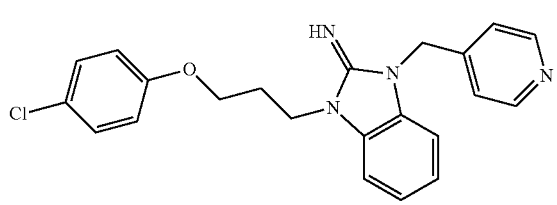 [SMILES: N=c1n(CCCOc2ccc(Cl)cc2)c2ccccc2n1Cc1ccncc1] | 1-[3-(4-Chloro-phenoxy)-propyl]-3-pyridin-4-ylmethyl-1,3-dihydro-benzoimidazol-2-ylideneamine | 393, 395 [M + 1]$^+$ | 18% |
| 10 | 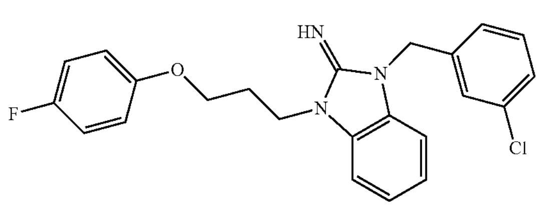 [SMILES: N=c1n(CCCOc2ccc(F)cc2)c2ccccc2n1Cc1cccc(Cl)c1] | 1-(3-Chloro-benzyl)-3-[3-(4-fluoro-phenoxy)-propyl]-1,3-dihydro-benzoimidazol-2-ylideneamine | 410, 412 [M + 1]$^+$ | 100% |

TABLE 3-continued

| Cpd | Structure | Name | HPLC-MS | Yield |
|---|---|---|---|---|
| 11 | 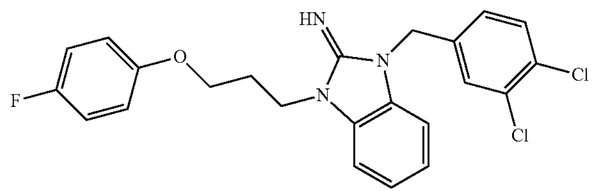 [SMILES: N=c1n(CCCOc2ccc(F)cc2)c2ccccc2n1Cc1ccc(Cl)c(Cl)c1] | 1-(3,4-Dichloro-benzyl)-3-[3-(4-fluoro-phenoxy)-propyl]-1,3-dihydro-benzoimidazol-2-ylideneamine | 444, 446 [M + 1]+ | 45% |
| 12 | 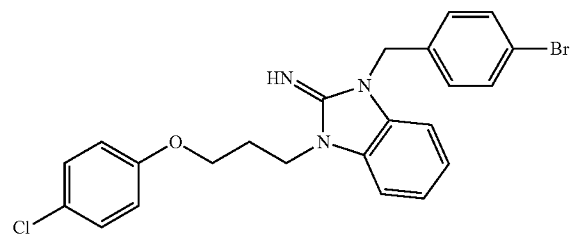 [SMILES: N=c1n(CCCOc2ccc(Cl)cc2)c2ccccc2n1Cc1ccc(Br)cc1] | 1-(4-Bromo-benzyl)-3-[3-(4-chloro-phenoxy)-propyl]-1,3-dihydro-benzoimidazol-2-ylideneamine | 470, 472 [M + 1]+ | 37% |
| 13 | 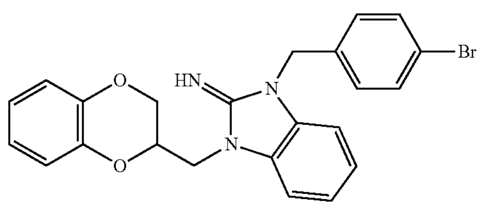 [SMILES: N=c1n(Cc2ccc(Br)cc2)c2ccccc2n1CC1COc2ccccc2O1] | 1-(4-Bromo-benzyl)-3-(2,3-dihydro-benzo[1,4]dioxin-2-ylmethyl)-1,3-dihydro-benzoimidazol-2-ylideneamine | 450, 452 [M + 1]+ | 24% |
| 14 | 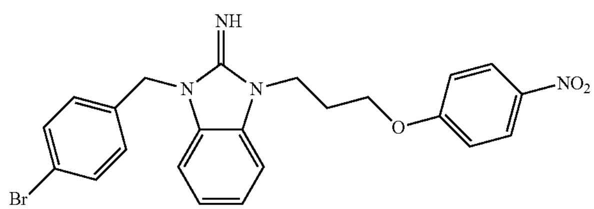 [SMILES: N=c1n(CCCOc2ccc([N+](=O)[O-])cc2)c2ccccc2n1Cc1ccc(Br)cc1] | 1-(4-Bromo-benzyl)-3-[3-(4-nitro-phenoxy)-propyl]-1,3-dihydro-benzoimidazol-2-ylideneamine | 481, 483 [M + 1]+ | 57% |
| 15 | 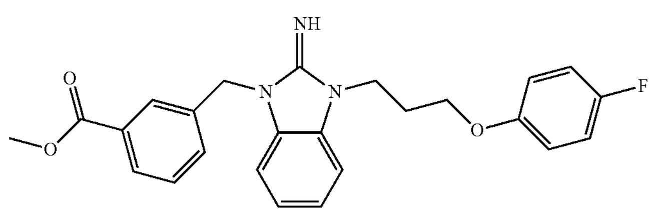 [SMILES: COC(=O)c1cccc(Cn2c(=N)n(CCCOc3ccc(F)cc3)c3ccccc32)c1] | 3-{3-[3-(4-Fluoro-phenoxy)-propyl]-2-imino-2,3-dihydro-benzoimidazol-1-ylmethyl}-benzoic acid methyl ester | 434 [M + 1]+ | 41% |

Step 2 Synthesis of 1-(4'-fluoro-biphenyl-4-ylmethyl)-3-[3-(4-fluoro-phenoxy)-propyl]-1,3-dihydro-benzoimidazol-2-ylideneamine (Compound 16)

Nitrogen was bubbled through a mixture of 1-(4-bromo-benzyl)-3-[3-(4-fluoro-phenoxy)-propyl]-1,3-dihydro-benzoimidazol-2-ylideneamine (80 mg, 0.18 mmol) and 4-fluorophenyl boronic acid (37 mg, 0.26 mmol) in 3:1 MeOH/1,4-dioxane (3 ml) at rt for 10 min before a solution of 2M Na$_2$CO$_3$ (0.17 ml, 0.35 mmol) was introduced. The suspension was degassed for a further 2 min and then PdCl$_2$(dppf) (14 mg, 0.02 mmol) was added. The reaction mixture was sealed and heated to 100° C. where it was maintained for 16 h. After this time, the suspension was cooled to rt and filtered through Celite®. The filtrate was concentrated under reduced pressure and the crude product that remained was purified by preparative HPLC to provide 1-(4'-fluoro-biphenyl-4-ylmethyl)-3-[3-(4-fluoro-phenoxy)-propyl]-1,3-dihydro-benzoimidazol-2-ylideneamine (30 mg, 36%). HPLC-MS 470 [M+1]+.

Example 3

Synthesis of 1-[4-(4-biphenyl-2-ylmethyl-piperazin-1-yl)-benzyl]-3-methyl-1,3-dihydro-benzoimidazol-2-ylideneamine (Compound 17)

The title compound was synthesised according to the method shown in Scheme 3.

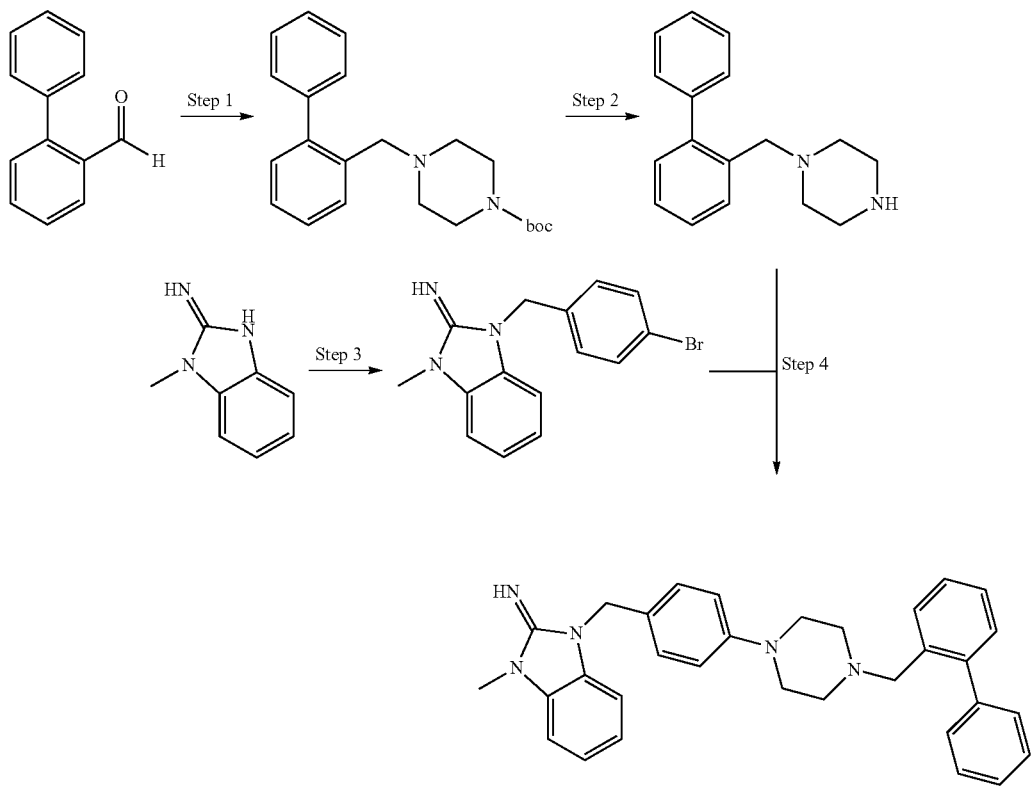

Scheme 3

Step 1 Synthesis of 4-biphenyl-2-ylmethyl-piperazine-1-carboxylic acid tert-butyl ester To a solution of biphenyl-2-carbaldehyde (5.01 g, 27.5 mmol) in dichloromethane (150 ml) at rt under nitrogen was added piperazine-1-carboxylic acid tert-butyl ester (5.63 g, 30.2 mmol) followed by glacial acetic acid (1.90 ml, 33.2 mmol). The reaction was stirred for 1 h before sodium triacetoxyborohydride (11.65 g, 55.0 mmol) was introduced. After 3 h, a solution of 5% NaOH (~15 ml) was added and the mixture was extracted with dichloromethane. The organic layer was separated, washed with H$_2$O (×2), brine, dried (Na$_2$SO$_4$), filtered and concentrated under reduced pressure to give 4-biphenyl-2-ylmethyl-piperazine-1-carboxylic acid tert-butyl ester as an oil (9.9 g, 100%) which was used without further purification. HPLC-MS 353 [M+1]$^+$.

Using a similar procedure starting from 4'-chloro-biphenyl-2-carbaldehyde the compound in Table 4 was prepared. This compound was purified by column chromatography on silica eluting with 5% EtOAc/heptanes.

TABLE 4

| Structure | Name | HPLC-MS | Yield |
|---|---|---|---|
| (structure with Cl) | 4-(4'-Chloro-biphenyl-2-ylmethyl)-piperazine-1-carboxylic acid tert-butyl ester | 387, 389 [M + 1]$^+$ | 59% |

Step 2 Synthesis of 1-biphenyl-2-ylmethyl-piperazine

To a solution of 4-biphenyl-2-ylmethyl-piperazine-1-carboxylic acid tert-butyl ester (9.89 g, 28.1 mmol) in dichloromethane (112.5 ml) at rt was added TFA (37.5 ml). The reaction was stirred for 4.5 h and then concentrated under reduced pressure. To the crude product was added H$_2$O (20 ml) followed by 1M NaOH and then 5M NaOH to adjust the pH to ~8-9. The mixture was extracted with dichloromethane (×2) and the combined organic extracts were washed with H₂O, brine, dried (Na₂SO₄), filtered and concentrated under reduced pressure to provide 1-biphenyl-2-ylmethyl-piperazine (6.55 g, 92%) which was used without further purification. HPLC-MS 253 [M+1]⁺.

Using a similar procedure starting from 4-(4'-Chloro-biphenyl-2-ylmethyl)-piperazine-1-carboxylic acid tert-butyl ester the compound in Table 5 was prepared

TABLE 5

| Structure | Name | HPLC-MS | Yield |
|---|---|---|---|
| 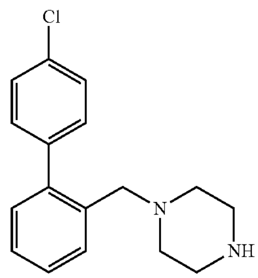 [SMILES: Clc1ccc(-c2ccccc2CN2CCNCC2)cc1] | 1-(4'-Chloro-biphenyl-2-ylmethyl)-piperazine | 287, 289 [M + 1]⁺ | 100% |

Step 3 Synthesis of 1-(4-bromo-benzyl)-3-methyl-1,3-dihydro-benzoimidazol-2-ylideneamine To a solution of 1-methyl-1,3-dihydro-benzoimidazol-2-ylideneamine (0.30 g, 2.04 mmol) in 2-butanone (30 ml) was added 4-bromobenzyl bromide (0.70 g, 2.81 mmol). The reaction was heated to 90° C. where it was stirred for 30 min. After this time, the resulting suspension was cooled to rt and filtered. The collected solids were partitioned between dichloromethane and a saturated solution of NaHCO₃ and the mixture was stirred for 10 min. The organic layer was separated and the aqueous phase was extracted with additional dichloromethane. The organic fractions were combined, washed with H₂O, dried (Na₂SO₄), filtered and the filtrate was concentrated under reduced pressure to give 1-(4-bromo-benzyl)-3-methyl-1,3-dihydro-benzoimidazol-2-ylideneamine as a white solid (0.39 g, 61%). HPLC-MS 316, 318 [M+1]⁺.

Using a similar procedure starting from 1-benzyl-1,3-dihydro-benzoimidazol-2-ylideneamine the compound in Table 6 was prepared:

Step 4

Synthesis of 1-[4-(4-biphenyl-2-ylmethyl-piperazin-1-yl)-benzyl]-3-methyl-1,3-dihydro-benzoimidazol-2-ylideneamine (Compound 17)

To a degassed solution of 1-(4-bromo-benzyl)-3-methyl-1,3-dihydro-benzoimidazol-2-ylideneamine (75 mg, 0.237 mmol) in anhydrous toluene (2 ml) was added Pd(OAc)₂ (20 mg, 0.047 mmol). Nitrogen was bubbled through the suspension for 10 min before BINAP (29 mg, 0.047 mmol) was added. After a further 2 min 1-biphenyl-2-ylmethyl-piperazine (65 mg, 0.258 mmol) in degassed toluene (2 ml) was introduced and then after a additional 2 min Cs₂CO₃ (1.54 g, 4.75 mmol) was added and the reaction was stirred for 2 min. Throughout all of the additions nitrogen was continuously bubbled through the reaction mixture. The reaction was then sealed and heated to 95° C. where it was maintained for 16 h. After this time the dark red mixture was cooled to rt and filtered through Celite®. The collected solids were washed with additional toluene and then the combined filtrate and washings were concentrated under reduced pressure to give the crude product. Purification by preparative HPLC provided 1-[4-(4-biphenyl-2-ylmethyl-piperazin-1-yl)-benzyl]-3-methyl-1,3-dihydro-benzoimidazol-2-ylideneamine as a solid (14 mg, 12%). HPLC-MS 488 [M+1]⁺, 255.

Using a similar procedure starting from 1-benzyl-3-(4-bromo-benzyl)-1,3-dihydro-benzoimidazol-2-ylideneamine the compound in Table 7 was prepared:

TABLE 6

| Structure | Name | HPLC-MS | Yield |
|---|---|---|---|
| 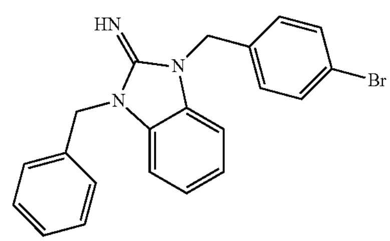 [SMILES: N=c1n(Cc2ccccc2)c2ccccc2n1Cc1ccc(Br)cc1] | 1-Benzyl-3-(4-bromo-benzyl)-1,3-dihydro-benzoimidazol-2-ylideneamine | 392, 394 [M + 1]⁺ | 68% |

TABLE 7

| Cpd | Structure | Name | HPLC-MS | Yield |
|---|---|---|---|---|
| 18 | 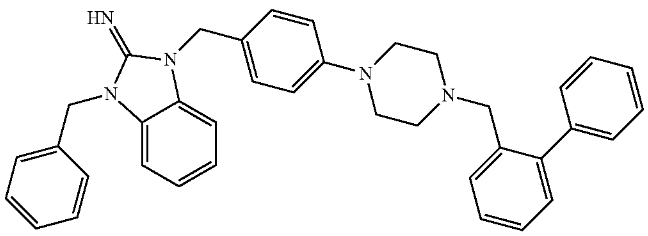 [SMILES: N=c1n(Cc2ccccc2)c2ccccc2n1Cc1ccc(N2CCN(Cc3ccccc3-c3ccccc3)CC2)cc1] | 1-Benzyl-3-[4-(4-biphenyl-2-ylmethyl-piperazin-1-yl)-benzyl]-1,3-dihydro-benzoimidazol-2-ylideneamine | 564 [M + 1]+, 283 | 10% |

Example 4

Synthesis of 1-{4-[4-(4-chloro-benzyl)-piperazin-1-yl]-benzyl}-3-[3-(4-fluoro-phenoxy)-propyl]-1,3-dihydro-benzoimidazol-2-ylideneamine (Compound 19)

The title compound was prepared according to Scheme 4.

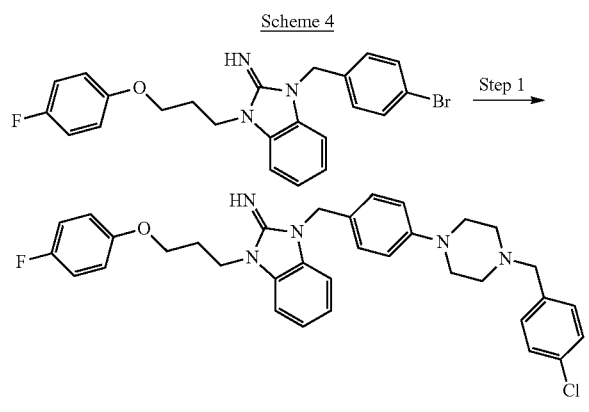

Scheme 4

Step 1 Synthesis of 1-{4-[4-(4-chloro-benzyl)-piperazin-1-yl]-benzyl}-3-[3-(4-fluoro-phenoxy)-propyl]-1,3-dihydro-benzoimidazol-2-ylideneamine (Compound 19)

To a solution 1-(4-bromo-benzyl)-3-[3-(4-fluoro-phenoxy)-propyl]-1,3-dihydro-benzoimidazol-2-ylideneamine (0.25 g, 0.55 mmol) in toluene (20 ml) was added 1-(4-chloro-benzyl)-piperazine (0.16 g, 0.55 mmol), potassium t-butoxide (216 mg, 1.93 mmol), $Pd_2(dba)_3$ (35 mg, 0.038 mmol) and BINAP (48 mg, 0.077 mmol). Nitrogen was bubbled through the suspension for 5 min and then the reaction was heated to 105° C. for 24 h. After this time, the mixture was cooled to rt and filtered. The collected solids were washed with additional toluene and then the combined filtrate and washings were concentrated under reduced pressure. The crude product was purified by chromatography on silica to provide 1-{4-[4-(4-chloro-benzyl)-piperazin-1-yl]-benzyl}-3-[3-(4-fluoro-phenoxy)-propyl]-1,3-dihydro-benzoimidazol-2-ylideneamine (57 mg, 18%). HPLC-MS 584 [M+1]+, 293.

Using a similar procedure starting from 1-(4-bromo-benzyl)-3-[3-(4-fluoro-phenoxy)-propyl]-1,3-dihydro-benzoimidazol-2-ylideneamine and using the appropriate amine the compounds in Table 8 were prepared.

TABLE 8

| Cpd | Structure | Name | HPLC-MS | Yield |
|---|---|---|---|---|
| 20 | 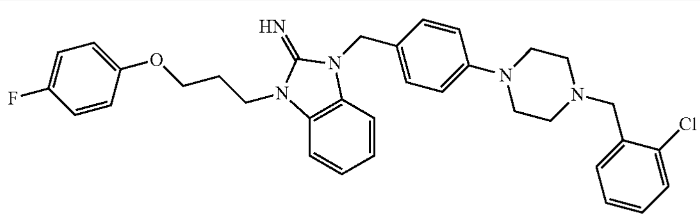 [SMILES: N=c1n(CCCOc2ccc(F)cc2)c2ccccc2n1Cc1ccc(N2CCN(Cc3ccccc3Cl)CC2)cc1] | 1-{4-[4-(2-Chloro-benzyl)-piperazin-1-yl]-benzyl}-3-[3-(4-fluoro-phenoxy)-propyl]-1,3-dihydro-benzoimidazol-2-ylideneamine | 584 [M + 1]+, 293 | 19% |
| 21 | 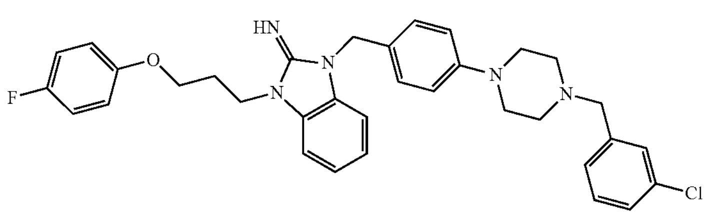 [SMILES: N=c1n(CCCOc2ccc(F)cc2)c2ccccc2n1Cc1ccc(N2CCN(Cc3cccc(Cl)c3)CC2)cc1] | 1-{4-[4-(3-Chloro-benzyl)-piperazin-1-yl]-benzyl}-3-[3-(4-fluoro-phenoxy)-propyl]-1,3-dihydro-benzoimidazol-2-ylideneamine | 584 [M + 1]+, 291 (100%) | 10% |

| Cpd | Structure | Name | HPLC-MS | Yield |
|---|---|---|---|---|
| 22 | 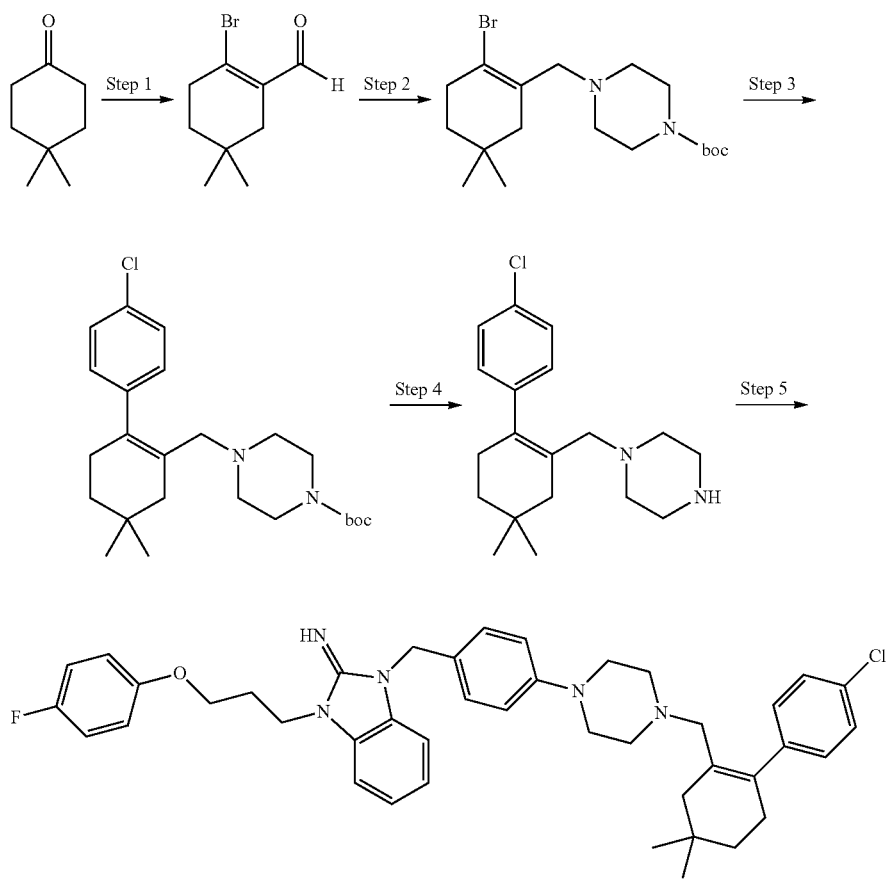 | 1-[4-(4-Benzyl-piperazin-1-yl)-benzyl]-3-[3-(4-fluoro-phenoxy)-propyl]-1,3-dihydro-benzoimidazol-2-ylideneamine | 550 [M + 1]+, 276 (100%) | 33% |

Example 5

Synthesis of 1-(4-{4-[2-(4-chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine (Compound 23)

Scheme 5 shows the synthetic route to the title compound.

Step 1 Synthesis of 2-bromo-5,5-dimethyl-cyclohex-1-ene carbaldehyde

A 3-necked round bottom flask equipped with a nitrogen inlet, a thermometer and an outlet connected to a scrubber containing a solution of 2M NaOH was charged with anhydrous chloroform (15 ml) and anhydrous N,N-dimethylformamide (2.5 ml (32.3 mmol). The solution was cooled to ~3° C. (internal temperature) under nitrogen before phosphorus tribromide (2.8 ml, 30.0 mmol) was introduced dropwise at a rate so that the reaction was maintained at ~3° C. After the addition was complete the reaction was allowed to warm slowly to ~10° C. and then the temperature was raised to 70° C. where it was maintained for 30 min. The reaction was cooled to rt and 4,4-dimethylcyclohexanone (1.4 g, 11.1 mmol) was added slowly over 20 min. After the addition was complete the reaction was warmed to 70° C. and it was stirred for 1.5 h. The mixture was then cooled to rt and poured onto a solution of 4M sodium acetate (15 ml). The pH of the resulting solution was adjusted to ~7 using a solution of 5M NaOH and the mixture was then extracted with heptanes (×5). The combined organic fractions were dried (Na$_2$SO$_4$), filtered and concentrated under reduced pressure to give 2-bromo-5,5-dimethyl-cyclohex-1-ene carbaldehyde as a yellow oil (1.4 g, 58%). $^1$H NMR (MeOD) δ 10.05 (1H, s), 2.82 (2H, m), 2.10 (2H, m), 1.59 (2H, t), 0.96 (6H, s).

Step 2 Synthesis of 4-(2-bromo-5,5-dimethyl-cyclohex-1-enylmethyl)-piperazine-1-carboxylic acid tert-butyl ester To a solution of 2-bromo-5,5-dimethyl-cyclohex-1-ene carbaldehyde (1 g, 4.61 mmol) in dichloromethane (70 ml) at rt under nitrogen was added glacial acetic acid (0.29 ml, 5.1 mmol) followed by piperazine-1-carboxylic acid tert-butyl ester (0.94 g, 5.07 mmol). The reaction was stirred for 1 h before sodium triacetoxyborohydride (2.05 g, 9.68 mmol) was introduced. After 16 h, a solution of 5% NaOH (20 ml) was added and the mixture was extracted with dichloromethane. The organic layer was separated and washed with H$_2$O, dried (Na$_2$SO$_4$), filtered and concentrated under reduced pressure to give the crude product. Purification by column chromatography on silica eluting with 5% EtOAc/heptane provided 4-(2-bromo-5,5-dimethyl-cyclohex-1-enylmethyl)-piperazine-1-carboxylic acid tert-butyl ester (1.3 g, 73%).-$^1$H NMR (MeOD) δ 3.44 (4H, br t), 3.14 (2H, br s), 2.55 (2H, br m), 2.40 (4H, br t), 2.08 (2H, br s), 1.51 (2H, t), 1.48 (9H, s), 0.93 (6H, s).

Step 3 Synthesis of 4-[2-(4-chloro-phenyl)-5,5-dimethyl-cyclohex-1-enylmethyl]-piperazine-1-carboxylic acid tert-butyl ester To a degassed solution of 4-(2-bromo-5,5-dimethyl-cyclohex-1-enylmethyl)-piperazine-1-carboxylic acid tert-butyl ester (1.3 g, 3.36 mmol) and 4-chlorophenyl boronic acid (0.78 g, 5.04 mmol) in 2:1 MeOH/1,4-dioxane (20 ml) at rt was added a solution of 2M Na$_2$CO$_3$ (3.3 ml, 6.72 mmol). Nitrogen was bubbled through the mixture for 2 min and then PdCl$_2$[dppf] (200 mg, 0.28 mmol) was added. The reaction flask was sealed and heated to 100° C. where it was maintained for 1 h. After this time the suspension was cooled to rt and filtered through Celite®. The collected solids were washed with additional dichloromethane and the combined filtrate and washings were concentrated under reduced pressure. Purification by column chromatography on silica eluting with 6% EtOAc/heptanes gave 4-[2-(4-chloro-phenyl)-5,5-dimethyl-cyclohex-1-enylmethyl]-piperazine-1-carboxylic acid tert-butyl ester (1.0 g, 71%). HPLC-MS 419, 421 [M+1]$^+$.

Step 4 Synthesis of 1-[2-(4-chloro-phenyl)-5,5-dimethyl-cyclohex-1-enylmethyl]-piperazine To a solution of 4-[2-(4-chloro-phenyl)-5,5-dimethyl-cyclohex-1-enylmethyl]-piperazine-1-carboxylic acid tert-butyl ester (1.0 g, 2.39 mmol) in dichloromethane (20 ml) was added TFA (5 ml). The reaction was stirred for 1 h and then concentrated under reduced pressure. A saturated solution of NaHCO$_3$ was added to adjust the pH to ~8-9 and the mixture was extracted with dichloromethane (×2). The combined extracts were washed with brine, dried (Na$_2$SO$_4$), filtered and concentrated under reduced pressure to give 1-[2-(4-chloro-phenyl)-5,5-dimethyl-cyclohex-1-enylmethyl]-piperazine (0.76 g, 100%). HPLC-MS 319, 321 [M+1]$^+$.

Step 5 Synthesis of 1-(4-{4-[2-(4-chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine (Compound 23)

To a degassed solution of 1-(4-bromo-benzyl)-3-[3-(4-fluoro-phenoxy)-propyl]-1,3-dihydro-benzoimidazol-2-ylideneamine (60 mg, 0.13 mmol) in anhydrous toluene (2 ml) was added Pd(OAc)$_2$ (0.3 mg, 0.7 μmol). Nitrogen was bubbled through the suspension for 10 min before BINAP (8 mg, 11 μmol) was added. After a further 2 min 1-[2-(4-chloro-phenyl)-5,5-dimethyl-cyclohex-1-enylmethyl]-piperazine (48 mg, 0.14 mmol) in degassed toluene (2 ml) was introduced and then after a additional 2 min Cs$_2$CO$_3$ (0.86 g, 2.6 mmol) was added and the reaction was stirred for 2 min. Throughout all of the additions nitrogen was continuously bubbled through the reaction mixture. The reaction was then sealed and heated to 95° C. where it was maintained for 2 h. After this time, the reaction was cooled to rt and additional Pd(OAc)$_2$ and BINAP were introduced. The reaction was then sealed and heated to 95° C. where it was maintained for a further 22 h. The mixture was cooled to rt and filtered through Celite®. The collected solids were washed with additional toluene and dichloromethane and then the combined filtrate and washings were concentrated under reduced pressure to give the crude product. After purification by preparative HPLC, the product was redissolved in dichloromethane and washed with saturated NaHCO$_3$ and H$_2$O. The organic phase was separated, dried (Na$_2$SO$_4$) and filtered to provide 1-(4-{4-[2-(4-chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine (10 mg, 11%). HPLC-MS 692 [M+1]$^+$, 347 (100%).

Using a similar procedure and the appropriate bromide and amine reagents, the compounds in Table 9 were prepared. The following modifications are noted:

Compound 28: Additional catalyst and ligand were added after 1d and reaction heated for a further 1d. Free-based using carbonate resin.

Compound 29: The reaction was heated in a microwave at 110° C. for 2 h. Additional catalyst and ligand were then added and heated in microwave at 110° C. for 50 min. Additional catalyst and ligand were added and the reaction was heated in microwave at 110° C. for a further 50 min.

Compound 32: Heated for 4 h.

TABLE 9

| Cpd | Structure | Name | HPLC-MS | Yield |
|---|---|---|---|---|
| 24 | 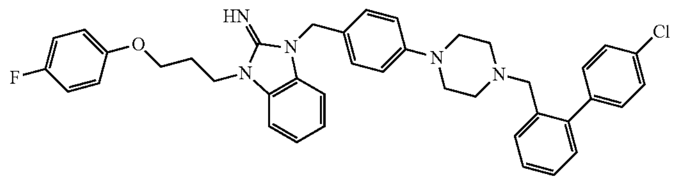 [SMILES: N=c1n(CCCOc2ccc(F)cc2)c2ccccc2n1Cc1ccc(N2CCN(Cc3ccccc3-c3ccc(Cl)cc3)CC2)cc1] | 1-{4-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine | 660 [M + 1]+, 331 (100%) | 9% |
| 25 | 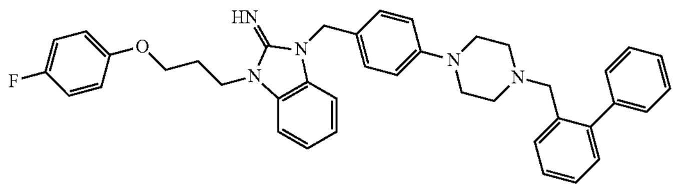 [SMILES: N=c1n(CCCOc2ccc(F)cc2)c2ccccc2n1Cc1ccc(N2CCN(Cc3ccccc3-c3ccccc3)CC2)cc1] | 1-[4-(4-Biphenyl-2-ylmethyl-piperazin-1-yl)-benzyl]-3-[3-(4-fluoro-phenoxy)-propyl]-1,3-dihydro-benzoimidazol-2-ylideneamine | 626 [M + 1]+, 314 | 23% |
| 26 | 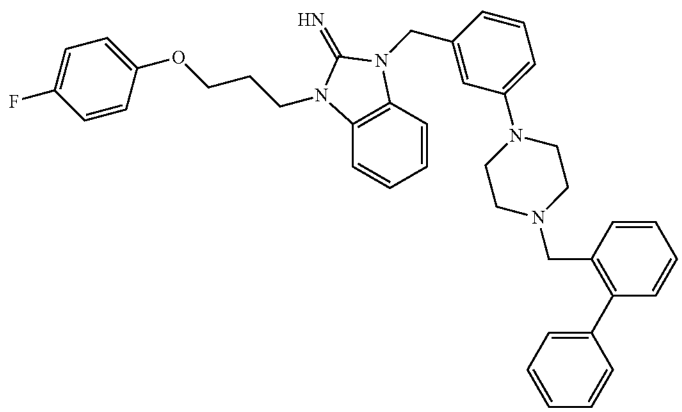 [SMILES: N=c1n(CCCOc2ccc(F)cc2)c2ccccc2n1Cc1cccc(N2CCN(Cc3ccccc3-c3ccccc3)CC2)c1] | 1-[3-(4-Biphenyl-2-ylmethyl-piperazin-1-yl)-benzyl]-3-[3-(4-fluoro-phenoxy)-propyl]-1,3-dihydro-benzoimidazol-2-ylideneamine | 626 [M + 1]+, 314 | 17% |
| 27 | 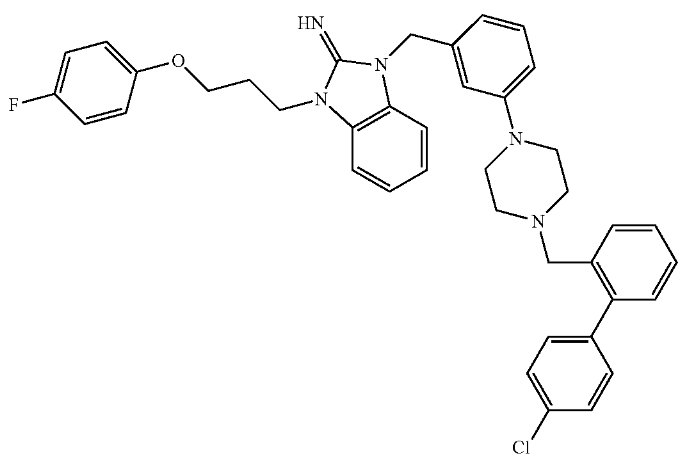 [SMILES: N=c1n(CCCOc2ccc(F)cc2)c2ccccc2n1Cc1cccc(N2CCN(Cc3ccccc3-c3ccc(Cl)cc3)CC2)c1] | 1-{3-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine | 660 [M + 1]+, 331 (100%) | 2% |
| 28 | 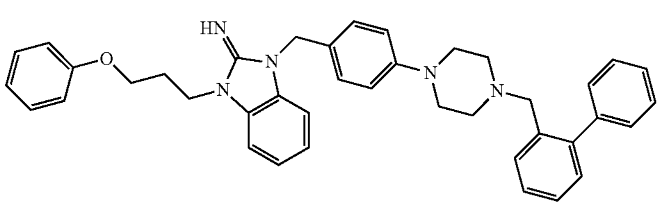 [SMILES: N=c1n(CCCOc2ccccc2)c2ccccc2n1Cc1ccc(N2CCN(Cc3ccccc3-c3ccccc3)CC2)cc1] | 1-[4-(4-Biphenyl-2-ylmethyl-piperazin-1-yl)-benzyl]-3-(3-phenoxy-propyl)-1,3-dihydro-benzoimidazol-2-ylideneamine | 608 [M + 1]+, 305 (100%) | 9% |

TABLE 9-continued

| Cpd | Structure | Name | HPLC-MS | Yield |
|---|---|---|---|---|
| 29 | 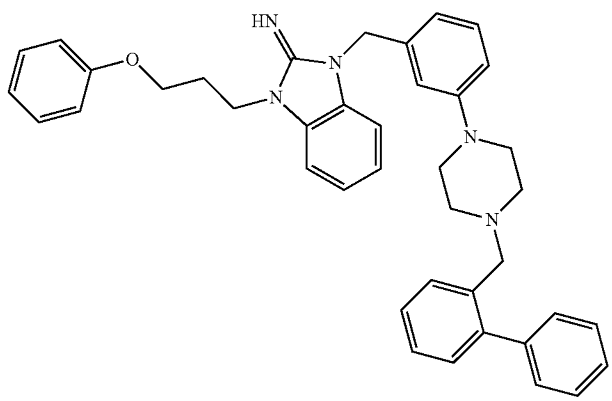 [SMILES: N=c1n(CCCOc2ccccc2)c2ccccc2n1Cc1cccc(N2CCN(Cc3ccccc3-c3ccccc3)CC2)c1] | 1-[3-(4-Biphenyl-2-ylmethyl-piperazin-1-yl)-benzyl]-3-(3-phenoxy-propyl)-1,3-dihydro-benzoimidazol-2-ylideneamine | 608 [M + 1]$^+$, 305 (100%) | 14% |
| 30 | 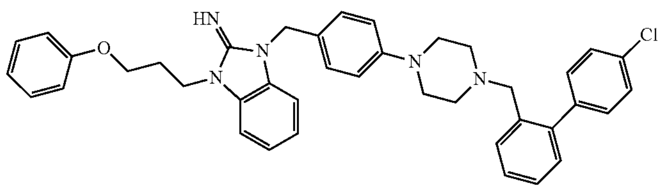 [SMILES: N=c1n(CCCOc2ccccc2)c2ccccc2n1Cc1ccc(N2CCN(Cc3ccccc3-c3ccc(Cl)cc3)CC2)cc1] | 1-{4-[4-(4'-Chloro-biphenyl-2-ylmethyl)-piperazin-1-yl]-benzyl}-3-(3-phenoxy-propyl)-1,3-dihydro-benzoimidazol-2-ylideneamine | 642 [M + 1]$^+$, 322 (100%) | 8% |
| 31 | 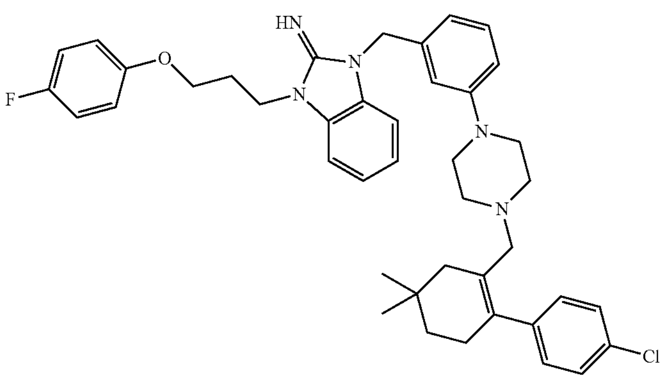 [SMILES: CC1(C)CCC(c2ccc(Cl)cc2)=C(CN2CCN(c3cccc(Cn4c(=N)n(CCCOc5ccc(F)cc5)c5ccccc54)c3)CC2)C1] | 1-(3-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine | 692 [M + 1]$^+$, 347 (100%) | 10% |
| 32 | 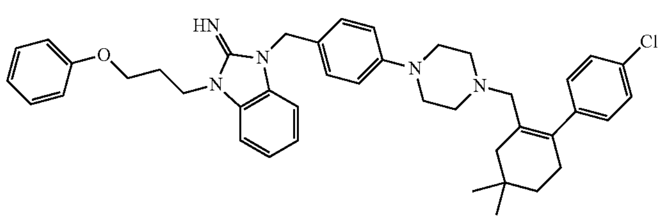 [SMILES: CC1(C)CCC(c2ccc(Cl)cc2)=C(CN2CCN(c3ccc(Cn4c(=N)n(CCCOc5ccccc5)c5ccccc54)cc3)CC2)C1] | 1-(4-{4-[2-(4-Chloro-phenyl)-5,5-dimethyl-cyclohex-1-enylmethyl]-piperazin-1-yl}-benzyl)-3-(3-phenoxy-propyl)-1,3-dihydro-benzoimidazol-2-ylideneamine | 674 [M + 1]$^+$, 338 (100%) | 2% |
| 33 | 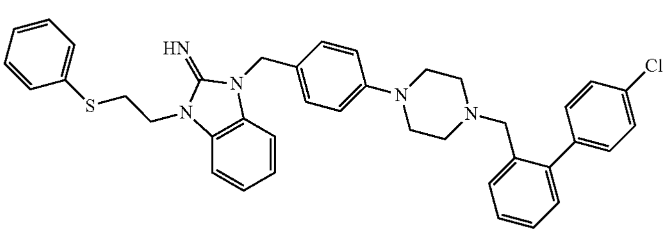 [SMILES: N=c1n(CCSc2ccccc2)c2ccccc2n1Cc1ccc(N2CCN(Cc3ccccc3-c3ccc(Cl)cc3)CC2)cc1] | 1-{4-[4-(4'-Chloro-biphenyl-2-ylmethyl)-piperazin-1-yl]-benzyl}-3-(2-phenylsulfanyl-ethyl)-1,3-dihydro-benzoimidazol-2-ylideneamine | 644 [M + 1]$^+$ | 22% |

Example 6

Synthesis of 1-[2-(4-biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine (Compound 35)

The title compound was prepared according to Scheme 6.

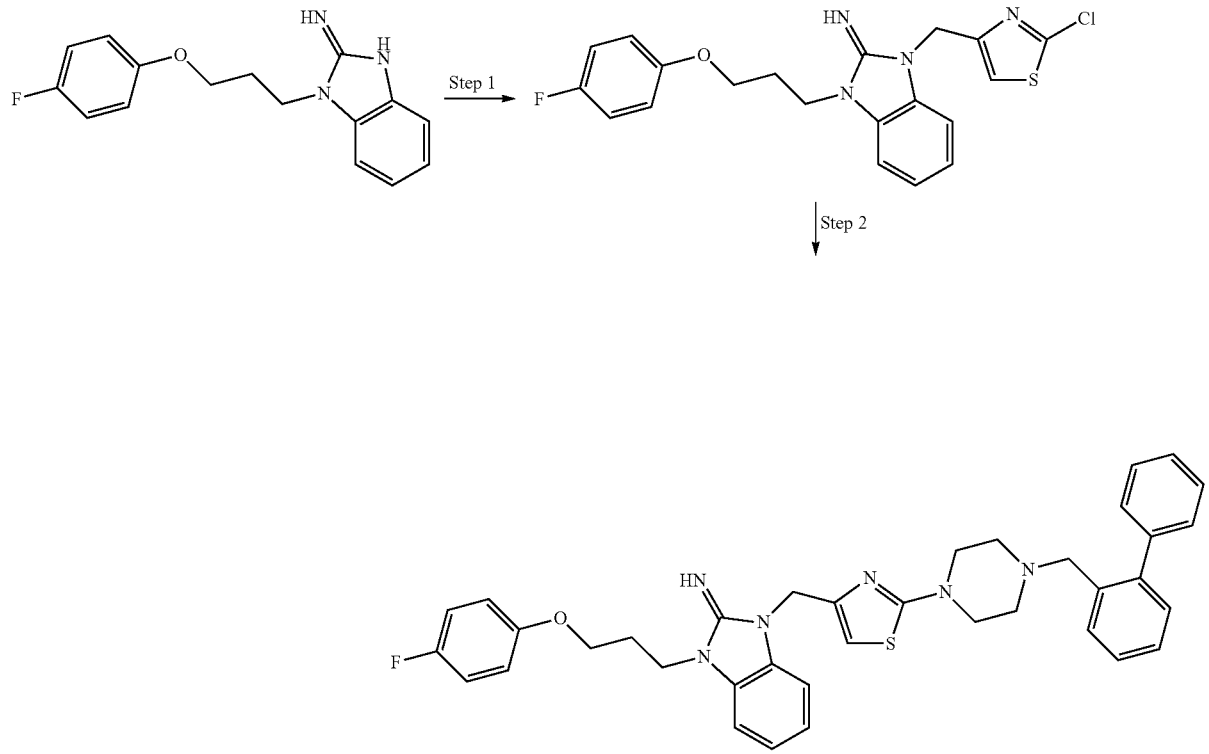

Step 1 Synthesis of 1-(2-chloro-thiazol-4-ylmethyl)-3-[3-(4-fluoro-phenoxy)-propyl]-1,3-dihydro-benzoimidazol-2-ylideneamine (Compound 34)

To a solution of 1-[3-(4-fluoro-phenoxy)-propyl]-1,3-dihydro-benzoimidazol-2-ylideneamine (2.89 g, 10.1 mmol) in 2-butanone (58 ml) at rt was added 2-chloro-4-chloromethyl-thiazole (2.55 g, 15.2 mmol) followed by potassium bromide (1.20 g, 10.1 mmol). The reaction mixture was heated to 95° C. where it was maintained for 32 h. After this time, the reaction was cooled to rt and additional potassium bromide (0.30 g, 2.52 mmol) was introduced. The reaction was stirred for a further 22 h at 90° C. and then it was cooled to rt and filtered. The collected solid was partitioned between dichloromethane and a saturated solution of NaHCO$_3$ (50 ml) and the organic layer was separated. The aqueous phase was extracted with additional dichloromethane (×1) and the combined organic fractions were washed with H$_2$O, brine, dried (Na$_2$SO$_4$), filtered and concentrated under reduced pressure to give 1-(2-chloro-thiazol-4-ylmethyl)-3-[3-(4-fluoro-phenoxy)-propyl]-1,3-dihydro-benzoimidazol-2-ylideneamine as a brown oil (2.57 g, 61%). HPLC-MS 417 [M+1]$^+$.

Step 2 Synthesis of 1-[2-(4-biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine (Compound 35)

To a solution of 1-(2-chloro-thiazol-4-ylmethyl)-3-[3-(4-fluoro-phenoxy)-propyl]-1,3-dihydro-benzoimidazol-2-ylideneamine (30 mg, 0.072 mmol) in N-methylpyrrolidinone (2 ml) was added 1-biphenyl-2-ylmethyl-piperazine (18 mg, 0.072 mmol), CuI (14 mg, 0.072 mmol) and K$_2$CO$_3$ (15 mg, 0.11 mmol). The reaction was heated in a microwave at 190° C. for a total of 1.5 h. After this time, the suspension was cooled to rt and filtered through Celite®. The collected solids were washed with dichloromethane and then the combined filtrate and washings were washed with H$_2$O. The aqueous phase was extracted with additional dichloromethane and the combined organic fractions were then washed with brine, dried (Na$_2$SO$_4$) and filtered. The filtrate was concentrated under reduced pressure and the crude product was purified by preparative HPLC. The product was free-based by partitioning between a saturated solution of NaHCO$_3$ and dichloromethane. The organic layer was then separated, dried (Na$_2$SO$_4$), filtered and concentrated under reduced pressure to give 1-[2-(4-biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine (3.6 mg, 8%). HPLC-MS 633 [M+1]$^+$, 317 (100%).

Using a similar procedure starting from 1-(2-chloro-thiazol-4-ylmethyl)-3-[3-(4-fluoro-phenoxy)-propyl]-1,3-dihydro-benzoimidazol-2-ylideneamine and the appropriate amine the compounds in Table 10 were prepared. The following modifications are noted:

Compound 36: Heated in the microwave for 1 h.
Compound 37: Catalytic CuI (0.07 equivalents) was used. Reaction was first heated to 120° C. for 16 h in a pressure tube and then heated in a microwave at 145° C. for 20 min.

TABLE 10

| Cpd | Structure | Name | HPLC-MS | Yield |
|---|---|---|---|---|
| 36 | 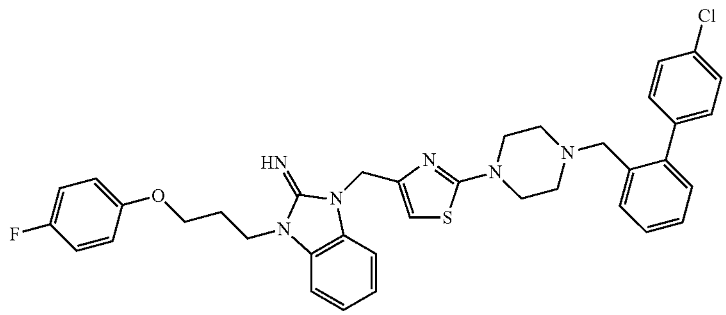 [SMILES: N=c1n(CCCOc2ccc(F)cc2)c2ccccc2n1Cc1csc(N2CCN(Cc3ccccc3-c3ccc(Cl)cc3)CC2)n1] | 1-{2-[4-(4'-Chloro-biphenyl-2-ylmethyl)-piperazin-1-yl]-thiazol-4-ylmethyl}-3-[3-(4-fluoro-phenoxy)-propyl]-1,3-dihydro-benzoimidazol-2-ylideneamine | 667 [M + 1]$^+$, 334 (100%) | 30% |
| 37 | 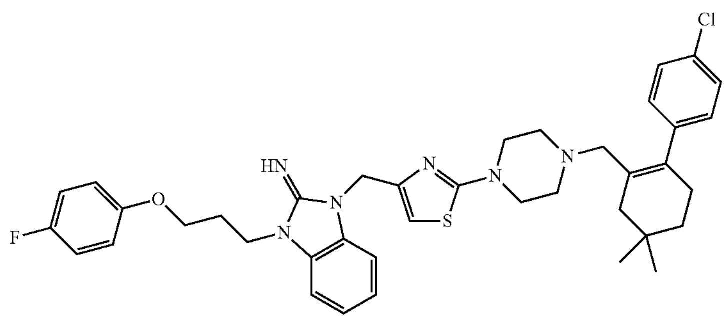 [SMILES: CC1(C)CCC(c2ccc(Cl)cc2)=C(CN2CCN(c3nc(Cn4c(=N)n(CCCOc5ccc(F)cc5)c5ccccc54)cs3)CC2)C1] | 1-(2-{4-[2-(4-Chloro-phenyl)-5,5-dimethyl-cyclohex-1-enylmethyl]-piperazin-1-yl}-thiazol-4-ylmethyl)-3-[3-(4-fluoro-phenoxy)-propyl]-1,3-dihydro-benzoimidazol-2-ylideneamine | 699 [M + 1]$^+$, 350 (100%) | 12% |

Example 7

Synthesis of 1-[2-(4-biphenyl-2-ylmethyl-piperazin-1-yl)-benzyl]-3-[3-(4-fluoro-phenoxy)-propyl]-1,3-dihydro-benzoimidazol-2-ylideneamine (Compound 38)

Preparation of the title compound was carried out according to Scheme 7.

Scheme 7

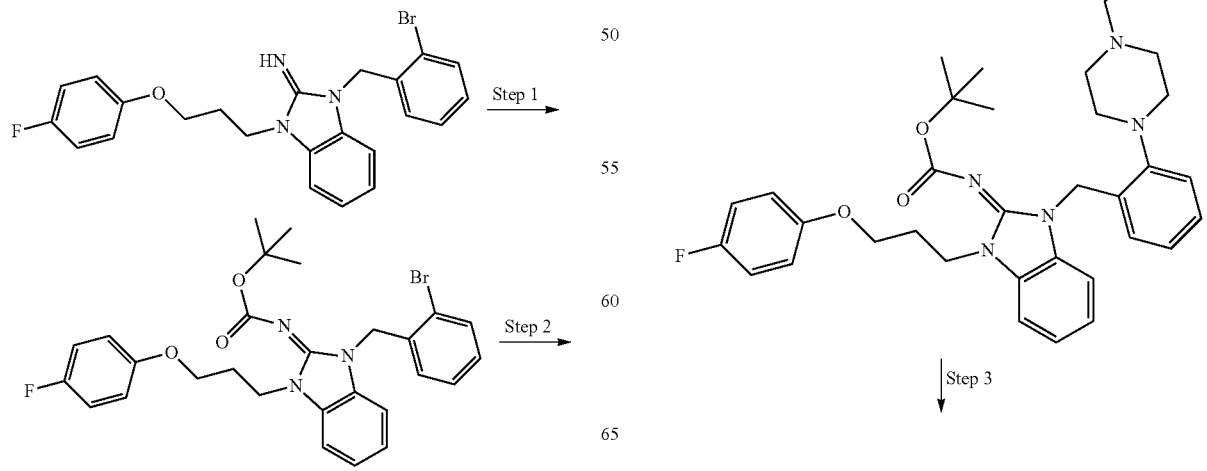

-continued

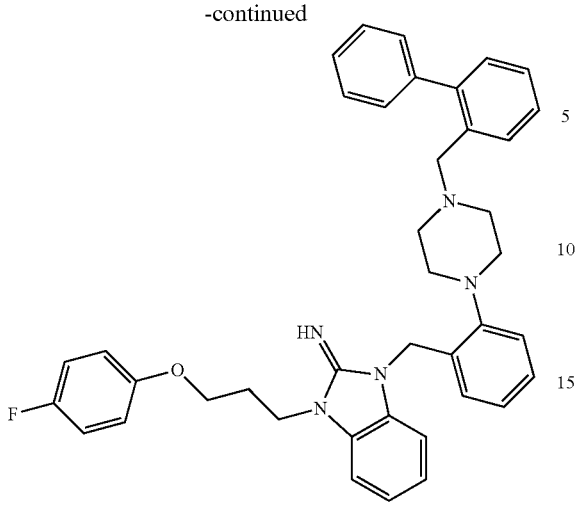

Step 1 Synthesis of [1-(2-bromo-benzyl)-3-[3-(4-fluoro-phenoxy)-propyl]-1,3-dihydro-benzoimidazol-ylidene]-carbamic acid tert-butyl ester To a solution of 1-(2-bromo-benzyl)-3-[3-(4-fluoro-phenoxy)-propyl]-1,3-dihydro-benzoimidazol-2-ylideneamine hydrobromide salt (480 mg, 1.05 mmol) in 1,4-dioxane (7.5 ml) and H$_2$O (7.5 ml) at rt was added Na$_2$CO$_3$ (280 mg, 2.64 mmol) followed by di-tert-butyl dicarbonate (0.39 g, 1.79 mmol). The reaction was stirred for 2.5 h at 40° C. and then warmed to 80° C. The reaction was cooled to rt, concentrated under reduced pressure and then purified by chromatography on silica eluting with 30% EtOAc/hexane to give [1-(2-bromo-benzyl)-3-[3-(4-fluoro-phenoxy)-propyl]-1,3-dihydro-benzoimidazol-ylidene]-carbamic acid tert-butyl ester (200 mg, 34%). HPLC-MS 554, 556 [M+1]$^+$.

Step 2 Synthesis of [1-[2-(4-biphenyl-2-ylmethyl-piperazin-1-yl)-benzyl]-3-[3-(4-fluoro-phenoxy)-propyl]-1,3-dihydro-benzoimidazol-ylidene]-carbamic acid tert-butyl ester To a degassed solution of [1-(2-bromo-benzyl)-3-[3-(4-fluoro-phenoxy)-propyl]-1,3-dihydro-benzoimidazol-ylidene]-carbamic acid tert-butyl ester (200 mg, 0.36 mmol) in anhydrous toluene (4 ml) was added Pd(OAc)$_2$ (0.7 mg, 1.8 □mol). Nitrogen was bubbled through the suspension for 10 min before BINAP (17 mg, 27 □mol) was added. After a further 2 min 1-biphenyl-2-ylmethyl-piperazine (99 mg, 0.36 mmol) in degassed toluene (4 ml) was introduced and then after a additional 2 min Cs$_2$CO$_3$ (0.86 g, 2.6 mmol) was added and the reaction was stirred for 2 min. Throughout all of the additions nitrogen was continuously bubbled through the reaction mixture. To After 2.75 h the reaction was cooled to rt and filtered through Celite®. Purification by chromatography on silica gave [1-[2-(4-biphenyl-2-ylmethyl-piperazin-1-yl)-benzyl]-3-[3-(4-fluoro-phenoxy)-propyl]-1,3-dihydro-benzoimidazol-ylidene]-carbamic acid tert-butyl ester (100 mg) which was used without purification in the next step.

Step 3 Synthesis of 1-[2-(4-biphenyl-2-ylmethyl-piperazin-1-yl)-benzyl]-3-[3-(4-fluoro-phenoxy)-propyl]-1,3-dihydro-benzoimidazol-2-ylideneamine (Compound 38)

To [1-[2-(4-biphenyl-2-ylmethyl-piperazin-1-yl)-benzyl]-3-[3-(4-fluoro-phenoxy)-propyl]-1,3-dihydro-benzoimidazol-ylidene]-carbamic acid tert-butyl ester (100 mg, 0.14 mmol) at rt was added 25% TFA in dichloromethane (5 ml). The reaction was stirred for 1 h and then concentrated under reduced pressure. The crude product was purified by preparative HPLC and then partitioned between saturated NaHCO$_3$ and dichloromethane. The organic phase was separated, washed with H$_2$O, dried (Na$_2$SO$_4$), filtered and concentrated under reduced pressure to provide 1-[2-(4-biphenyl-2-ylmethyl-piperazin-1-yl)-benzyl]-3-[3-(4-fluoro-phenoxy)-propyl]-1,3-dihydro-benzoimidazol-2-ylideneamine (2.8 mg, 3%). HPLC-MS 626 [M+1]$^+$, 324.

Example 8

Synthesis of 1-{4-[4-(4-chloro-benzyl)-piperazin-1-ylmethyl]-benzyl}-3-[3-(4-fluoro-phenoxy)-propyl]-1,3-dihydro-benzoimidazol-2-ylideneamine (Compound 39)

The title compound was synthesised as shown in Scheme 8.

Scheme 8

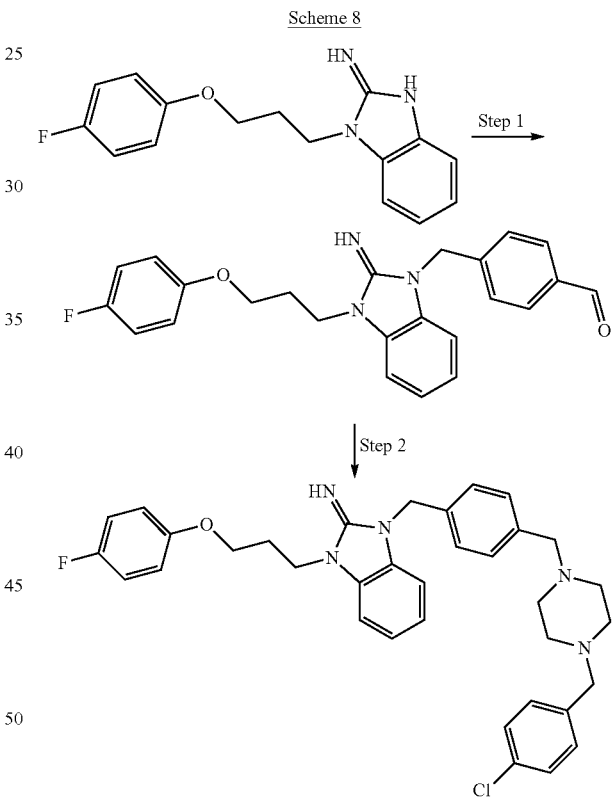

Step 1 Synthesis of 4-{3-[3-(4-fluoro-phenoxy)-propyl]-2-imino-2,3-dihydro-benzoimidazol-1-ylmethyl}-benzaldehyde To a solution of 1-[3-(4-fluoro-phenoxy)-propyl]-1,3-dihydro-benzoimidazol-2-ylideneamine (0.96 g, 3.36 mmol) in 2-butanone (50 ml) was added 4-bromomethyl benzaldehyde (1.0 g, 5.03 mmol). The reaction was heated to reflux where it was maintained for 48 h. After this time, the suspension was cooled to rt and filtered. The collected solid was washed with additional 2-butanone and then dried to provide 4-{3-[3-(4-fluoro-phenoxy)-propyl]-2-imino-2,3-dihydro-benzoimidazol-1-ylmethyl}-benzaldehyde hydrobromide salt (0.80 g, 49%) as a yellow solid which was used without further purification. HPLC-MS 404 [M+1]+.

Step 2 Synthesis of 1-{4-[4-(4-chloro-benzyl)-piperazin-1-ylmethyl]-benzyl}-3-[3-(4-fluoro-phenoxy)-propyl]-1,3-dihydro-benzoimidazol-2-ylideneamine (Compound 39)

To a solution of 1-(4-chloro-benzyl)-piperazine (70 mg, 0.33 mmol) in THF (10 ml) was added 4-{3-[3-(4-fluoro-phenoxy)-propyl]-2-imino-2,3-dihydro-benzoimidazol-1-ylmethyl}-benzaldehyde, hydrobromide salt (0.20 g, 0.41 mmol), sodium cyanoborohydride (31 mg, 0.49 mmol), H$_2$O (1 drop) and glacial acetic acid (0.068 ml). The reaction was warmed to 55° C. where it was maintained for 6 h. After this time, the mixture was cooled to rt and stirred for 16 h. The mixture was concentrated under reduced pressure and then partitioned between 1N HCl and EtOAc. The organic layer was removed and the aqueous phase was made basic using 10% K$_2$CO$_3$. The basic aqueous phase was extracted with EtOAc. The organic layer was dried (Na$_2$SO$_4$), filtered and concentrated under reduced pressure. Purification by chromatography on silica eluting with MeOH/dichloromethane provided 1-{4-[4-(4-chloro-benzyl)-piperazin-1-ylmethyl]-benzyl}-3-[3-(4-fluoro-phenoxy)-propyl]-1,3-dihydro-benzoimidazol-2-ylideneamine (23 mg, 11%). HPLC-MS 598 [M+1]+, 300.

Using a similar procedure starting from 4-{3-[3-(4-fluoro-phenoxy)-propyl]-2-imino-2,3-dihydro-benzoimidazol-1-ylmethyl}-benzaldehyde and using the appropriate amine the compounds in Table 11 were prepared.

TABLE 11

| Cpd | Structure | Name | HPLC-MS | Yield |
|---|---|---|---|---|
| 40 | 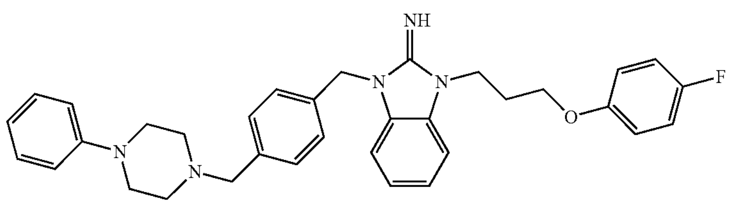 [SMILES: N=c1n(CCCOc2ccc(F)cc2)c2ccccc2n1Cc1ccc(CN2CCN(c3ccccc3)CC2)cc1] | 1-[3-(4-Fluoro-phenoxy)-propyl]-3-[4-(4-phenyl-piperazin-1-ylmethyl)-benzyl]-1,3-dihydro-benzoimidazol-2-ylideneamine | 550 [M + 1]+, 276 | 16% |
| 41 | 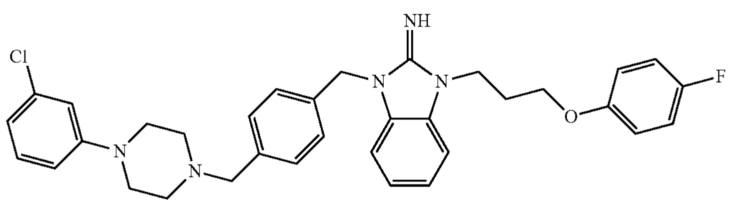 | 1-{4-[4-(3-Chloro-phenyl)-piperazin-1-ylmethyl]-benzyl}-3-[3-(4-fluoro-phenoxy)-propyl]-1,3-dihydro-benzoimidazol-2-ylideneamine | 584 [M + 1]+, 293 | 9% |
| 42 | 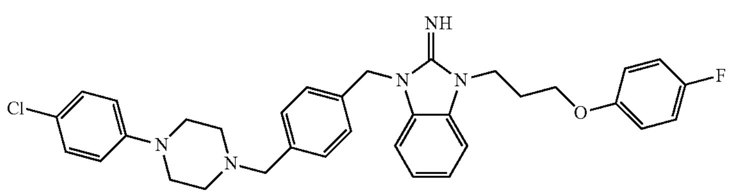 [SMILES: N=c1n(CCCOc2ccc(F)cc2)c2ccccc2n1Cc1ccc(CN2CCN(c3ccc(Cl)cc3)CC2)cc1] | 1-{4-[4-(4-Chloro-phenyl)-piperazin-1-ylmethyl]-benzyl}-3-[3-(4-fluoro-phenoxy)-propyl]-1,3-dihydro-benzoimidazol-2-ylideneamine | 584 [M + 1]+, 292 | 8% |
| 43 | 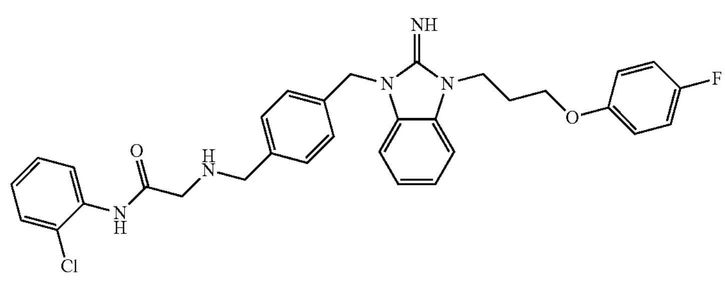 [SMILES: N=c1n(CCCOc2ccc(F)cc2)c2ccccc2n1Cc1ccc(CNCC(=O)Nc2ccccc2Cl)cc1] | N-(2-Chloro-phenyl)-2-(4-{3-[3-(4-fluoro-phenoxy)-propyl]-2-imino-2,3-dihydro-benzoimidazol-1-ylmethyl}-benzylamino)-acetamide | 572 [M + 1]+, 287 | 23% |
| 44 | 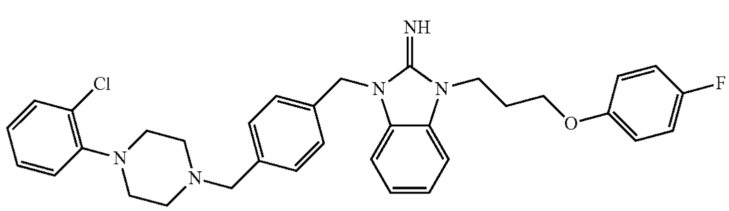 [SMILES: N=c1n(CCCOc2ccc(F)cc2)c2ccccc2n1Cc1ccc(CN2CCN(c3ccccc3Cl)CC2)cc1] | 1-{4-[4-(2-Chloro-phenyl)-piperazin-1-ylmethyl]-benzyl}-3-[3-(4-fluoro-phenoxy)-propyl]-1,3-dihydro-benzoimidazol-2-ylideneamine | 584 [M + 1]+, 293 | 14% |

TABLE 11-continued

| Cpd | Structure | Name | HPLC-MS | Yield |
|---|---|---|---|---|
| 45 | 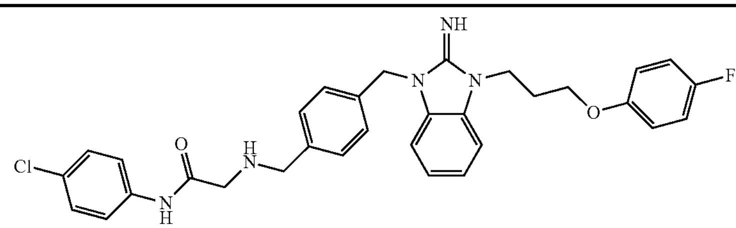 | N-(4-Chloro-phenyl)-2-(4-{3-[3-(4-fluoro-phenoxy)-propyl]-2-imino-2,3-dihydro-benzoimidazol-1-ylmethyl}-benzylamino)-acetamide | 572 [M + 1]+, 286 | 17% |
| 46 | 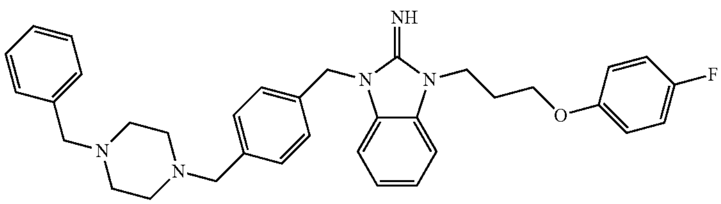 [SMILES: N=c1n(CCCOc2ccc(F)cc2)c2ccccc2n1Cc1ccc(CN2CCN(Cc3ccccc3)CC2)cc1] | 1-[4-(4-Benzyl-piperazin-1-ylmethyl)-benzyl]-3-[3-(4-fluoro-phenoxy)-propyl]-1,3-dihydro-benzoimidazol-2-ylideneamine | 564 [M + 1]+, 283. | 10% |
| 47 | 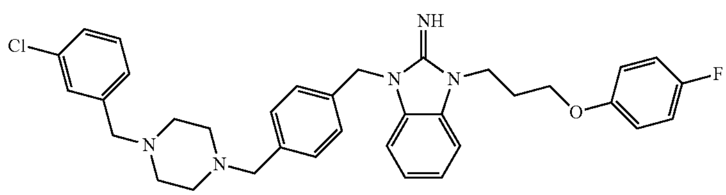 [SMILES: N=c1n(CCCOc2ccc(F)cc2)c2ccccc2n1Cc1ccc(CN2CCN(Cc3cccc(Cl)c3)CC2)cc1] | 1-{4-[4-(3-Chloro-benzyl)-piperazin-1-ylmethyl]-benzyl}-3-[3-(4-fluoro-phenoxy)-propyl]-1,3-dihydro-benzoimidazol-2-ylideneamine | 598 [M + 1]+, 300. | 14% |

Example 9

Synthesis of 1-{4-[4-(2-chloro-benzyl)-piperazin-1-ylmethyl]-benzyl}-3-[3-(4-fluoro-phenoxy)-propyl]-1,3-dihydro-benzoimidazol-2-ylideneamine (Compound 48)

Compound 48 was synthesised by the method shown in Scheme 9.

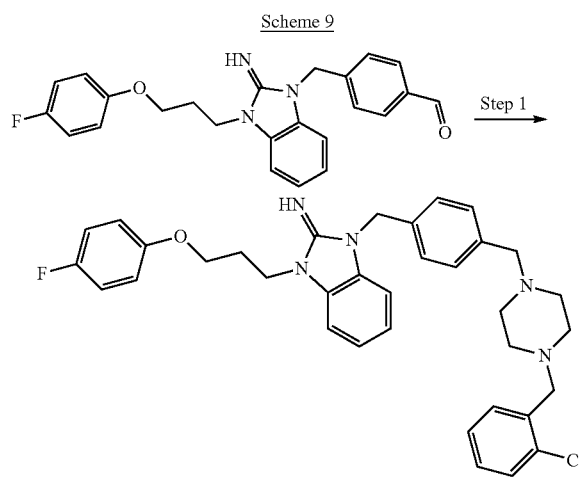

Scheme 9

Step 1 Synthesis of 1-{4-[4-(2-chloro-benzyl)-piperazin-1-ylmethyl]-benzyl}-3-[3-(4-fluoro-phenoxy)-propyl]-1,3-dihydro-benzoimidazol-2-ylideneamine (Compound 48)

To a mixture of 4-{3-[3-(4-fluoro-phenoxy)-propyl]-2-imino-2,3-dihydro-benzoimidazol-1-ylmethyl}-benzaldehyde, hydrobromide salt (0.39 g, 0.81 mmol) and sodium triacetoxyborohydride (0.322 g, 1.52 mmol) in 1,2-dichloroethane (5 ml) at rt was added 1-(2-chloro-benzyl)-piperazine (0.20 g, 0.95 mmol). The reaction was stirred for 8 h and then washed with a saturated solution of NaHCO$_3$, H$_2$O, dried (Na$_2$SO$_4$), filtered and concentrated under reduced pressure. Purification by chromatography provided 1-{4-[4-(2-chloro-benzyl)-piperazin-1-ylmethyl]-benzyl}-3-[3-(4-fluoro-phenoxy)-propyl]-1,3-dihydro-benzoimidazol-2-ylideneamine (90 mg, 19%). HPLC-MS 598 [M+1]+, 300.

Using a similar procedure starting from 4-{3-[3-(4-fluoro-phenoxy)-propyl]-2-imino-2,3-dihydro-benzoimidazol-1-ylmethyl}-benzaldehyde and using the appropriate amine the compound in Table 12 was prepared.

TABLE 12

| Cpd | Structure | Name | HPLC-MS | Yield |
|---|---|---|---|---|
| 49 | 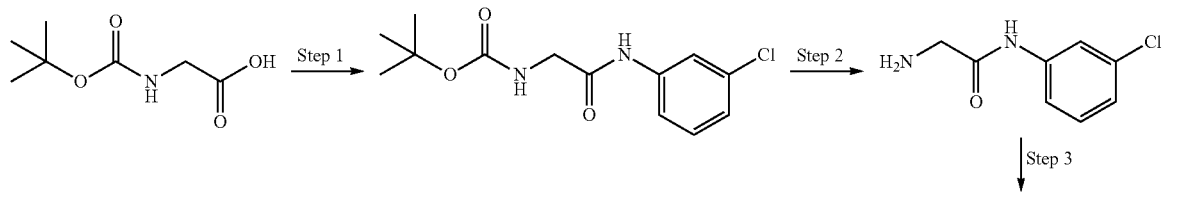 | 1-[4-(4-Biphenyl-2-ylmethyl-piperazin-1-ylmethyl)-benzyl]-3-[3-(4-fluoro-phenoxy)-propyl]-1,3-dihydro-benzoimidazol-2-ylideneamine | 640 [M + 1]$^+$, 320 | 9% |

Example 10

Synthesis of N-(3-chloro-phenyl)-2-(4-{3-[3-(4-fluoro-phenoxy)-propyl]-2-imino-2,3-dihydro-benzoimidazol-1-ylmethyl}-benzylamino)-acetamide (Compound 50)

The title compound was prepared according to Scheme 10 was added 3-chloroaniline (0.43 g, 3.42 mmol), HOBt (0.58 g, 4.28 mmol), EDC (1.10 g, 5.7 mmol) and N-methyl morpholine (0.43 g, 4.28 mmol). The reaction was stirred for 5 h and then washed with 1M KHSO$_4$, 10% NaHCO$_3$ solution and brine. The organic phase was separated, dried (Na$_2$SO$_4$), filtered and concentrated under reduced pres- Scheme 10

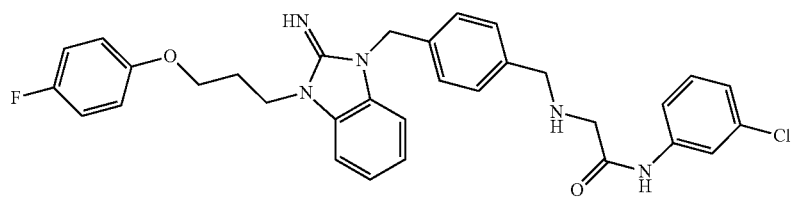

Step 1 Synthesis of [(3-chloro-phenylcarbamoyl)-methyl]-carbamic acid tert-butyl ester To a solution of N-tert-butoxycarbonyl glycine (0.5 g, 2.85 mmol) in dichloromethane (25 ml) at rt sure to give [(3-chloro-phenylcarbamoyl)-methyl]-carbamic acid tert-butyl ester (0.7 g, 86%). HPLC-MS 284, 286 [M+1]$^+$.

Using a similar procedure starting from N-tert-butoxycarbonyl glycine and the appropriate aniline the compound in Table 13 was prepared.

TABLE 13

| Structure | Name | HPLC-MS | Yield |
|---|---|---|---|
| 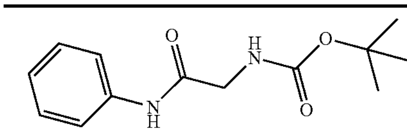 | Phenylcarbamoylmethyl-carbamic acid tert-butyl ester | 251 [M + 1]$^+$ | 84% |

Step 2 Synthesis of
2-amino-N-(3-chloro-phenyl)-acetamide

To [(3-chloro-phenylcarbamoyl)-methyl]-carbamic acid tert-butyl ester (0.7 g, 2.46 mmol) at rt was added 1,4-dioxane HCl (10 ml). The reaction was stirred for 16 h at rt and then filtered. The collected solid was 2-amino-N-(3-chloro-phenyl)-acetamide hydrochloride salt (0.6 g, 100%). HPLC-MS 184, 186 [M+1]$^+$.

Using a similar procedure the compound in Table 14 was prepared.

TABLE 14

| Structure | Name | HPLC-MS | Yield |
|---|---|---|---|
| (structure) | 2-Amino-N-phenyl-acetamide | 151 [M + 1]$^+$ | 13% |

Step 3 Synthesis of N-(3-chloro-phenyl)-2-(4-{3-[3-(4-fluoro-phenoxy)-propyl]-2-imino-2,3-dihydro-benzoimidazol-1-ylmethyl}-benzylamino)-acetamide (Compound 50)

A solution of 4-{3-[3-(4-fluoro-phenoxy)-propyl]-2-imino-2,3-dihydro-benzoimidazol-1-ylmethyl}-benzaldehyde, hydrobromide salt (0.25 g, 0.52 mmol), 2-amino-N-(4-chloro-phenyl)-acetamide (114 mg, 0.62 mmol) and sodium triacetoxyborohydride (0.183 g, 0.87 mmol) in 1,2-dichloroethane (25 ml) was stirred at 0° C. and then slowly warmed to rt where it was maintained for 16 h. After this time a saturated solution of KHSO$_4$ was introduced and the suspension was filtered. The collected solid was washed with MeOH and H$_2$O and then dried to provide N-(3-chloro-phenyl)-2-(4-{3-[3-(4-fluoro-phenoxy)-propyl]-2-imino-2,3-dihydro-benzoimidazol-1-ylmethyl}-benzylamino)-acetamide (50 mg, 17%). HPLC-MS 572 [M+1]$^+$, 287.

Using a similar procedure starting from 4-{3-[3-(4-fluoro-phenoxy)-propyl]-2-imino-2,3-dihydro-benzoimidazol-1-ylmethyl}-benzaldehyde and the appropriate amine the compound in Table 15 was prepared. The following modifications are noted:

Compound 51—Purification was performed by chromatography on silica (washed with triethylamine) eluting with MeOH/EtOAc. The purified product was converted into the HCl salt using HCl in 1,4-dioxane.

TABLE 15

| Cpd | Structure | Name | HPLC-MS | Yield |
|---|---|---|---|---|
| 51 | (structure) | 2-(4-{3-[3-(4-Fluoro-phenoxy)-propyl]-2-imino-2,3-dihydro-benzoimidazol-1-ylmethyl}-benzylamino)-N-phenyl-acetamide | 538 [M + 1]$^+$, 270 | 23% |

Example 11

Synthesis of 1-[6-(4-benzyl-piperazin-1-yl)-pyridin-3-ylmethyl]-3-[3-(4-fluoro-phenoxy)-propyl]-1,3-dihydro-benzoimidazol-2-ylideneamine (Compound 53)

Compound 53 was prepared according to Scheme 11.

Scheme 11

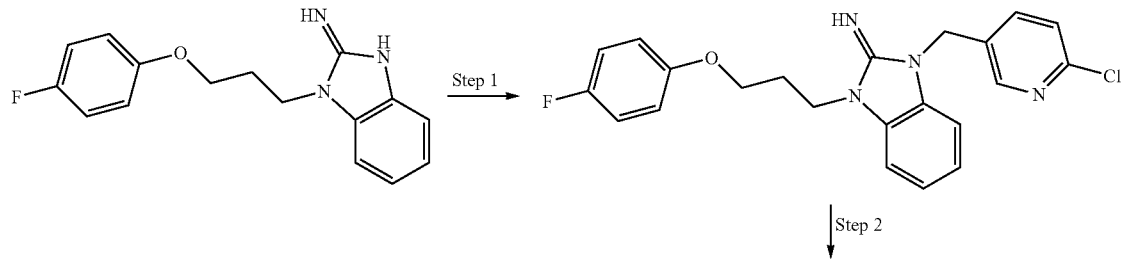

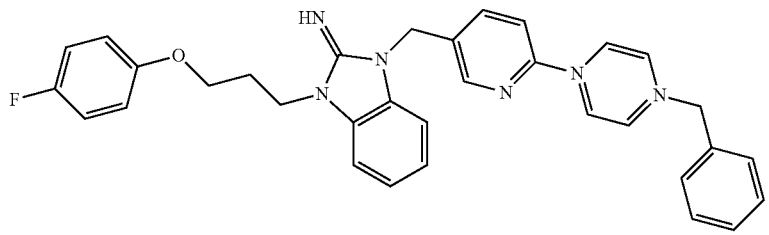

Step 1 Synthesis of 1-(6-chloro-pyridin-3-ylmethyl)-3-(3-phenoxy-propyl)-1,3-dihydro-benzoimidazol-2-ylideneamine (Compound 52)

To a solution of 1-[3-(4-fluoro-phenoxy)-propyl]-1,3-dihydro-benzoimidazol-2-ylideneamine (2.0 g, 7.01 mmol) in 2-butanone (25 ml) at rt was added 2-chloro-5-chloromethyl-pyridine (2.27 g, 14.0 mmol) followed by NaBr (0.715 g, 7.01 mmol). The reaction was heated to 90° C. where it was maintained for 4 d. After this time, the suspension was cooled to rt and filtered. The collected solid was washed with additional 2-butanone and then dried to give 1-(6-chloro-pyridin-3-yl-methyl)-3-(3-phenoxy-propyl)-1,3-dihydro-benzoimidazol-2-ylideneamine, hydrochloride salt (1.6 g, 51%) which was used without further purification. HPLC-MS 411, 413 [M+1]$^+$.

Step 2 Synthesis of 1-[6-(4-benzyl-piperazin-1-yl)-pyridin-3-ylmethyl]-3-[3-(4-fluoro-phenoxy)-propyl]-1,3-dihydro-benzoimidazol-2-ylideneamine (Compound 53)

To a degassed suspension of potassium t-butoxide (41 mg, 0.37 mmol), Pd(OAc)$_2$ (1 mg, 4.5 μmol) and triisobutyl phosphatrane (3 mg, 9.8 μmol) in toluene (5 ml) at rt was added 1-(6-chloro-pyridin-3-ylmethyl)-3-(3-phenoxy-propyl)-1,3-dihydro-benzoimidazol-2-ylideneamine, hydrochloride salt (100 mg, 0.22 mmol) and 1-benzyl-piperazine (52 μl, 0.29 mmol). The reaction flask was sealed under nitrogen and heated to 80° C. where it was maintained for 16 h. After this time the temperature was raised to 120° C. where it was left for a further 16 h. The mixture was then cooled to rt and concentrated under reduced pressure. Purification by chromatography on basic alumina eluting with EtOAc and then conversion to the hydrochloride salt provided 1-[6-(4-benzyl-piperazin-1-yl)-pyridin-3-ylmethyl]-3-[3-(4-fluoro-phenoxy)-propyl]-1,3-dihydro-benzoimidazol-2-ylideneamine, hydrochloride salt (35 mg, 27%). HPLC-MS 551 [M+1]$^+$, 276.

Using a similar procedure starting from 1-(6-chloro-pyridin-3-ylmethyl)-3-(3-phenoxy-propyl)-1,3-dihydro-benzoimidazol-2-ylideneamine and using the appropriate amine the compounds listed in Table 16 were prepared. The following modifications are noted:

Compounds 54-57 were not converted into the hydrochloride salt.

TABLE 16

| Cpd | Structure | Name | HPLC-MS | Yield |
|---|---|---|---|---|
| 54 | 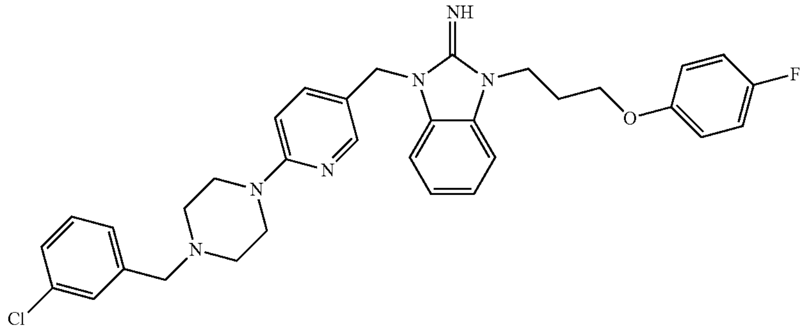 [SMILES: N=c1n(CCCOc2ccc(F)cc2)c2ccccc2n1Cc1ccc(N2CCN(Cc3cccc(Cl)c3)CC2)nc1] | 1-{6-[4-(3-Chloro-benzyl)-piperazin-1-yl]-pyridin-3-ylmethyl}-3-[3-(4-fluoro-phenoxy)-propyl]-1,3-dihydro-benzoimidazol-2-ylideneamine | 585 [M + 1]$^+$, 293 | 15% |
| 55 | 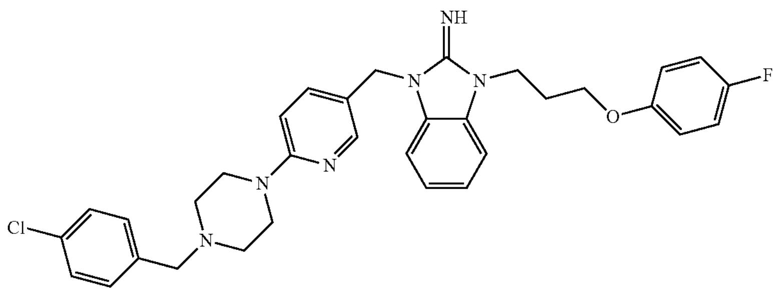 [SMILES: N=c1n(CCCOc2ccc(F)cc2)c2ccccc2n1Cc1ccc(N2CCN(Cc3ccc(Cl)cc3)CC2)nc1] | 1-{6-[4-(4-Chloro-benzyl)-piperazin-1-yl]-pyridin-3-ylmethyl}-3-[3-(4-fluoro-phenoxy)-propyl]-1,3-dihydro-benzoimidazol-2-ylideneamine | 585 [M + 1]$^+$, 293 | 17% |
| 56 | 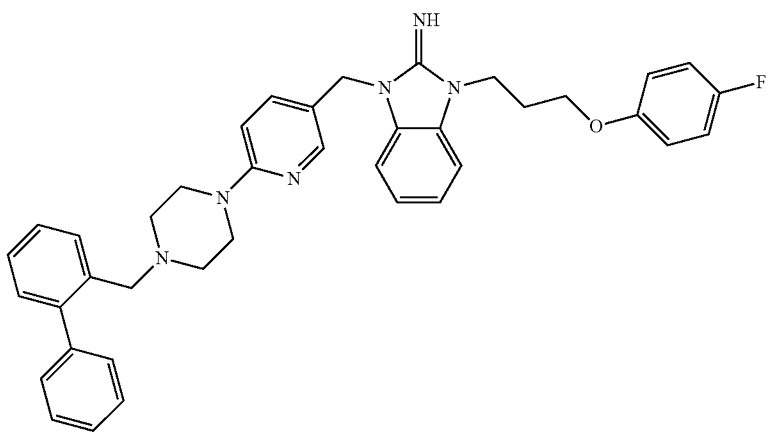 [SMILES: N=c1n(CCCOc2ccc(F)cc2)c2ccccc2n1Cc1ccc(N2CCN(Cc3ccccc3-c3ccccc3)CC2)nc1] | 1-[6-(4-Biphenyl-2-ylmethyl-piperazin-1-yl)-pyridin-3-ylmethyl]-3-(3-(4-fluoro-phenoxy)-propyl)-1,3-dihydro-benzoimidazol-2-ylideneamine | 627 [M + 1]$^+$, 314 | 29% |
| 57 | 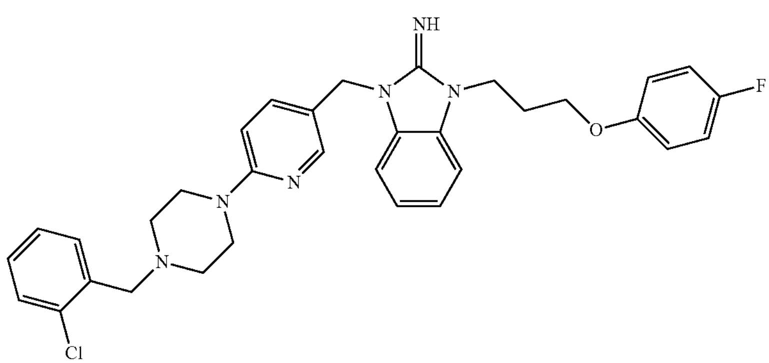 [SMILES: N=c1n(CCCOc2ccc(F)cc2)c2ccccc2n1Cc1ccc(N2CCN(Cc3ccccc3Cl)CC2)nc1] | 1-{6-[4-(2-Chloro-benzyl)-piperazin-1-yl]-pyridin-3-ylmethyl}-3-[3-(4-fluoro-phenoxy)-propyl]-1,3-dihydro-benzoimidazol-2-ylideneamine | 585 [M + 1]$^+$, 293 | 8% |

Example 12

Synthesis of 3-[4-(4-biphenyl-2-ylmethyl-piperazin-1-yl)-benzyl]-1-[3-(4-fluoro-phenoxy)-propyl]-5-methyl-1,3-dihydro-benzoimidazol-2-ylideneamine (Compound 62)

Scheme 12 shows the route used to obtain the title compound.

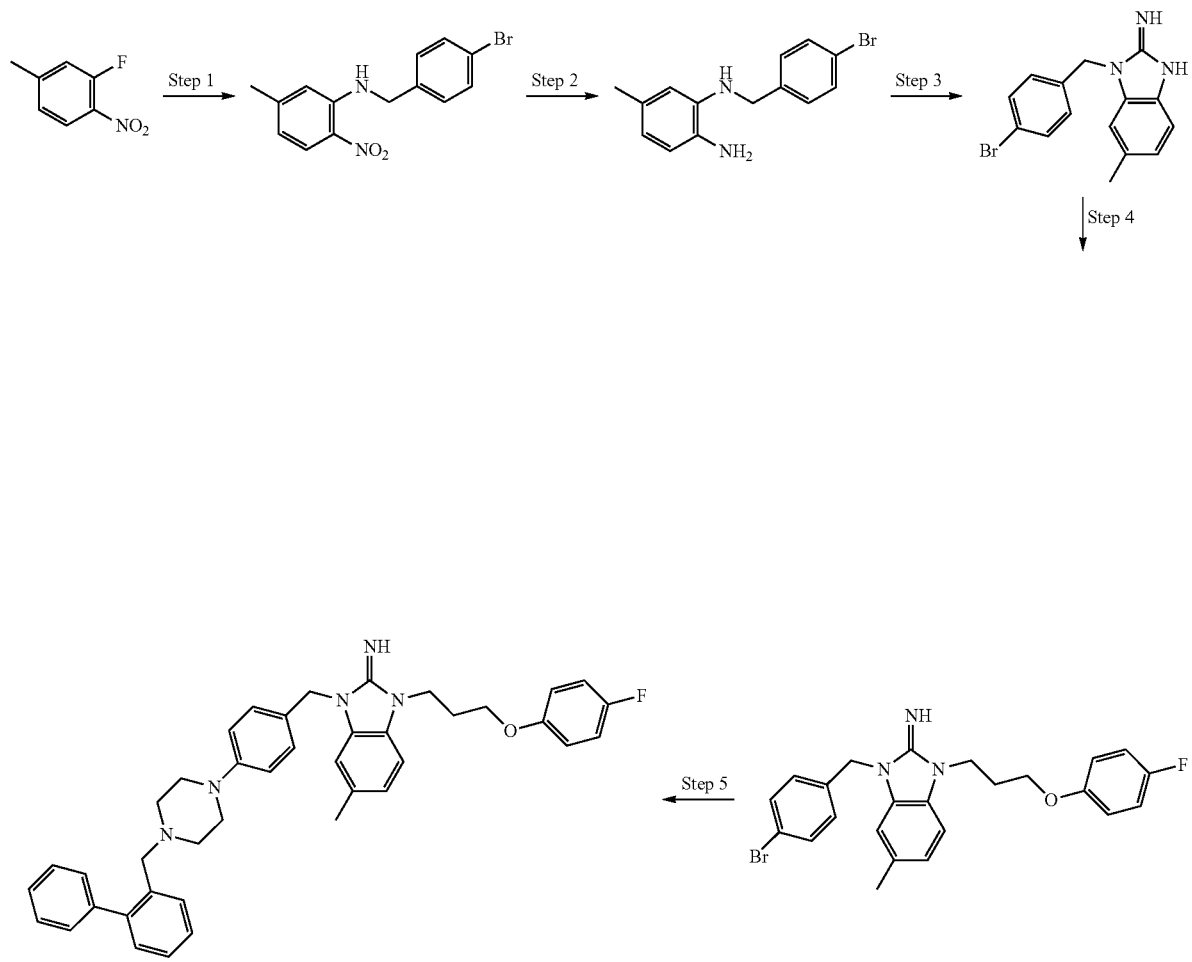

Scheme 12

Step 1 Synthesis of (4-bromo-benzyl)-(5-methyl-2-nitro-phenyl)-amine

To a solution of 3-fluoro-4-nitrotoluene (0.30 g, 1.93 mmol) in EtOH (18 ml) at rt under nitrogen was added 4-bromobenzylamine (0.36 g, 1.93 mmol) slowly. The reaction was warmed to reflux where it was maintained for 2 d. After this time, the mixture was cooled to rt and concentrated under reduced pressure. The crude product was partitioned between $H_2O$ and EtOAc and the organic phase was separated, washed with 5N HCl, dried ($Na_2SO_4$) and concentrated under reduced pressure to provide (4-bromo-benzyl)-(5-methyl-2-nitro-phenyl)-amine (0.45 g, 72%) as a yellow solid.

Using a similar procedure on the appropriate fluoronitrobenzene starting material the compounds in Table 17 were prepared.

TABLE 17

| Structure | Name | Yield |
|---|---|---|
| 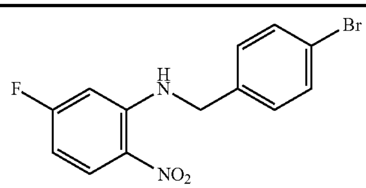 | (4-Bromo-benzyl)-(5-fluoro-2-nitro-phenyl)-amine | 90% |
| 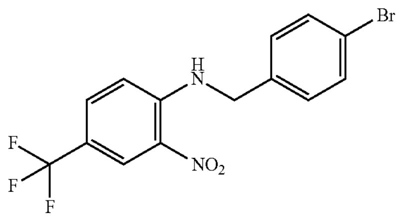 [SMILES: O=[N+]([O-])c1cc(C(F)(F)F)ccc1NCc1ccc(Br)cc1] | (4-Bromo-benzyl)-(2-nitro-4-trifluoromethyl-phenyl)-amine | 78% |
| 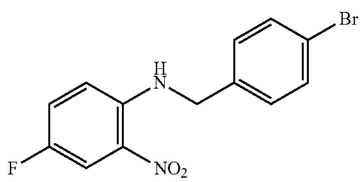 [SMILES: Nc1cc(F)ccc1NCc1ccc(Br)cc1] | (4-Bromo-benzyl)-(4-fluoro-2-nitro-phenyl)-amine | 65% |

Step 2 Synthesis of N-2-(4-bromo-benzyl)-4-methyl-benzene-1,2-diamine

Iron (3 g, 0.107 mol) and ammonium chloride (3.5 g, 0.065 mol) in t-butanol:water (5:2, 40 ml) were heated to reflux for 15 min. After this time, the temperature was lowered to 50° C. and (4-bromo-benzyl)-(5-methyl-2-nitro-phenyl)-amine (0.35 g, 1.09 mmol) in t-butanol (40 ml) was introduced in three portions over 10 min. After the addition the reaction was heated to reflux and then additional iron (3 g, 0.107 mol) and ammonium chloride (3.5 g, 0.065 mol) was introduced. The mixture was stirred for a further 1 h at reflux and then cooled to rt and concentrated under reduced pressure. The solid that remained was partitioned between EtOAc and $H_2O$ and the organic phase was separated. The aqueous layer was extracted with additional EtOAc and the combined organic fractions were washed with brine, dried ($Na_2SO_4$), filtered and concentrated under reduced pressure. Purification by column chromatography on silica eluting with EtOAc:hexanes (gradient elution from 2-16%) provided N-2-(4-bromo-benzyl)-4-methyl-benzene-1,2-diamine (183 mg, 58%). HPLC-MS 291, 293 [M+1]$^+$.

Using a similar procedure on the appropriate nitrobenzene starting material from Table 17 the compounds in Table 18 were prepared.

TABLE 18

| Structure | Name | Yield | HPLC-MS |
|---|---|---|---|
| 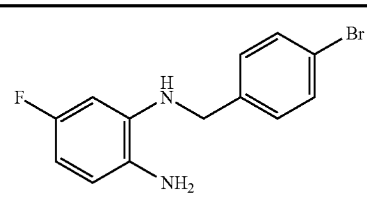 | N*2*-(4-Bromo-benzyl)-4-fluoro-benzene-1,2-diamine | 44% | 295, 297 [M + 1]$^+$ |
| 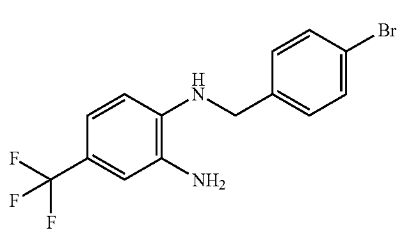 | N*1*-(4-Bromo-benzyl)-4-trifluoromethyl-benzene-1,2-diamine | 83% | 345, 347 [M + 1]$^+$ |

TABLE 18-continued

| Structure | Name | Yield | HPLC-MS |
|---|---|---|---|
| (structure: 4-fluoro-N1-(4-bromobenzyl)benzene-1,2-diamine) | N*1*-(4-Bromo-benzyl)-4-fluoro-benzene-1,2-diamine | 64% | 295, 297 [M + 1]+ |

Step 3 Synthesis of 1-(4-bromo-benzyl)-6-methyl-1,3-dihydro-benzoimidazol-2-ylideneamine To a solution of N-2-(4-bromo-benzyl)-4-methyl-benzene-1,2-diamine (0.20 g, 0.68 mmol) at rt in EtOH (10 ml) was added cyanogen bromide (0.21 g, 2.06 mmol). The reaction was stirred for 1 h at rt and then heated to reflux where it was maintained for 18 h. After this time, the mixture was concentrated under reduced pressure and the product that remained was partitioned between EtOAc and aqueous ammonia. The organic phase was separated, washed with brine, dried ($Na_2SO_4$), filtered and concentrated under reduced pressure. The solid that remained was triturated with hexanes and then the hexanes were removed and the product dried to give 1-(4-bromo-benzyl)-6-methyl-1,3-dihydro-benzoimidazol-2-ylideneamine (0.16 g, 74%) which was used without further purification. HPLC-MS 316, 318 [M+1]+.

Using a similar procedure on the appropriate diamines from Table 18 the compounds in Table 19 were prepared.

Step 4 Synthesis of 3-(4-bromo-benzyl)-1-[3-(4-fluoro-phenoxy)-propyl]-5-methyl-1,3-dihydro-benzoimidazol-2-ylideneamine (Compound 58)

To a solution of 1-(4-bromo-benzyl)-6-methyl-1,3-dihydro-benzoimidazol-2-ylideneamine (0.14 g, 0.44 mmol) in 2-butanone (5 ml) at rt was added 1-(3-bromo-propoxy)-4-fluoro-benzene (0.15 g, 0.66 mmol). The reaction was stirred for 10 min and then additional 2-butanone (5 ml) was introduced. The mixture was heated to reflux where it was maintained for 48 h. After this time, the reaction was cooled to rt and additional 1-(3-bromo-propoxy)-4-fluoro-benzene (0.05, 0.22 mmol) was added. The reaction was then heated to reflux for a further 15 h. It was then cooled to rt and filtered. The collected solid was dried to provide 3-(4-bromo-benzyl)-1-[3-(4-fluoro-phenoxy)-propyl]-5-methyl-1,3-dihydrobenzoimidazol-2-ylideneamine, hydrobromide salt (0.04 g, 16%). HPLC-MS 468, 470 [M+1]+.

TABLE 19

| Structure | Name | Yield | HPLC-MS |
|---|---|---|---|
| (structure) | 1-(4-Bromo-benzyl)-6-fluoro-1,3-dihydro-benzoimidazol-2-ylideneamine | 74% | 320, 322 [M + 1]+ |
| (structure) | 1-(4-Bromo-benzyl)-5-trifluoromethyl-1,3-dihydro-benzoimidazol-2-ylideneamine | 78% | 370, 372 [M + 1]+ |
| (structure) | 1-(4-Bromo-benzyl)-5-fluoro-1,3-dihydro-benzoimidazol-2-ylideneamine | 100% | 320, 322 [M + 1]+ |

Using a similar procedure with the intermediates from Table 19 and 4-bromobenzyl bromide the compounds in Table 20 were prepared.

TABLE 20

| Cpd | Structure | Name | Yield | HPLC-MS |
|---|---|---|---|---|
| 59 | 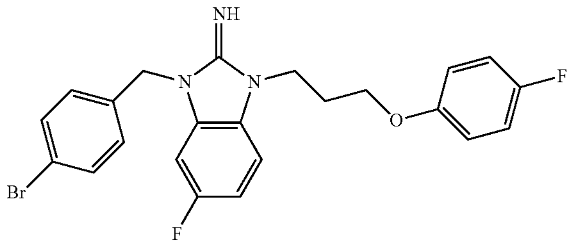 [SMILES: N=c1n(CCCOc2ccc(F)cc2)c2ccc(F)cc2n1Cc1ccc(Br)cc1] | 3-(4-Bromo-benzyl)-5-fluoro-1-[3-(4-fluoro-phenoxy)-propyl]-1,3-dihydro-benzoimidazol-2-ylideneamine | 44% | 472, 474 [M + 1]+ |
| 60 | 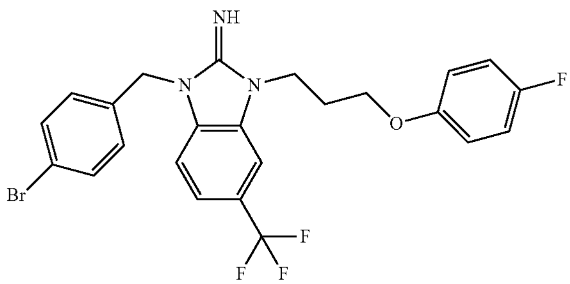 [SMILES: N=c1n(CCCOc2ccc(F)cc2)c2cc(C(F)(F)F)ccc2n1Cc1ccc(Br)cc1] | 1-(4-Bromo-benzyl)-3-[3-(4-fluoro-phenoxy)-propyl]-5-trifluoromethyl-1,3-dihydro-benzoimidazol-2-ylideneamine | 16% | 522, 524 [M + 1]+ |
| 61 | 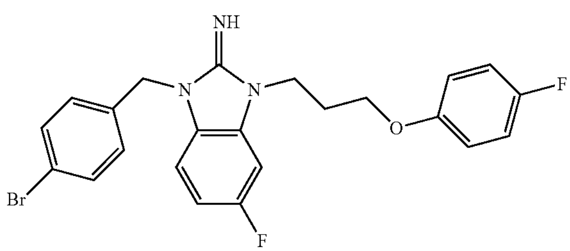 [SMILES: N=c1n(CCCOc2ccc(F)cc2)c2cc(F)ccc2n1Cc1ccc(Br)cc1] | 1-(4-Bromo-benzyl)-5-fluoro-3-[3-(4-fluoro-phenoxy)-propyl)-1,3-dihydro-benzoimidazol-2-ylideneamine | 24% | 472, 474 [M + 1]+ |

Step 5 Synthesis of 3-[4-(4-biphenyl-2-ylmethyl-piperazin-1-yl)-benzyl]-1-[3-(4-fluoro-phenoxy)-propyl]-5-methyl-1,3-dihydro-benzoimidazol-2-ylideneamine (Compound 62)

3-(4-Bromo-benzyl)-1-[3-(4-fluoro-phenoxy)-propyl]-5-methyl-1,3-dihydrobenzoimidazol-2-ylideneamine, hydrobromide salt (20 mg, 0.036 mmol) was partitioned between aqueous NaOH and EtOAc. The organic phase was separated, dried (Na₂SO₄) and concentrated under reduced pressure to provide 3-(4-bromo-benzyl)-1-[3-(4-fluoro-phenoxy)-propyl]-5-methyl-1,3-dihydrobenzoimidazol-2-ylideneamine (0.036 mmol). To a degassed solution of Pd(OAc)₂ (0.04 mg, 0.16 □mol) and BINAP (0.44 mg, 0.71 mmol) in toluene (8 ml) at 40° C. was added 1-biphenyl-2-ylmethyl-piperazine (18 mg, 0.071 mmol) followed by 3-(4-bromo-benzyl)-1-[3-(4-fluoro-phenoxy)-propyl]-5-methyl-1,3-dihydrobenzoimidazol-2-ylideneamine (0.036 mmol) and sodium t-butoxide (4.8 mg, 0.05 mmol). The suspension was then heated to 130° C. where it was maintained for 20 h. After this time, the mixture was filtered and then the filtrate was partitioned between H₂O and EtOAc. The organic phase was separated and concentrated under reduced pressure to provide the crude product. Purification by preparative HPLC gave 3-[4-(4-biphenyl-2-ylmethyl-piperazin-1-yl)-benzyl]-1-[3-(4-fluoro-phenoxy)-propyl]-5-methyl-1,3-dihydro-benzoimidazol-2-ylideneamine (2.5 mg, 11%). HPLC-MS 640 [M+1]+, 320 (100%).

Using a similar procedure starting from 3-(4-Bromo-benzyl)-5-fluoro-1-[3-(4-fluoro-phenoxy)-propyl]-1,3-dihydro-benzoimidazol-2-ylideneamine and the appropriate amine the compound in Table 21 was synthesised.

TABLE 21

| Cpd | Structure | Name | Yield | HPLC-MS |
|---|---|---|---|---|
| 63 | 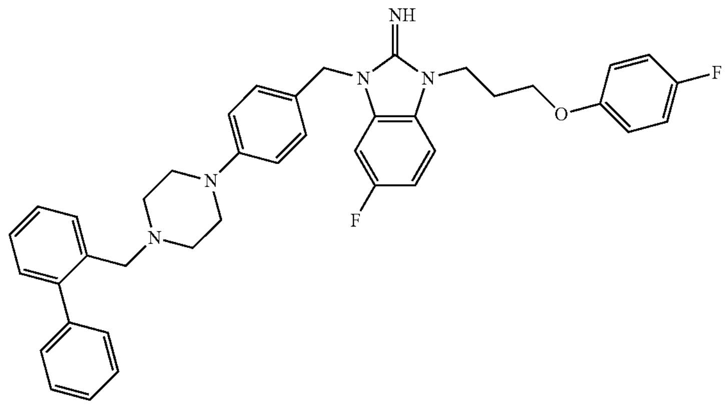 [SMILES: N=c1n(CCCOc2ccc(F)cc2)c2ccc(F)cc2n1Cc1ccc(N2CCN(Cc3ccccc3-c3ccccc3)CC2)cc1] | 3-[4-(4-Biphenyl-2-ylmethyl-piperazin-1-yl)-benzyl]-5-fluoro-1-[3-(4-fluoro-phenoxy)-propyl]-1,3-dihydro-benzoimidazol-2-ylideneamine | 2% | 644 [M + 1]+, 323 (100%) |

Example 13

Synthesis of 3-(4-{4-[2-(4-chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine (Compound 64)

Scheme 13 shows the route to Compound 64

Step 1 Synthesis of 3-(4-{4-[2-(4-chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine (Compound 64)

To a degassed solution of 3-(4-bromo-benzyl)-5-fluoro-1-[3-(4-fluoro-phenoxy)-propyl]-1,3-dihydro-benzoimidazol-2-ylideneamine (0.060 g, 0.11 mmol) in toluene (2 ml) at rt Scheme 13

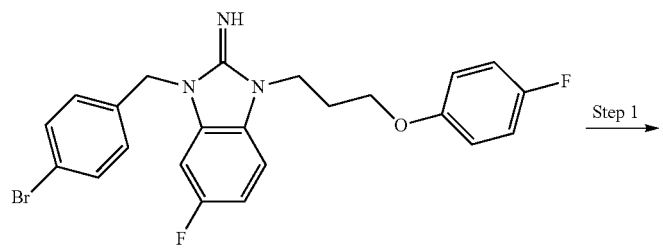

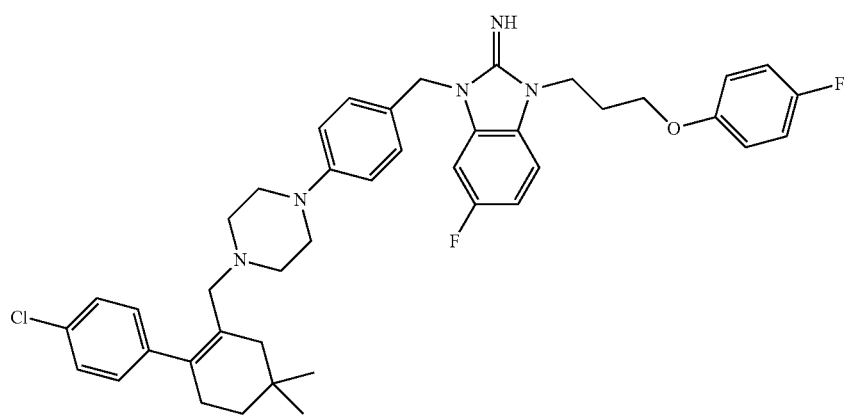

under nitrogen was added Pd(OAc)$_2$ (0.9 mg, 4.0 µmol) and BINAP (4.7 mg, 7.6 µmol). Nitrogen was bubbled through the mixture for 10 min before a degassed solution of 1-[2-(4-chloro-phenyl)-5,5-dimethyl-cyclohex-1-enylmethyl]-piperazine (49 mg, 0.15 mmol) in toluene (1 ml) was introduced. After 5 min Cs$_2$CO$_3$ (0.41 g, 1.27 mmol) was added. During all additions nitrogen was continuously bubbled through the reaction. Once the additions were completed the reaction vessel was sealed and then heated to 95° C. where it was maintained for 18 h. After this time, the reaction was cooled to rt and filtered through Celite® and the collected solids were washed with dichloromethane. The combined filtrate and washings were concentrated under reduced pressure and the crude product was purified by preparative HPLC. The purified product was partitioned between a saturated solution of NaHCO$_3$ and dichloromethane and the organic phase was separated. The aqueous layer was extracted with additional dichloromethane and then the combined organic fractions were washed with brine, dried (Na$_2$SO$_4$), filtered and concentrated under reduced pressure to provide 3-(4-{4-[2-(4-chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine (34 mg, 45%). HPLC-MS 710 [M+1]$^+$, 348.

Example 14

Synthesis of 3-(3-{3-[4-(4-biphenyl-2-ylmethyl-piperazin-1-yl)-benzyl]-2-imino-2,3-dihydro-benzoimidazol-1-yl}-propoxy)-benzoic acid (Compound 70)

The route to the title compound is illustrated in Scheme 14.

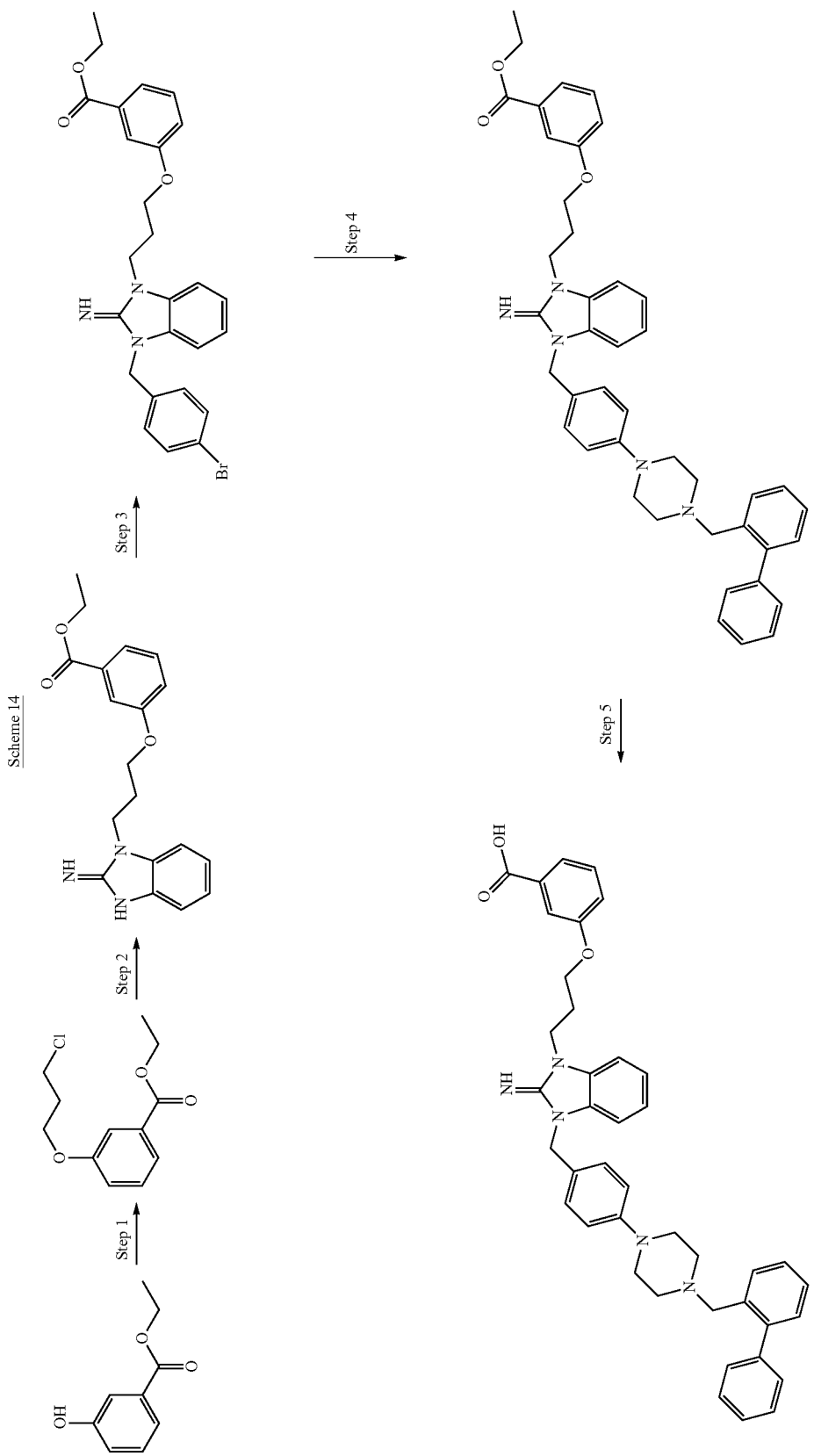

Step 1 Synthesis of 3-(3-chloro-propoxy)-benzoic acid ethyl ester

To a solution of ethyl-3-hydroxybenzoate (5.0 g, 30 mmol) in acetone (250 ml) at rt was added 1-bromo-3-chloro-propane (5.67 g, 36 mmol) and $K_2CO_3$ (12.4 g, 90 mmol). The resulting suspension was heated to reflux where it was maintained for 25 h. After this time, the mixture was concentrated under reduced pressure and the resulting solid was partitioned between $H_2O$ and EtOAc. The organic phase was separated and the aqueous phase was extracted with additional EtOAc. The combined organic fractions were washed with 1N HCl and brine, dried ($Na_2SO_4$), filtered and concentrated under reduced pressure to provide the crude product. Purification by chromatography on silica eluting with 5% EtOAc/hexane gave 3-(3-chloro-propoxy)-benzoic acid ethyl ester as a colourless oil (5.0 g, 68%).

Step 2 Synthesis of 3-[3-(2-imino-2,3-dihydro-benzoimidazol-1-yl)-propoxy]-benzoic acid ethyl ester To a solution of 3-(3-chloro-propoxy)-benzoic acid ethyl ester (5.50 g, 22.7 mmol) in DMF (150 ml) at rt was added $Cs_2CO_3$ (14.8 g, 45.5 mmol) and 1,3-dihydro-benzoimidazol-2-ylidene amine (2.75 g, 20.7 mmol). The reaction was heated to 50° C. for 12 h. After this time, the resulting mixture was cooled to rt and partitioned between EtOAc and $H_2O$. The organic layer was separated and the aqueous phase was extracted with additional EtOAc. The combined organic fractions were washed with brine, dried ($Na_2SO_4$), filtered and concentrated under redcued pressure. The crude product was purified by chromatography on silica eluting with 2% MeOH/dichloromethane to give 3-[3-(2-imino-2,3-dihydro-benzoimidazol-1-yl)-propoxy]-benzoic acid ethyl ester (4.9 g g, 64%). HPLC-MS 340 [M+1]$^+$.

The compound in Table 22 was made using a similar procedure. The following modifications are noted:
  Methyl 4-(3-bromopropoxy)benzoate was used as the alkylating agent and the reaction was complete after 4 h.

TABLE 22

| Structure | Name | HPLC-MS | Yield |
| --- | --- | --- | --- |
| [structure] | 4-[3-(2-Imino-2,3-dihydro-benzoimidazol-1-yl)-propoxy]-benzoic acid methyl ester | 326 [M + 1]$^+$ | 76% |

Step 3 Synthesis of 3-{3-[3-(4-bromo-benzyl)-2-imino-2,3-dihydro-benzoimidazol-1-yl]-propoxy}-benzoic acid ethyl ester (Compound 65)

To a solution of 3-[3-(2-imino-2,3-dihydro-benzoimidazol-1-yl)-propoxy]-benzoic acid ethyl ester (2.45 g, 7.3 mmol) in 2-butanone (125 ml) was added 4-bromobenzylbromide (2.88 g, 11.7 mmol). The reaction was heated to 80° C. where it was maintained for 24 h. After this time the mixture was cooled to rt and filtered. The collected solids were washed with additional cold 2-butanone and then dried to give 3-{3-[3-(4-bromo-benzyl)-2-imino-2,3-dihydro-benzoimidazol-1-yl]-propoxy}-benzoic acid ethyl ester, hydrobromide salt (2.5 g, 59%). HPLC-MS 508, 510 [M+1]+.

Using a similar procedure starting from the appropriate iminobenzimidazole, the compounds shown in Table 23 were prepared.

by chromatography on silica eluting with EtOAc/hexane provided 3-(3-{3-[4-(4-biphenyl-2-ylmethyl-piperazin-1-yl)-benzyl]-2-imino-2,3-dihydro-benzoimidazol-1-yl}-propoxy)-benzoic acid ethyl ester (42 mg, 6%). HPLC-MS 680 [M+1]+, 341.

TABLE 23

| Cpd | Structure | Name | HPLC-MS | Yield |
|---|---|---|---|---|
| 66 | 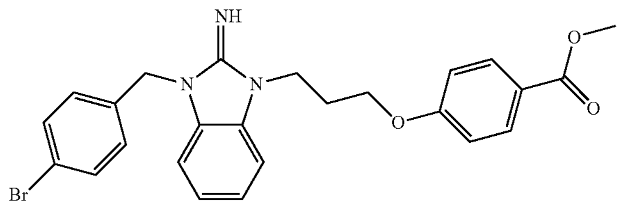 [SMILES: COC(=O)c1ccc(OCCCn2c(=N)n(Cc3ccc(Br)cc3)c3ccccc32)cc1] | 4-{3-[3-(4-Bromo-benzyl)-2-imino-2,3-dihydro-benzoimidazol-1-yl]-propoxy}-benzoic acid methyl ester | 494, 496 [M + 1]+ | 72% |
| 67 | 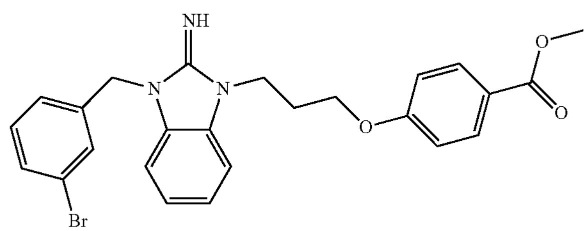 [SMILES: COC(=O)c1ccc(OCCCn2c(=N)n(Cc3cccc(Br)c3)c3ccccc32)cc1] | 4-{3-[3-(3-Bromo-benzyl)-2-imino-2,3-dihydro-benzoimidazol-1-yl]-propoxy}-benzoic acid methyl ester | 494, 496 [M + 1]+ | 79% |
| 68 | 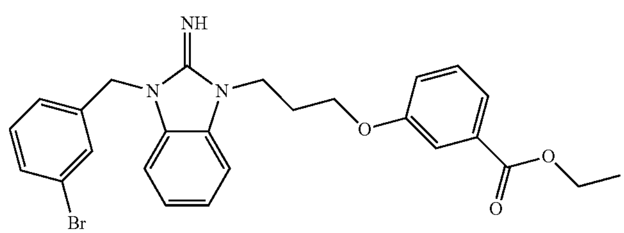 [SMILES: CCOC(=O)c1cccc(OCCCn2c(=N)n(Cc3cccc(Br)c3)c3ccccc32)c1] | 3-{3-[3-(3-Bromo-benzyl)-2-imino-2,3-dihydro-benzoimidazol-1-yl]-propoxy}-benzoic acid ethyl ester | 508, 510 [M + 1]+ | 59% |

Step 4 Synthesis of 3-(3-{3-[4-(4-biphenyl-2-ylmethyl-piperazin-1-yl)-benzyl]-2-imino-2,3-dihydro-benzoimidazol-1-yl}-propoxy)-benzoic acid ethyl ester (Compound 69)

To a mixture of 3-{3-[3-(4-bromo-benzyl)-2-imino-2,3-dihydro-benzoimidazol-1-yl]-propoxy}-benzoic acid ethyl ester (0.50 g, 0.99 mmol), sodium tert-butoxide (0.26 g, 2.67 mmol), 2-dicyclohexylphosphino-2',4',6'-triisopropylbiphenyl (33 mg, 0.07 mmol) and Pd(OAc)$_2$ (22 mg, 0.10 mmol) at rt was added a degassed solution of 1-biphenyl-2-ylmethyl-piperazine (0.25 g, 0.99 mmol) in toluene (15 ml) and tert-butanol (3 ml). The reaction was heated to 120° C. where it was maintained fro 3 d. After this time, the reaction was cooled to rt and concentrated under reduced pressure. The material that remained was partitioned between H$_2$O and EtOAc and the organic phase was separated, dried (Na$_2$SO$_4$), filtered and concentrated under reduced pressure. Purification Step 5 Synthesis of 3-(3-{3-[4-(4-biphenyl-2-ylmethyl-piperazin-1-yl)-benzyl]-2-imino-2,3-dihydro-benzoimidazol-1-yl}-propoxy)-benzoic acid (Compound 70)

To a solution of 3-(3-{3-[4-(4-biphenyl-2-ylmethyl-piperazin-1-yl)-benzyl]-2-imino-2,3-dihydro-benzoimidazol-1-yl}-propoxy)-benzoic acid ethyl ester (20 mg, 0.03 mmol) in MeOH (2 ml) at rt was added 1M NaOH (2 ml). The reaction was heated at to 80° C. for 5 h and then concentrated under reduced pressure. The material that remained was partitioned between EtOAc and H$_2$O and the organic layer was separated, dried (Na$_2$SO$_4$), filtered and concentrated under reduced pressure to give 3-(3-{3-[4-(4-biphenyl-2-ylmethyl-piperazin-1-yl)-benzyl]-2-imino-2,3-dihydro-benzoimidazol-1-yl}-propoxy)-benzoic acid (10 mg, 52%). HPLC-MS [M+1]+ 327. $^1$H NMR (500 MHz, CHLOROFORM-d) □ ppm 2.13 (2 H, br s), 2.36 (4 H, br s), 2.87 (4 H, br. s.), 3.39 (2 H, s), 3.99

(2 H, br s), 4.39 (2 H, br s), 5.24-5.55 (2 H, m), 6.37-6.87 (3 H, m), 7.09 (7 H, br s), 7.29-7.67 (11 H, m).

Example 15

Synthesis of 3-[3-(3-benzyl-2-imino-2,3-dihydro-benzoimidazol-1-yl)-propoxy]-benzoic acid ethyl ester (Compound 71)

The title compound was synthesised according to the route set out in Scheme 15.

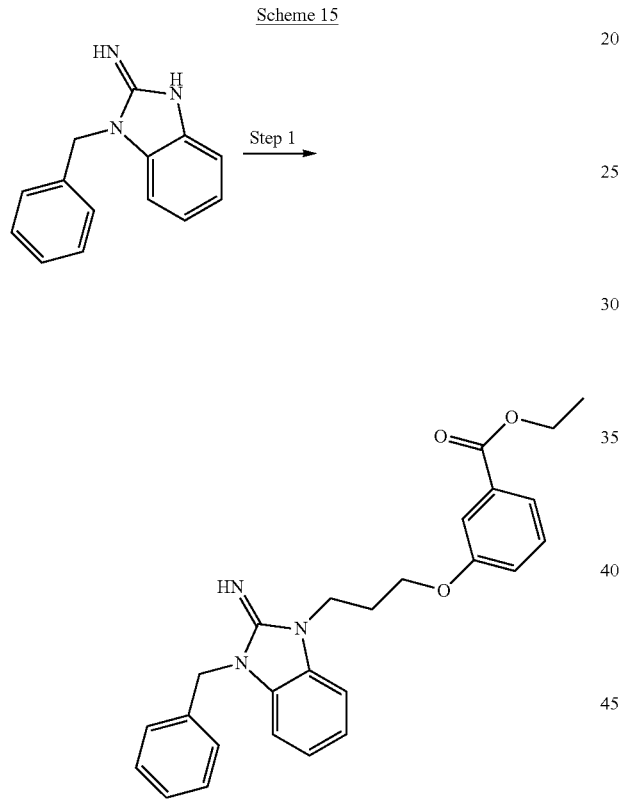

Scheme 15

Step 1 Synthesis of 3-[3-(3-benzyl-2-imino-2,3-dihydro-benzoimidazol-1-yl)-propoxy]-benzoic acid ethyl ester (Compound 71)

To a solution of 1-benzyl-1,3-dihydro-benzoimidazol-2-ylideneamine (247 mg, 1.10 mmol) in 2-butanone (40 ml) was added 3-(3-chloro-propoxy)-benzoic acid ethyl ester (0.40 g, 1.65 mmol) and KI (0.55 g, 3.32 mmol). The reaction was heated to 85° C. where it was maintained for 54 h. After this time, the mixture was cooled to rt and filtered. The filtrate was concentrated under reduced pressure and combined with the collected solid, washed with diethyl ether and petroleum ether and dried to provide 3-[3-(3-benzyl-2-imino-2,3-dihydro-benzoimidazol-1-yl)-propoxy]-benzoic acid ethyl ester (350 mg, 74%). HPLC-MS 430 [M+1]$^+$.

Example 16

Synthesis of 3-{3-[3-(4-fluoro-phenoxy)-propyl]-2-imino-2,3-dihydro-benzoimidazol-1-ylmethyl}-benzoic acid (Compound 72)

The title compound was synthesised according to the route set out in Scheme 16.

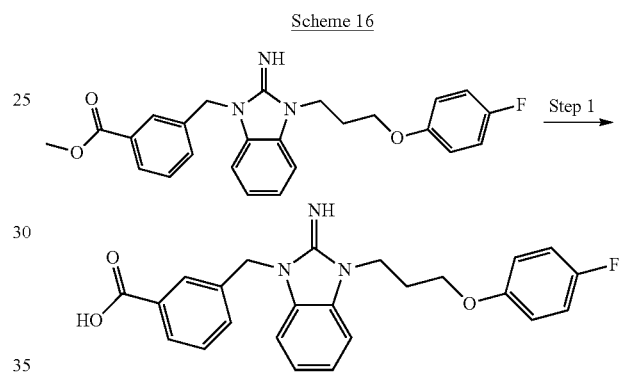

Scheme 16

Step 1 Synthesis of 3-{3-[3-(4-fluoro-phenoxy)-propyl]-2-imino-2,3-dihydro-benzoimidazol-1-ylmethyl}-benzoic acid (Compound 72)

To a solution of 3-{3-[3-(4-fluoro-phenoxy)-propyl]-2-imino-2,3-dihydro-benzoimidazol-1-ylmethyl}-benzoic acid methyl ester (50 mg, 0.12 mmol) in MeOH (2 ml) at rt was added aqueous NaOH (1 ml). The reaction was stirred for 1 h at rt and then it was concentrated under reduced pressure. The material that remained was partitioned between EtOAc and H$_2$O and the 1M KHSO$_4$ was added. The suspension was then filtered and the collected solid was dried to provide 3-{3-[3-(4-fluoro-phenoxy)-propyl]-2-imino-2,3-dihydro-benzoimidazol-1-ylmethyl}-benzoic acid (20 mg, 41%). HPLC-MS 420 [M+1]$^+$.

Example 17

Synthesis of 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid (Compound 74)

The title compound was synthesised according to the route set out in Scheme 17.

Scheme 17

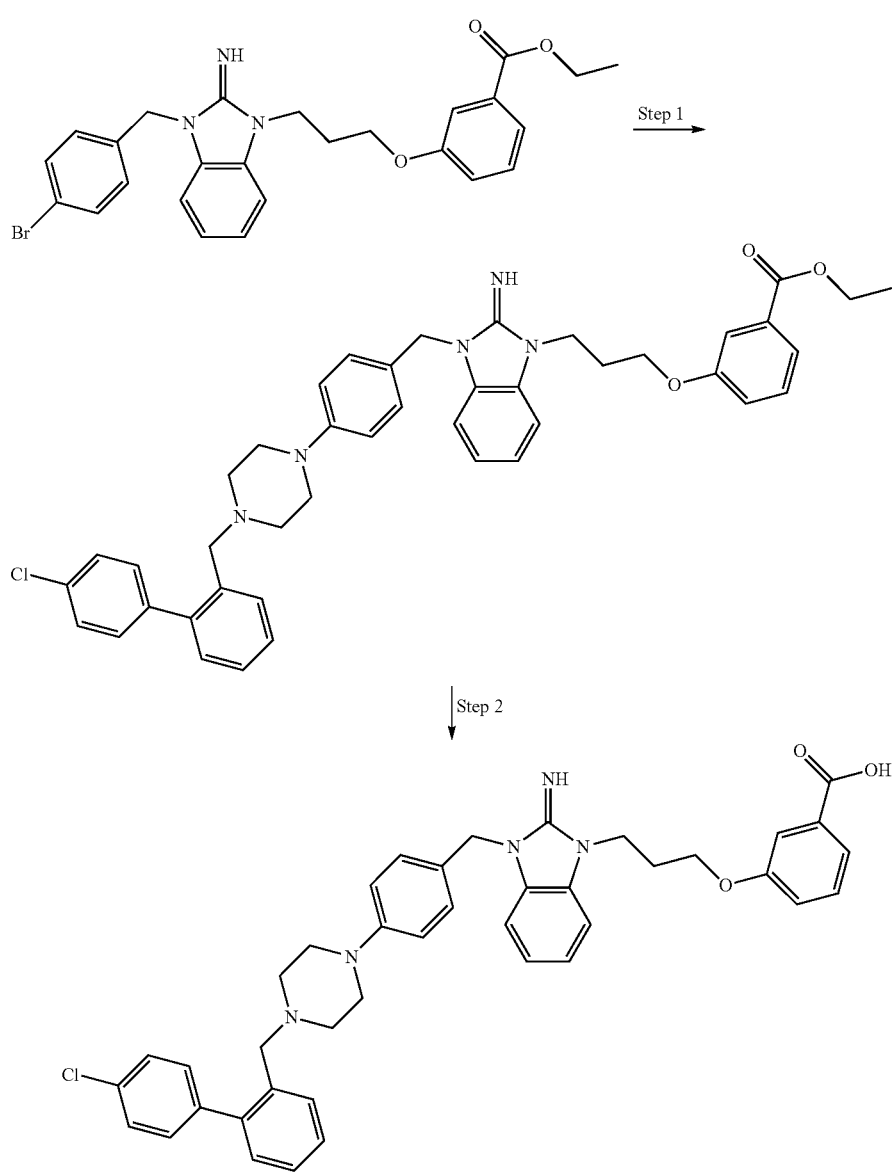

Step 1 Synthesis of 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid ethyl ester (Compound 73)

To a degassed solution of 3-{3-[3-(4-bromo-benzyl)-2-imino-2,3-dihydro-benzoimidazol-1-yl]-propoxy}-benzoic acid ethyl ester, hydrobromide salt (0.2 g, 0.34 mmol) in anhydrous toluene (3 ml) was added Pd(OAc)$_2$ (33 mg, 0.077 mmol). Nitrogen was bubbled through the suspension for 10 min before BINAP (49 mg, 0.079 mmol) was added. After a further 2 min 1-(4'-chloro-biphenyl-2-ylmethyl)-piperazine (112 mg, 0.39 mmol) in degassed toluene (3 ml) was introduced and then after an additional 2 min Cs$_2$CO$_3$ (2.5 g, 7.69 mmol) was added and the reaction was stirred for 2 min. Throughout all of the additions nitrogen was continuously bubbled through the reaction mixture. The reaction was then sealed and heated to 95° C. where it was maintained for 5 h. After this time, the reaction was cooled to rt and filtered through Celite®. The collected solids were washed with additional dichloromethane and then the combined filtrate and washings were concentrated under reduced pressure to give the crude product. Purification by chromatography on silica eluting with 5% MeOH/dichloromethane provided 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid ethyl ester (147 mg, 61%). HPLC-MS 715 [M+1]$^+$, 358.

Step 2 Synthesis of 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid (Compound 74)

To a solution of 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid ethyl ester (140 mg, 0.20 mmol) in THF (1.2 ml), MeOH (1.2 ml) and H$_2$O (0.6 ml) at 0° C. was added LiOH.H$_2$O (16 mg, 0.39 mmol). The reaction was warmed to rt where it was maintained for 20 h. After this time, the mixture was concentrated under reduced pressure and then partitioned between saturated NaHCO$_3$ and dichloromethane to adjust the pH to ~8. The organic phase was separated, dried (Na$_2$SO$_4$), filtered and concentrated under reduced pressure. Purification by preparative HPLC provided 3-[3-(3-{4-[4-(4'-chloro-biphenyl-2-ylmethyl)-piperazin-1-yl]-benzyl}-2-imino-2,3-dihydro-benzoimidazol-1-yl)-propoxy]-benzoic acid (15 mg, 11%). HPLC-MS 686 [M+1]$^+$, 344.

Example 18

Synthesis of 3-{3-[3-(3-{4-[2-(4-chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid (Compound 75)

Compound 75 was synthesised by the route shown in Scheme 18.

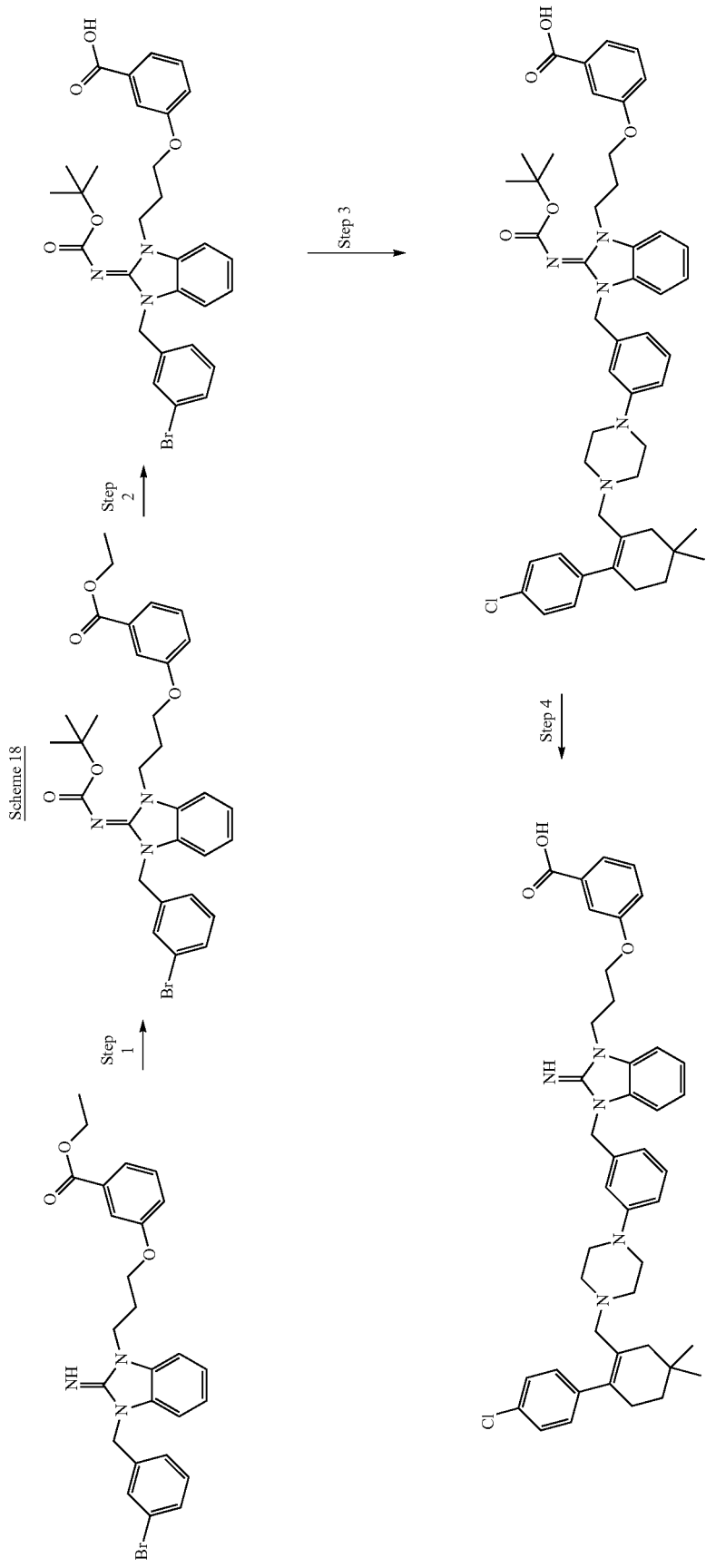
Scheme 18

Step 1 Synthesis of 3-(3-{3-(3-bromo-benzyl)-2-[tert-butoxycarbonylimino]-2,3-dihydro-benzoimidazol-1-yl}-propoxy)-benzoic acid ethyl ester To a solution of 3-{3-[3-(3-bromo-benzyl)-2-imino-2,3-dihydro-benzoimidazol-1-yl]-propoxy}-benzoic acid ethyl ester, hydrobromide salt (0.15 g, 0.25 mmol) in 1,4-dioxane (4 ml) and H₂O (1 ml) at rt was added NaOH (24 mg, 0.60 mmol) and di-tert-butyl dicarbonate (128 mg, 0.59 mmol). The mixture was stirred for 16 h and then concentrated under reduced pressure. The crude material was partitioned between H₂O and dichloromethane and the organic phase was separated, dried (Na₂SO₄), filtered and concentrated under reduced pressure to provide 3-(3-{3-(3-bromo-benzyl)-2-[tert-butoxycarbonylimino]-2,3-dihydro-benzoimidazol-1-yl}-propoxy)-benzoic acid ethyl ester (155 mg, 100%) which was used without further purification. HPLC-MS 608, 610 [M+1]⁺.

Step 2 Synthesis of 3-(3-{3-(3-bromo-benzyl)-2-[tert-butoxycarbonylimino]-2,3-dihydro-benzoimidazol-1-yl}-propoxy)-benzoic acid To a solution of 3-(3-{3-(3-bromo-benzyl)-2-[tert-butoxycarbonylimino]-2,3-dihydro-benzoimidazol-1-yl}-propoxy)-benzoic acid ethyl ester (155 mg, 0.25 mmol) in THF (2 ml), MeOH (2 ml) and H₂O (1 ml) was added LiOH.H₂O (53 mg, 1.27 mmol). The reaction was warmed to 40° C. where it was maintained for 20 h. After this time, the reaction was cooled to rt concentrated under reduced pressure and then partitioned between EtOAc and 1M HCl. The organic phase was separated and the aqueous phase was extracted with additional EtOAc. The combined organic layers were washed with brine, dried (Na₂SO₄), filtered and concentrated under reduced pressure to provide 3-(3-{3-(3-bromo-benzyl)-2-[tert-butoxycarbonylimino]-2,3-dihydro-benzoimidazol-1-yl}-propoxy)-benzoic acid (150 mg, 100%). HPLC-MS 580, 582 [M+1]⁺.

Step 3 Synthesis of 3-{3-[2-[tert-butoxycarbonylimino]-3-(3-{4-[2-(4-chloro-phenyl)-5,5-dimethyl-cyclohex-1-enylmethyl]-piperazin-1-yl}-benzyl)-2,3-dihydro-benzoimidazol-1-yl]-propoxy}-benzoic acid To a degassed solution of 3-(3-{3-(3-bromo-benzyl)-2-[tert-butoxycarbonylimino]-2,3-dihydro-benzoimidazol-1-yl}-propoxy)-benzoic acid (0.15 g, 0.25 mmol) in toluene (2 ml) at rt under nitrogen was added Pd(OAc)₂ (5 mg, 0.12 mmol) and BINAP (30 mg, 0.048 mmol). Nitrogen was bubbled through the mixture for 10 min before a degassed solution of 1-[2-(4-chloro-phenyl)-5,5-dimethyl-cyclohex-1-enylmethyl]-piperazine (90 mg, 0.28 mmol) in toluene (1 ml) was introduced. After 5 min Cs₂CO₃ (0.84 g, 2.58 mmol) was added. During all additions nitrogen was continuously bubbled through the reaction. Once the additions were completed the reaction vessel was sealed and then heated to 95° C. where it was maintained for 3 h. After this time, the reaction was cooled to rt and additional Pd(OAc)₂ (5 mg, 0.12 mmol) and BINAP (30 mg, 0.048 mmol) were introduced. The reaction was then heated to 95° C. where it was maintained for a further 2 h. After this time, the reaction was cooled to rt and filtered through Celite®. The collected solids were washed with dichloromethane and the combined filtrate and washings were concentrated under reduced pressure. The crude product 3-{3-[2-[tert-butoxycarbonylimino]-3-(3-{4-[2-(4-chloro-phenyl)-5,5-dimethyl-cyclohex-1-enylmethyl]-piperazin-1-yl}-benzyl)-2,3-dihydro-benzoimidazol-1-yl]-propoxy}-benzoic acid (290 mg) was used in the next step without further purification. HPLC-MS 818, 820 [M+1]⁺.

Step 4 Synthesis of 3-{3-[3-(3-{4-[2-(4-chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid (Compound 75)

To a solution of 3-{3-[2-[tert-butoxycarbonylimino]-3-(3-{4-[2-(4-chloro-phenyl)-5,5-dimethyl-cyclohex-1-enylmethyl]-piperazin-1-yl}-benzyl)-2,3-dihydro-benzoimidazol-1-yl]-propoxy}-benzoic acid (0.15 g, 0.18 mmol) in dichloromethane (2.25 ml) at rt was added TFA (0.75 ml). The reaction was stirred at rt for 1 h and then concentrated under reduced pressure. The crude product was purified by preparative HPLC to provide 3-{3-[3-(3-{4-[2-(4-chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid (8.5 mg, 6%). HPLC-MS 718 [M+1]⁺, 360.

Example 19

Synthesis of 1-{3-[3-(4-biphenyl-2-ylmethyl-piperazin-1-yl)-benzyl]-2-imino-2,3-dihydro-benzoimidazol-1-yl}-3-(4-fluoro-phenoxy)-propan-2-ol (Compound 82)

Scheme 19 shows the route used to obtain the title compound.

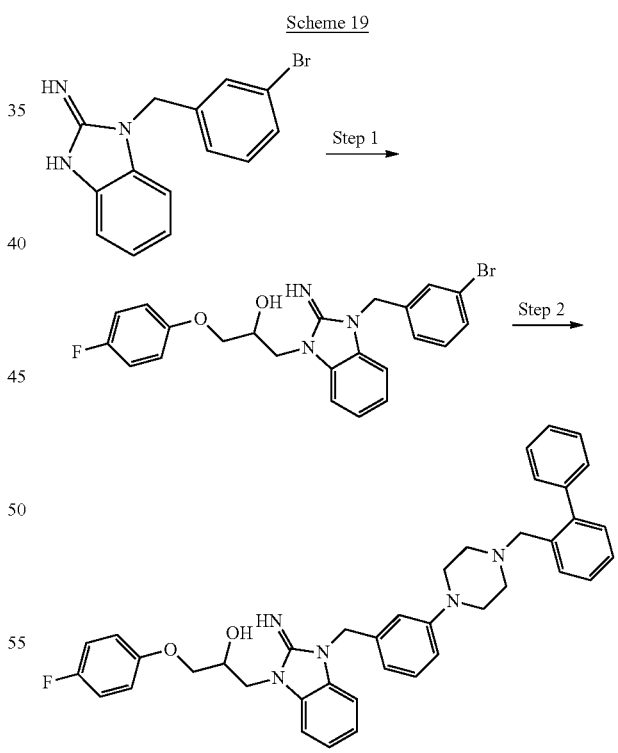

Scheme 19

Step 1 Synthesis of 1-[3-(3-bromo-benzyl)-2-imino-2,3-dihydro-benzoimidazol-1-yl]-3-(4-fluoro-phenoxy)-propan-2-ol (Compound 76)

To a solution of 1-(3-bromo-benzyl)-1,3-dihydro-benzoimidazol-2-ylideneamine (0.50 g, 1.66 mmol) in EtOH (30 ml) at rt was added 2-(4-fluoro-phenoxymethyl)-oxirane (278 mg, 1.66 mmol). The reaction was heated to reflux where it was maintained for 24 h. After this time, additional 2-(4-fluoro-phenoxymethyl)-oxirane (278 mg, 1.66 mmol) was introduced and the reaction was heated to reflux where it was left for a further 6 h. The mixture was cooled to rt and concentrated under reduced pressure. Purification by column chromatography on silica eluting with MeOH/dichloromethane (2-5% gradient) provided 1-[3-(3-bromo-benzyl)-2-imino-2,3-dihydro-benzoimidazol-1-yl]-3-(4-fluoro-phenoxy)-propan-2-ol (361 mg, 46%). HPLC-MS 470, 472 [M+1]$^+$.

Using a similar procedure and the appropriate iminobenzimdazole and oxirane starting materials the compounds in Table 24 were prepared.

TABLE 24

| Cpd | Structure | Name | HPLC-MS | Yield |
|---|---|---|---|---|
| 77 | 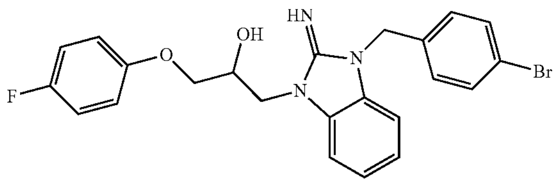 [SMILES: N=c1n(Cc2ccc(Br)cc2)c2ccccc2n1CC(O)COc1ccc(F)cc1] | 1-[3-(4-Bromo-benzyl)-2-imino-2,3-dihydro-benzoimidazol-1-yl]-3-(4-fluoro-phenoxy)-propan-2-ol | 471 [M + 1]$^+$ | 52% |
| 78 | 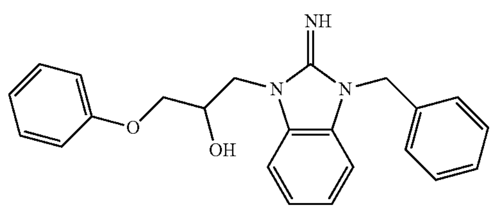 [SMILES: N=c1n(Cc2ccccc2)c2ccccc2n1CC(O)COc1ccccc1] | 1-(3-Benzyl-2-imino-2,3-dihydro-benzoimidazol-1-yl)-3-pbenoxy-propan-2-ol | 374 [M + 1]$^+$ | n/a |
| 79 | 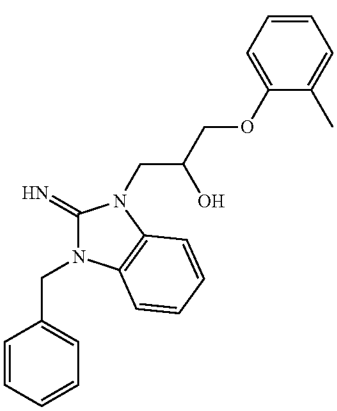 [SMILES: Cc1ccccc1OCC(O)Cn1c(=N)n(Cc2ccccc2)c2ccccc21] | 1-(3-Benzyl-2-imino-2,3-dihydro-benzoimidazol-1-yl)-3-o-tolyloxy-propan-2-ol | 388 [M + 1]$^+$ | n/a |
| 80 | 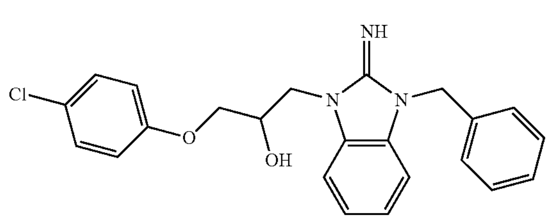 [SMILES: N=c1n(Cc2ccccc2)c2ccccc2n1CC(O)COc1ccc(Cl)cc1] | 1-(3-Benzyl-2-imino-2,3-dihydro-benzoimidazol-1-yl)-3-(4-chloro-phenoxy)-propan-2-ol | 408, 410 [M + 1]$^+$ | n/a |

TABLE 24-continued

| Cpd | Structure | Name | HPLC-MS | Yield |
|---|---|---|---|---|
| 81 | 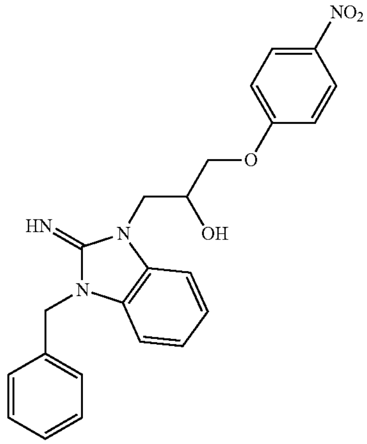 [SMILES: N=c1n(Cc2ccccc2)c2ccccc2n1CC(O)COc1ccc([N+](=O)[O-])cc1] | 1-(3-Benzyl-2-imino-2,3-dihydro-benzoimidazol-1-yl)-3-(4-nitro-phenoxy)-propan-2-ol | 419 [M + 1]+ | n/a |

Step 2 Synthesis of 1-{3-[3-(4-biphenyl-2-ylmethyl-piperazin-1-yl)-benzyl]-2-imino-2,3-dihydro-benzoimidazol-1-yl}-3-(4-fluoro-phenoxy)-propan-2-ol (Compound 82)

To a degassed solution of 1-[3-(3-bromo-benzyl)-2-imino-2,3-dihydro-benzoimidazol-1-yl]-3-(4-fluoro-phenoxy)-propan-2-ol (0.100 g, 0.21 mmol) in toluene (3 ml) at rt under nitrogen was added Pd(OAc)$_2$ (1 mg, 4.45 μmop and BINAP (5 mg, 8.03 μmol). Nitrogen was bubbled through the mixture for 10 min before a degassed solution of 1-biphenyl-2-ylmethyl-piperazine (64 mg, 0.25 mmol) in toluene (1 ml) was introduced. After 5 min Cs$_2$CO$_3$ (1.39 g, 4.27 mmol) was added. During all additions nitrogen was continuously bubbled through the reaction. Once the additions were completed the reaction vessel was sealed and then heated to 95° C. where it was maintained for 1d. After this time, the reaction was cooled to rt and additional Pd(OAc)$_2$ (1 mg, 4.45 □mol) and BINAP (5 mg, 8.03 □mol) were added. The reaction was then returned to 95° C. where it was maintained for 3 d. The suspension was then cooled to rt, filtered through Celite® and the collected solids were washed with dichloromethane. The combined filtrate and washings were concentrated under reduced pressure and the crude product was purified by preparative HPLC twice. The purified product was partitioned between a saturated solution of NaHCO$_3$ and dichloromethane and the organic phase was separated. The aqueous layer was extracted with additional dichloromethane and then the combined organic fractions were washed with brine, dried (Na$_2$SO$_4$), filtered and concentrated under reduced pressure to provide 1-{3-[3-(4-biphenyl-2-ylmethyl-piperazin-1-yl)-benzyl]-2-imino-2,3-dihydro-benzoimidazol-1-yl}-3-(4-fluoro-phenoxy)-propan-2-ol (10 mg, 7%). HPLC-MS 642 [M+1]+, 322.

Using a similar procedure with the appropriate bromide and amine starting materials the compounds in Table 25 were prepared.

TABLE 25

| Cpd | Structure | Name | HPLC-MS | Yield |
|---|---|---|---|---|
| 83 | 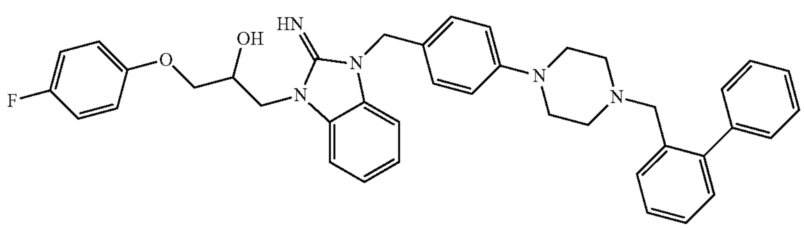 [SMILES: N=c1n(Cc2ccc(N3CCN(Cc4ccccc4-c4ccccc4)CC3)cc2)c2ccccc2n1CC(O)COc1ccc(F)cc1] | 1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol | 642 [M + 1]+, 322 | 12% |

Example 20

Synthesis of N-(3-{3-[3-(3-bromo-benzyl)-2-imino-2,3-dihydro-benzoimidazol-1-yl]-propoxy}-benzoyl)-methanesulfonamide (Compound 86)

Scheme 20 shows the route used to obtain the title compound.

Scheme 20

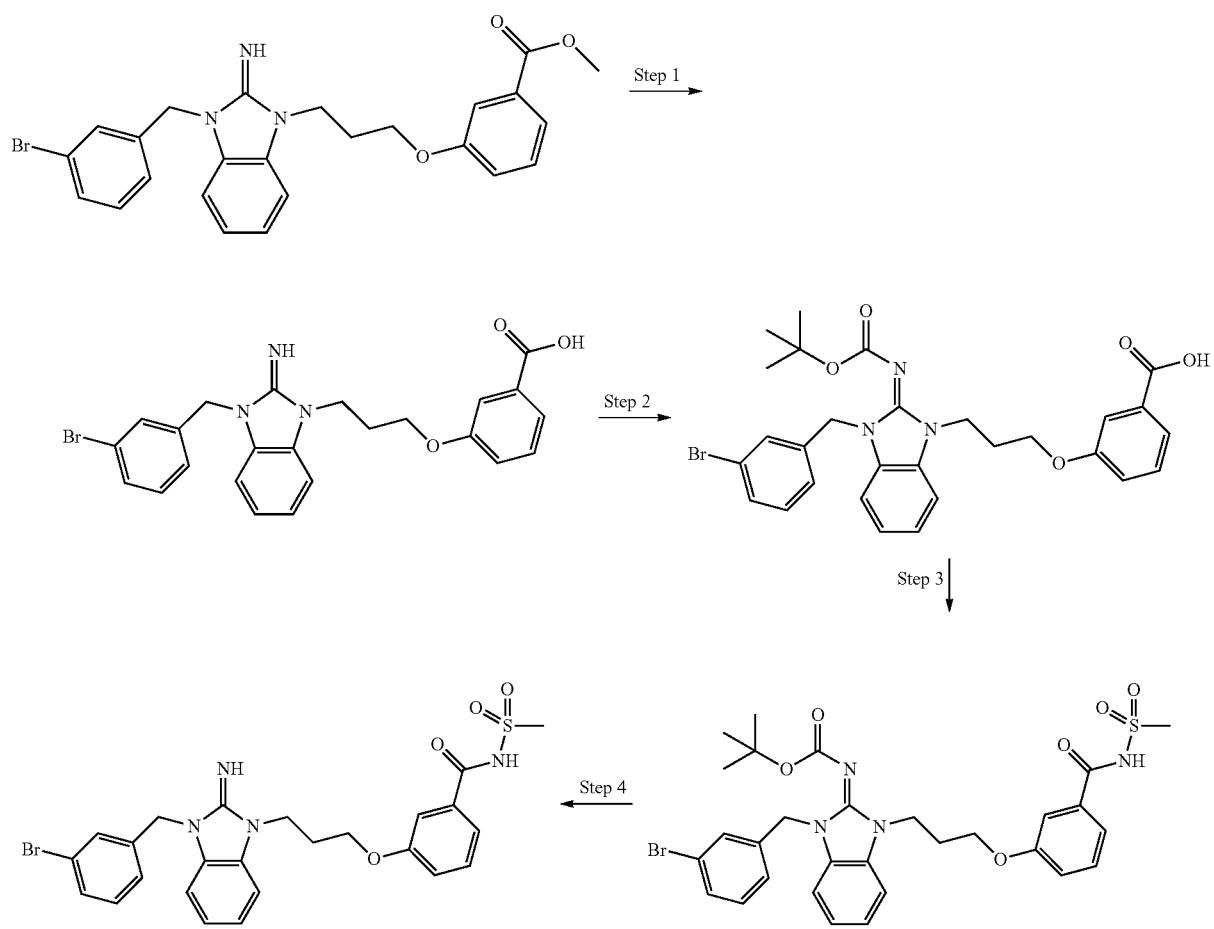

Step 1 Synthesis of 3-{3-[3-(3-bromo-benzyl)-2-imino-2,3-dihydro-benzoimidazol-1-yl]-propoxy}-benzoic acid sodium salt (Compound 84)

To a solution of 3-{3-[3-(3-bromo-benzyl)-2-imino-2,3-dihydro-benzoimidazol-1-yl]-propoxy}-benzoic acid methyl ester (0.50 g, 0.98 mmol) in EtOH (10 ml) at rt is added NaOH (71 mg, 1.77 mmol). The reaction was stirred until the complete consumption of starting material was observed by TLC. After this time, the mixture was concentrated under reduced pressure and then the material that remained was suspended in EtOAc and H₂O. The suspension was filtered and the collected solid was dried to provide 3-{3-[3-(3-bromo-benzyl)-2-imino-2,3-dihydro-benzoimidazol-1-yl]-propoxy}-benzoic acid sodium salt (0.42 g, 85%). HPLC-MS 480, 482 [M+1]$^+$.

Using a similar procedure with 3-{3-[3-(4-Bromo-benzyl)-2-imino-2,3-dihydro-benzoimidazol-1-yl]-propoxy}-benzoic acid ethyl ester the compound in Table 26 was prepared.

TABLE 26

| Cpd | Structure | Name | HPLC-MS | Yield |
|---|---|---|---|---|
| 85 | (structure shown) | 3-{3-[3-{4-Bromo-benzyl)-2-imino-2,3-dihydro-benzoimidazol-1-yl)-propoxy}-benzoic acid | 480, 482 [M + 1]$^+$ | 81% |

Step 2 Synthesis of 3-(3-{3-(3-bromo-benzyl)-2-[tert-butoxycarbonyl imino]-2,3-dihydro-benzoimidazol-1-yl}-propoxy)-benzoic acid To a solution of 3-{3-[3-(3-bromo-benzyl)-2-imino-2,3-dihydro-benzoimidazol-1-yl]-propoxy}-benzoic acid sodium salt (0.42 g, 0.84 mmol) in 1,4-dioxane and $H_2O$ at rt was added $Na_2CO_3$ (185 mg, 1.75 mmol) and di-tert-butyl dicarbonate (0.95 g, 4.38 mmol). The reaction was warmed to 50° C. where it was maintained until TLC revealed the consumption of starting material. After this time, the mixture was diluted with EtOAc and washed with $H_2O$. The organic phase was separated and concentrated under reduced pressure to provide the crude product that was purified by chromatography on silica eluting with 10% MeOH/chloroform to provide 3-(3-{3-(3-bromo-benzyl)-2-[tert-butoxycarbonylimino]-2,3-dihydro-benzoimidazol-1-yl}-propoxy)-benzoic acid as a yellow solid (250 mg, 51%). LCMS 580, 582 [M+1]$^+$.

Step 3 Synthesis of [1-(3-bromo-benzyl)-3-[3-(3-methanesulfonylaminocarbonyl-phenoxy)-propyl]-1,3-dihydro-benzoimidazol-ylidene]-carbamic acid tert-butyl ester To a solution of methyl sulfonamide (25 mg, 0.26 mmol) in tert-butanol (2.5 ml) and dichloromethane (2.5 ml) at rt under $N_2$ was added EDC (99 mg, 0.52 mmol), DMAP (44 mg, 0.36 mmol) and 3-(3-{3-(3-bromo-benzyl)-2-[tert-butoxycarbonylimino]-2,3-dihydro-benzoimidazol-1-yl}-propoxy)-benzoic acid (150 mg, 0.26 mmol). The reaction was stirred for 24 h and then diluted with EtOAc and washed with a solution of $KHSO_4$. The organic layer was separated, dried ($Na_2SO_4$) and concentrated under reduced pressure to provide [1-(3-bromo-benzyl)-3-[3-(3-methanesulfonylaminocarbonyl-phenoxy)-propyl]-1,3-dihydro-benzoimidazol-ylidene]-carbamic acid tert-butyl ester (120 mg, 71%). HPLC-MS 657, 659 [M+1]$^+$.

Step 4 Synthesis of N-(3-{3-[3-(3-bromo-benzyl)-2-imino-2,3-dihydro-benzoimidazol-1-yl]-propoxy}-benzoyl)-methanesulfonamide (Compound 86)

To [1-(3-bromo-benzyl)-3-[3-(3-methanesulfonylaminocarbonyl-phenoxy)-propyl]-1,3-dihydro-benzoimidazol-ylidene]-carbamic acid tert-butyl ester (90 mg, 0.14 mmol) at rt was added HCl in MeOH (5 ml). The reaction was stirred until the consumption of the starting material was observed by TLC. After this time, the mixture was concentrated under reduced pressure and purified by chromatography on basic alumina eluting with 10% MeOH/chloroform to provide N-(3-{3-[3-(3-bromo-benzyl)-2-imino-2,3-dihydro-benzoimidazol-1-yl]-propoxy}-benzoyl)-methanesulfonamide (27 mg, 35%). HPLC-MS 557, 559 [M+1]$^+$.

In addition to the compounds that were synthesised, compounds 87-106 (see Table 27) represent compounds that were purchased from commercial sources and screened in the biological assay.

TABLE 27

| 87 | 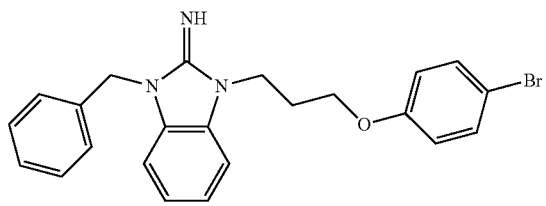 [SMILES: N=c1n(CCCOc2ccc(Br)cc2)c2ccccc2n1Cc1ccccc1] | 1-Benzyl-3-[3-(4-bromo-phenoxy)-propyl]-1,3-dihydro-benzoimidazol-2-ylideneamine |
| --- | --- | --- |
| 88 | 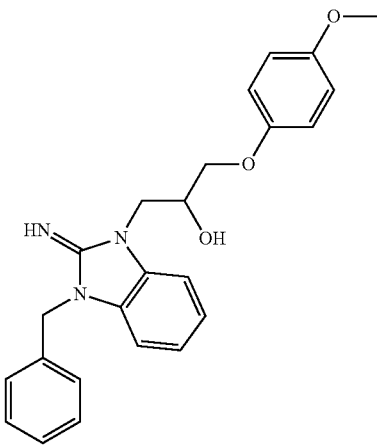 [SMILES: COc1ccc(OCC(O)Cn2c(=N)n(Cc3ccccc3)c3ccccc32)cc1] | 1-{3-Benzyl-2-imino-2,3-dihydro-benzoimidazol-1-yl)-3-(4-methoxy-phenoxy)-propan-2-ol |

| | | |
|---|---|---|
| 89 | 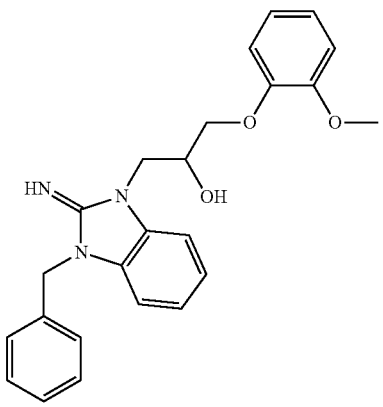 [SMILES: COc1ccccc1OCC(O)Cn1c(=N)n(Cc2ccccc2)c2ccccc21] | 1-(3-Benzyl-2-imino-2,3-dihydro-benzoimidazol-1-yl)-3-(2-methoxy-phenoxy)-propan-2-ol |
| 90 | 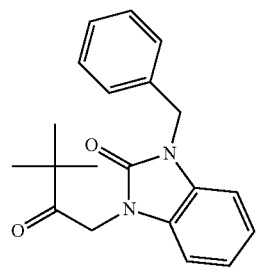 [SMILES: CC(C)(C)C(=O)Cn1c(=O)n(Cc2ccccc2)c2ccccc21] | 1-(3-Benzyl-2-imino-2,3-dihydro-benzoimidazol-1-yl)-3,3-dimethyl-butan-2-one |
| 91 | 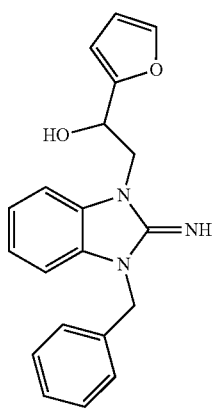 [SMILES: N=c1n(Cc2ccccc2)c2ccccc2n1CC(O)c1ccco1] | 2-(3-Benzyl-2-imino-2,3-dihydro-benzoimidazol-1-yl)-1-furan-2-yl-ethanol |
| 92 | 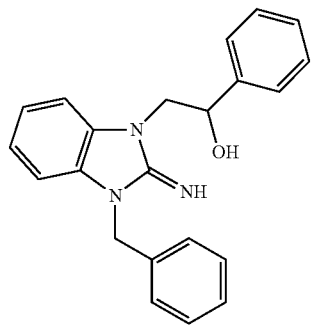 [SMILES: N=c1n(Cc2ccccc2)c2ccccc2n1CC(O)c1ccccc1] | 2-(3-Benzyl-2-imino-2,3-dihydro-benzoimidazol-1-yl)-1-phenyl-ethanol |

TABLE 27-continued
| | | |
|---|---|---|
| 93 | 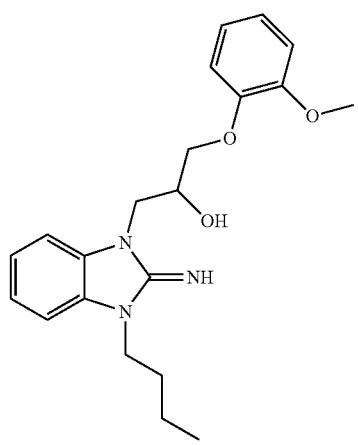 [SMILES: CCCCn1c(=N)n(CC(O)COc2ccccc2OC)c2ccccc21] | 1-(3-Butyl-2-imino-2,3-dihydro-benzoimidazol-1-yl)-3-(2-methoxy-phenoxy)-propan-2-ol |
| 94 | 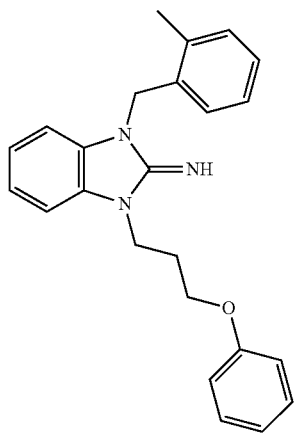 [SMILES: Cc1ccccc1Cn1c(=N)n(CCCOc2ccccc2)c2ccccc21] | 1-(2-Methyl-benzyl)-3-(3-phenoxy-propyl)-1,3-dihydro-benzoimidazol-2-ylideneamine |
| 95 | 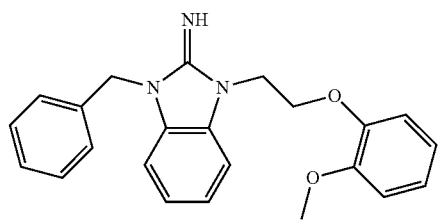 [SMILES: COc1ccccc1OCCn1c(=N)n(Cc2ccccc2)c2ccccc21] | 1-Benzyl-3-[2-(2-methoxy-phenoxy)-ethyl]-1,3-dihydro-benzoimidazol-2-ylideneamine |
| 96 | 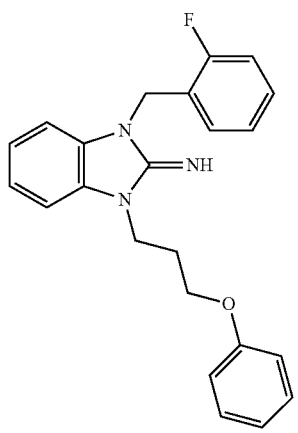 [SMILES: N=c1n(CCCOc2ccccc2)c2ccccc2n1Cc1ccccc1F] | 1-(2-Fluoro-benzyl)-3-(3-phenoxy-propyl)-1,3-dihydro-benzoimidazol-2-ylideneamine |

TABLE 27-continued
| | | |
|---|---|---|
| 97 | 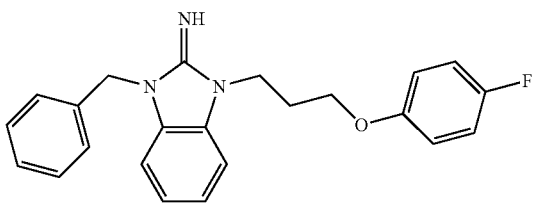 [SMILES: N=c1n(CCCOc2ccc(F)cc2)c2ccccc2n1Cc1ccccc1] | 1-Benzyl-3-[3-(4-fluoro-phenoxy)-propyl]-1,3-dihydro-benzoimidazol-2-ylideneamine |
| 98 | 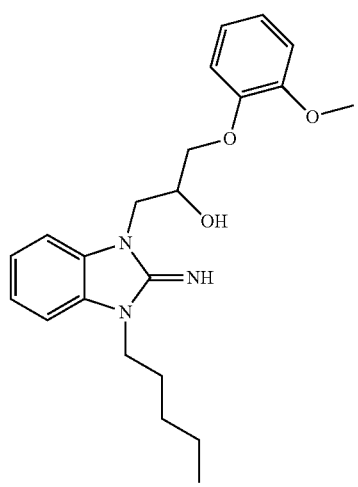 [SMILES: CCCCCn1c(=N)n(CC(O)COc2ccccc2OC)c2ccccc21] | 1-(2-Imino-3-pentyl-2,3-dihydro-benzoimidazol-1-yl)-3-(2-methoxy-phenoxy)-propan-2-ol |
| 99 | 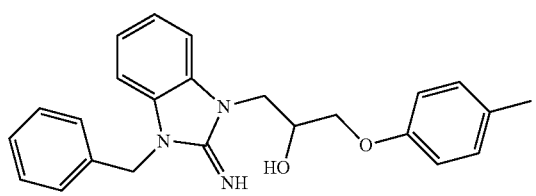 [SMILES: Cc1ccc(OCC(O)Cn2c(=N)n(Cc3ccccc3)c3ccccc32)cc1] | 1-(3-Benzyl-2-imino-2,3-dihydro-benzoimidazol-1-yl)-3-p-tolyloxy-propan-2-ol |
| 100 | 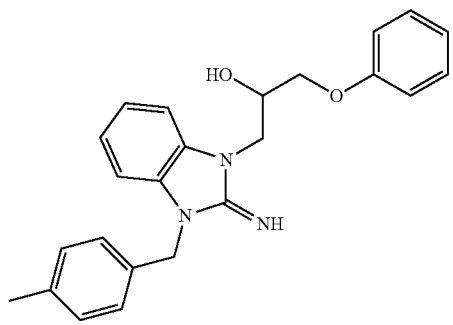 [SMILES: Cc1ccc(Cn2c(=N)n(CC(O)COc3ccccc3)c3ccccc32)cc1] | 1-[2-Imino-3-(4-methyl-benzyl)-2,3-dihydro-benzoimidazol-1-yl]-3-phenoxy-propan-2-ol |

TABLE 27-continued
| | | |
|---|---|---|
| 101 | 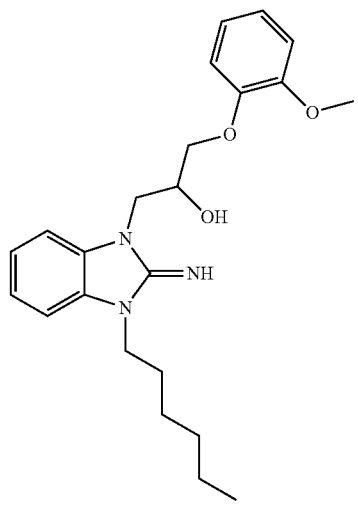 [SMILES: CCCCCCn1c(=N)n(CC(O)COc2ccccc2OC)c2ccccc21] | 1-(3-Hexyl-2-imino-2,3-dihydro-benzoimidazol-1-yl)-3-(2-methoxy-phenoxy)-propan-2-ol |
| 102 | 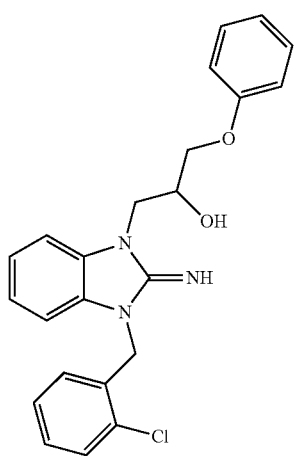 [SMILES: N=c1n(Cc2ccccc2Cl)c2ccccc2n1CC(O)COc1ccccc1] | 1-[3-(2-Chloro-benzyl)-2-imino-2,3-dihydro-benzoimidazol-1-yl]-3-phenoxy-propan-2-ol |
| 103 | 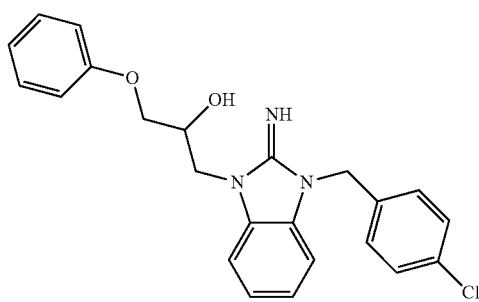 [SMILES: N=c1n(Cc2ccc(Cl)cc2)c2ccccc2n1CC(O)COc1ccccc1] | 1-[3-(4-Chloro-benzyl)-2-imino-2,3-dihydro-benzoimidazol-1-yl]-3-phenoxy-propan-2-ol |

TABLE 27-continued

| | | |
|---|---|---|
| 104 | 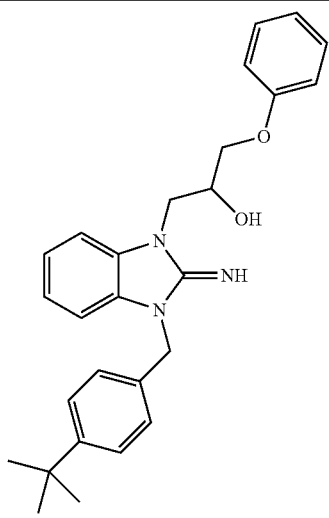 | 1-[3-(4-tert-Butyl-benzyl)-2-imino-2,3-dihydro-benzoimidazol-1-yl]-3-phenoxy-propan-2-ol |
| 105 | 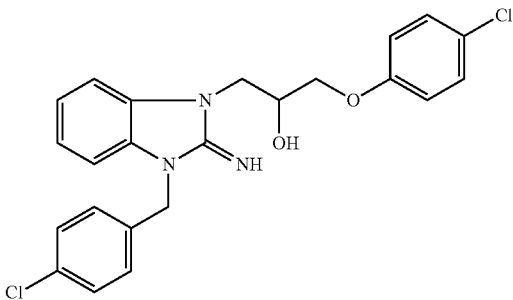 [SMILES: N=c1n(Cc2ccc(Cl)cc2)c2ccccc2n1CC(O)COc1ccc(Cl)cc1] | 1-[3-(4-Chloro-benzyl)-2-imino-2,3-dihydro-benzoimidazol-1-yl]-3-(4-chloro-phenoxy)-propan-2-ol |
| 106 | 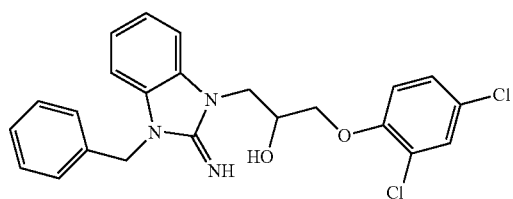 [SMILES: N=c1n(Cc2ccccc2)c2ccccc2n1CC(O)COc1ccc(Cl)cc1Cl] | 1-(3-Benzyl-2-imino-2,3-dihydro-benzoimidazol-1-yl)-3-(2,4-dichloro-phenoxy)-propan-2-ol |

Example 21

The homogeneous HTS assay for inhibitors of the Bcl-2 is shown schematically in FIG. 1. BH3 domain interaction is based on fluorescence polarisation. The inherent rotational diffusion of the Bak BH3 domain derived fluorescent labelled peptide decreases upon binding to Bcl-2. This shift in rotational diffusion is quantitated using the two-dimensional fluorescence intensity distribution analysis (2D-FIDA; Kask et al. 2000, Biophys. J. 78: 1703-1713).

Two different BH3 domain derived peptide ligands were synthesised and subsequently fluorescently labelled:
- a 16mer peptide covering amino acids 72-87 of the Bak protein; this peptide had been used by Wang and coworkers and Holinger and coworkers in their Bcl-2 protein binding studies; Wang and co-workers reported an equilibrium binding constant $K_D$ of ~0.2 µM to Bcl-2 protein;
  peptide sequence: GQVGRQLAIIGDDINR—N (Wang et al. 2002, Proc. Natl. Acad. Sci. U.S.A. 97: 7124-7129; Holinger et al. 1999, J. Biol. Chem. 274: 13298-13304).

The results are shown in Table 28 in which:
* represents an $IC_{50}$ value of >100 µM
** represents an $IC_{50}$ value of 11 to 100 µM
*** represents an $IC_{50}$ value of ≤10 µM

TABLE 28

| Compound | $IC_{50}$ [µM] Bcl-2 |
|---|---|
| 1 | ** |
| 2 | * |
| 3 | * |
| 4 | * |
| 5 | *** |
| 6 | ** |
| 7 | ** |
| 8 | ** |
| 9 | * |
| 10 | ** |
| 11 | ** |
| 12 | ** |
| 13 | ** |
| 14 | ** |
| 15 | *** |
| 16 | ** |

TABLE 28-continued

| Compound | IC$_{50}$ [μM] Bcl-2 |
|---|---|
| 17 | ** |
| 18 | *** |
| 19 | ** |
| 20 | *** |
| 21 | *** |
| 22 | *** |
| 24 | *** |
| 25 | *** |
| 25 | *** |
| 26 | *** |
| 27 | *** |
| 28 | *** |
| 29 | *** |
| 30 | *** |
| 31 | *** |
| 32 | *** |
| 33 | *** |
| 34 | ** |
| 35 | *** |
| 36 | *** |
| 37 | *** |
| 38 | *** |
| 39 | ** |
| 40 | ** |
| 41 | ** |
| 42 | ** |
| 43 | ** |
| 44 | ** |
| 45 | ** |
| 46 | *** |
| 47 | *** |
| 48 | ** |
| 49 | ** |
| 50 | ** |
| 51 | ** |
| 52 | ** |
| 53 | ** |
| 54 | ** |
| 55 | ** |
| 56 | *** |
| 57 | ** |
| 58 | ** |
| 59 | ** |
| 60 | ** |
| 61 | ** |
| 62 | *** |
| 63 | ** |
| 64 | *** |
| 65 | ** |
| 66 | ** |
| 67 | ** |
| 68 | ** |
| 69 | *** |
| 70 | *** |
| 71 | ** |
| 72 | ** |
| 73 | *** |
| 74 | *** |
| 75 | *** |
| 76 | ** |
| 77 | *** |
| 78 | ** |
| 79 | ** |
| 80 | ** |
| 81 | ** |
| 82 | *** |
| 83 | *** |
| 84 | ** |
| 85 | ** |
| 86 | *** |
| 87 | ** |
| 88 | ** |
| 89 | ** |
| 90 | * |
| 91 | * |
| 92 | * |
| 93 | * |
| 94 | ** |
| 95 | ** |
| 96 | ** |
| 97 | ** |
| 98 | ** |
| 99 | ** |
| 100 | ** |
| 101 | ** |
| 102 | * |
| 103 | ** |
| 104 | ** |
| 105 | ** |
| 106 | ** |

The invention claimed is:
1. A compound of the formula (I):

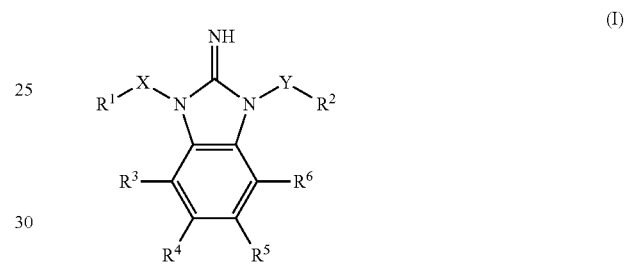

wherein

X is (CH$_2$)$_m$ optionally substituted with one or more substituents selected from the group consisting of methyl and ethyl, when m is 1; or X is (CH$_2$)$_m$ optionally substituted with one or more substituents selected from the group consisting of methyl, ethyl, OH and halo, when m is 2, 3 or 4;

m is an integer from 1 to 4;

R$^1$ is R$^7$, OR$^7$, SR$^7$, NHR$^7$

R$^7$ is H, aryl or heteroaryl optionally substituted with halo, —NO$_2$, —CN, —R$^8$, —OR$^8$, —C(O)OR$^8$, —C(O)R$^8$, —C(O)N(R$^8$)$_2$, —C(O)NHSO$_2$R$^8$, —SOR$^8$, —SO$_2$R$^8$, —SO$_2$N(R$^8$)$_2$, —N(R$^8$)$_2$, —NR$^8$C(O)R$^8$, each R$^8$ is independently H or C$_1$-C$_4$ alkyl;

Y is (CH$_2$)$_n$ n is an integer from 1 to 6;

R$^3$, R$^4$, R$^5$ and R$^6$ are each independently selected from hydrogen, halogen, C$_1$-C$_6$ alkyl, —OR$^{14}$, —C(O)N(R$^{14}$)$_2$, —S(O)R$^{14}$, —S(O)$_2$R$^{14}$, —S(O)$_2$N(R$^{14}$)$_2$, —N(R$^{14}$)$_2$, —NR$^{14}$C(O)R$^{14}$, —C(O)OR$^{14}$, —C(O)R$^{14}$, —SR$^{14}$, NO$_2$ and CN;

R$^{14}$ is hydrogen or C$_1$-C$_6$ alkyl, phenyl or a 5- or 6-membered heteroaryl group, wherein the alkyl, phenyl and heteroaryl groups may optionally be substituted with one or more substituents chosen from halo, CF$_3$, CN, NO$_2$, OCH$_3$, and, for phenyl and heteroaryl groups, C$_1$-C$_4$ alkyl; and R$^2$ is a group R$^{10}$, where R$^{10}$ is a 5- or 6-membered aryl or heteroaryl group substituted by a group R$^{12}$, where R$^{12}$ is a 5- or 6-membered carbocyclic or heterocyclic group, —(C$_1$-C$_4$ alkyl)(C$_5$-C$_6$ carbocyclyl) or —(C$_1$-C$_4$ alkyl)(C$_5$-C$_6$ heterocyclyl) which, in turn is optionally substituted by a group R$^{13}$;

R$^{13}$ is -carbocyclyl, -heterocyclyl, -aryl, -heteroaryl, —C$_1$-C$_6$ alkyl(carbocyclyl), —C$_1$-C$_6$ alkyl(heterocyclyl), -C$_1$-C$_6$ alkyl(aryl) or
—C$_1$-C$_6$ alkyl(heteroaryl), which is optionally substituted with one or more substituents chosen from halo and C$_1$-C$_6$ alkyl, -carbocyclyl,
-heterocyclyl, -aryl, -heteroaryl, any of which may optionally be substituted with one or more substituents chosen from halo, CN, NO$_2$, O(C$_1$-C$_4$ alkyl) and C$_1$-C$_4$ alkyl;
or a tautomer or pharmaceutically acceptable salt thereof.

2. A compound of the formula (I), as claimed in claim 1, wherein R$^{12}$ is a 5- or 6-membered carbocyclic or heterocyclic group which may be substituted by one or more substituents including a group R$^{13}$.

3. A compound of the formula (I), as claimed in claim 1, wherein R$^{12}$ is piperazine, for example 1,4-piperazine optionally substituted with a substituent R$^{13}$ at the 4-position.

4. A compound of the formula (I), as claimed in claim 1, wherein R$^{13}$ is C$_5$-C$_6$ carbocyclyl, C$_5$-C$_6$ aryl, —CH$_2$(C$_5$-C$_6$ carbocyclyl) or —CH$_2$(C$_5$-C$_6$ aryl), any of which may optionally be substituted with one or more substituents chosen from halo and C$_1$-C$_6$ alkyl, -carbocyclyl,
-heterocyclyl, -aryl, -heteroaryl, any of which may optionally be substituted with one or more substituents chosen from halo, CN, NO$_2$, O(C$_1$-C$_4$ alkyl) and C$_1$-C$_4$ alkyl.

5. A compound of the formula (I), as claimed in claim 1, wherein R$^{13}$ is —CH$_2$(C$_5$-C$_6$ carbocyclyl) or —CH$_2$(C$_5$-C$_6$ aryl), either of which may optionally be substituted with one or more halo or methyl groups and/or with a 5- or 6-membered aryl or heteroaryl group which is in turn optionally substituted with halo.

6. A compound of the formula (I), as claimed in claim 1, wherein R$^{13}$ is —CH$_2$(biphenyl) optionally substituted with halo or —CH$_2$(2-phenyl-1,2-cyclohexenyl) optionally substituted with one or two methyl groups and/or with one or more halo substituents.

7. A compound of the formula (I), as claimed in claim 1, wherein Y is CH$_2$.

8. A compound of the formula (I), as claimed in claim 1, wherein:
X is (CH$_2$)$_m$, where m is 1 to 3 and which, when m is 2 or 3, is optionally substituted with OH; and
R$^1$ is OR$^7$ or SR$^7$, where R$^7$ is phenyl optionally substituted with halo, C(O)OR$^8$.

9. A compound as claimed in claim 1 selected from the group consisting of:
1-Benzyl-3-pyridin-2-ylmethyl-1,3-dihydro-benzoimidazol-2-ylideneamine;
1-Benzyl-3-pyridin-3-ylmethyl-1,3-dihydro-benzoimidazol-2-ylideneamine;
1-Benzyl-3-pyridin-4-ylmethyl-1,3-dihydro-benzoimidazol-2-ylideneamine;
1-Benzyl-3-(tetrahydro-pyran-4-ylmethyl)-1,3-dihydro-benzoimidazol-2-ylideneamine;
1-(4-Bromo-benzyl)-3-[3-(4-fluoro-phenoxy)-propyl]-1,3-dihydro-benzoimidazol-2-ylideneamine;
1-(3-Bromo-benzyl)-3-[3-(4-fluoro-phenoxy)-propyl]-1,3-dihydro-benzoimidazol-2-ylideneamine;
1-(4-Bromo-benzyl)-3-(2-phenylsulfanyl-ethyl)-1,3-dihydro-benzoimidazol-2-ylideneamine;
{3-[3-(4-Fluoro-phenoxy)-propyl]-2-imino-2,3-dihydro-benzoimidazol-1-yl}-acetic acid ethyl ester;
1-[3-(4-Chloro-phenoxy)-propyl]-3-pyridin-4-ylmethyl-1,3-dihydro-benzoimidazol-2-ylideneamine;
1-(3-Chloro-benzyl)-3-[3-(4-fluoro-phenoxy)-propyl]-1,3-dihydro-benzoimidazol-2-ylideneamine;
1-(3,4-Dichloro-benzyl)-3-[3-(4-fluoro-phenoxy)-propyl]-1,3-dihydro-benzoimidazol-2-ylideneamine;
1-(4-Bromo-benzyl)-3-[3-(4-chloro-phenoxy)-propyl]-1,3-dihydro-benzoimidazol-2-ylideneamine;
1-(4-Bromo-benzyl)-3-(2,3-dihydro-benzo[1,4]dioxin-2-ylmethyl)-1,3-dihydro-benzoimidazol-2-ylideneamine;
1-(4-Bromo-benzyl)-3-[3-(4-nitro-phenoxy)-propyl]-1,3-dihydro-benzoimidazol-2-ylideneamine;
3-{3-[3-(4-Fluoro-phenoxy)-propyl]-2-imino-2,3-dihydro-benzoimidazol-1-ylmethyl}-benzoic acid methyl ester;
1-(4'-Fluoro-biphenyl-4-ylmethyl)-3-[3-(4-fluoro-phenoxy)-propyl]-1,3-dihydro-benzoimidazol-2-ylideneamine;
1-[4-(4-Biphenyl-2-ylmethyl-piperazin-1-yl)-benzyl]-3-methyl-1,3-dihydro-benzoimidazol-2-ylideneamine;
1-Benzyl-3-[4-(4-biphenyl-2-ylmethyl-piperazin-1-yl)-benzyl]-1,3-dihydro-benzoimidazol-2-ylideneamine;
1-{4-[4-(4-Chloro-benzyl)-piperazin-1-yl]-benzyl}-3-[3-(4-fluoro-phenoxy)-propyl]-1,3-dihydro-benzoimidazol-2-ylideneamine;
1-{4-[4-(2-Chloro-benzyl)-piperazin-1-yl]-benzyl}-3-[3-(4-fluoro-phenoxy)-propyl]-1,3-dihydro-benzoimidazol-2-ylideneamine;
1-{4-[4-(3-Chloro-benzyl)-piperazin-1-yl]-benzyl}-3-[3-(4-fluoro-phenoxy)-propyl]-1,3-dihydro-benzoimidazol-2-ylideneamine;
1-[4-(4-Benzyl-piperazin-1-yl)-benzyl]-3-[3-(4-fluoro-phenoxy)-propyl]-1,3-dihydro-benzoimidazol-2-ylideneamine;
1-(4-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
1-{4-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;
1-[4-(4-Biphenyl-2-ylmethyl-piperazin-1-O-benzyl]-3-[3-(4-fluoro-phenoxy)-propyl]-1,3-dihydro-benzoimidazol-2-ylideneamine;
1-[3-(4-Biphenyl-2-ylmethyl-piperazin-1-O-benzyl]-3-[3-(4-fluoro-phenoxy)-propyl]-1,3-dihydro-benzoimidazol-2-ylideneamine;
1-{3-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;
1-[4-(4-Biphenyl-2-ylmethyl-piperazin-1-O-benzyl]-3-(3-phenoxy-propyl)-1,3-dihydro-benzoimidazol-2-ylideneamine;
1-[3-(4-Biphenyl-2-ylmethyl-piperazin-1-O-benzyl]-3-(3-phenoxy-propyl)-1,3-dihydro-benzoimidazol-2-ylideneamine;
1-{4-[4-(4'-Chloro-biphenyl-2-ylmethyl)-piperazin-1-yl]-benzyl}-3-(3-phenoxy-propyl)-1,3-dihydro-benzoimidazol-2-ylideneamine;
1-(3-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;
1-(4-{4-[2-(4-Chloro-phenyl)-5,5-dimethyl-cyclohex-1-enylmethyl]-piperazin-1-yl}-benzyl)-3-(3-phenoxy-propyl)-1,3-dihydro-benzoimidazol-2-ylideneamine;
1-{4-[4-(4'-Chloro-biphenyl-2-ylmethyl)-piperazin-1-yl]-benzyl}-3-(2-phenylsulfanyl-ethyl)-1,3-dihydro-benzoimidazol-2-ylideneamine;

1-(2-Chloro-thiazol-4-ylmethyl)-3-[3-(4-fluoro-phenoxy)-propyl]-1,3-dihydro-benzoimidazol-2-ylideneamine;
1-[2-(4-Biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine;
1-{2-[4-(4'-Chloro-biphenyl-2-ylmethyl)-piperazin-1-yl]-thiazol-4-ylmethyl}-3-[3-(4-fluoro-phenoxy)-propyl]-1,3-dihydro-benzoimidazol-2-ylideneamine;
1-(2-{4-[2-(4-Chloro-phenyl)-5,5-dimethyl-cyclohex-1-enylmethyl]-piperazin-1-yl}-thiazol-4-ylmethyl)-3-[3-(4-fluoro-phenoxy)-propyl]-1,3-dihydro-benzoimidazol-2-ylideneamine;
1-[2-(4-Biphenyl-2-ylmethyl-piperazin-1-yl)-benzyl]-3-[3-(4-fluoro-phenoxy)-propyl]-1,3-dihydro-benzoimidazol-2-ylideneamine;
1-{4-[4-(4-Chloro-benzyl)-piperazin-1-ylmethyl]-benzyl}-3-[3-(4-fluoro-phenoxy)-propyl]-1,3-dihydro-benzoimidazol-2-ylideneamine;
1-[3-(4-Fluoro-phenoxy)-propyl]-3-[4-(4-phenyl-piperazin-1-ylmethyl)-benzyl]-1,3-dihydro-benzoimidazol-2-ylideneamine;
1-{4-[4-(3-Chloro-phenyl)-piperazin-1-ylmethyl]-benzyl}-3-[3-(4-fluoro-phenoxy)-propyl]-1,3-dihydro-benzoimidazol-2-ylideneamine;
1-{4-[4-(4-Chloro-phenyl)-piperazin-1-ylmethyl]-benzyl}-3-[3-(4-fluoro-phenoxy)-propyl]-1,3-dihydro-benzoimidazol-2-ylideneamine;
N-(2-Chloro-phenyl)-2-(4-{3-[3-(4-fluoro-phenoxy)-propyl]-2-imino-2,3-dihydro-benzoimidazol-1-ylmethyl}-benzylamino)-acetamide;
1-{4-[4-(2-Chloro-phenyl)-piperazin-1-ylmethyl]-benzyl}-3-[3-(4-fluoro-phenoxy)-propyl]-1,3-dihydro-benzoimidazol-2-ylideneamine;
N-(4-Chloro-phenyl)-2-(4-{3-[3-(4-fluoro-phenoxy)-propyl]-2-imino-2,3-dihydro-benzoimidazol-1-ylmethyl}-benzylamino)-acetamide;
1-[4-(4-Benzyl-piperazin-1-ylmethyl)-benzyl]-3-[3-(4-fluoro-phenoxy)-propyl]-1,3-dihydro-benzoimidazol-2-ylideneamine;
1-{4-[4-(3-Chloro-benzyl)-piperazin-1-ylmethyl]-benzyl}-3-[3-(4-fluoro-phenoxy)-propyl]-1,3-dihydro-benzoimidazol-2-ylideneamine;
1-{4-[4-(2-Chloro-benzyl)-piperazin-1-ylmethyl]-benzyl}-3-[3-(4-fluoro-phenoxy)-propyl]-1,3-dihydro-benzoimidazol-2-ylideneamine;
1-[4-(4-Biphenyl-2-ylmethyl-piperazin-1-ylmethyl)-benzyl]-3-[3-(4-fluoro-phenoxy)-propyl]-1,3-dihydro-benzoimidazol-2-ylideneamine;
N-(3-Chloro-phenyl)-2-(4-{3-[3-(4-fluoro-phenoxy)-propyl]-2-imino-2,3-dihydro-benzoimidazol-1-ylmethyl}-benzylamino)-acetamide;
2-(4-{3-[3-(4-Fluoro-phenoxy)-propyl]-2-imino-2,3-dihydro-benzoimidazol-1-ylmethyl}-benzylamino)-N-phenyl-acetamide;
1-(6-Chloro-pyridin-3-ylmethyl)-3-[3-(4-fluoro-phenoxy)-propyl]-1,3-dihydro-benzoimidazol-2-ylideneamine;
1-[6-(4-Benzyl-piperazin-1-yl)-pyridin-3-ylmethyl]-3-[3-(4-fluoro-phenoxy)-propyl]-1,3-dihydro-benzoimidazol-2-ylideneamine;
1-{6-[4-(3-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
1-{6-[4-(4-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
1-[6-(4-Biphenyl-2-ylmethyl-piperazin-1-yl)-pyridin-3-ylmethyl]-3-[3-(4-fluoro-phenoxy)-propyl]-1,3-dihydro-benzoimidazol-2-ylideneamine;
1-{6-[4-(2-Chloro-benzyl)-piperazin-1-yl]-pyridin-3-ylmethyl}-3-[3-(4-fluoro-phenoxy)-propyl]-1,3-dihydro-benzoimidazol-2-ylideneamine;
3-(4-Bromo-benzyl)-1-[3-(4-fluoro-phenoxy)-propyl]-5-methyl-1,3-dihydro-benzoimidazol-2-ylideneamine;
3-(4-Bromo-benzyl)-5-fluoro-1-[3-(4-fluoro-phenoxy)-propyl]-1,3-dihydro-benzoimidazol-2-ylideneamine;
1-(4-Bromo-benzyl)-3-[3-(4-fluoro-phenoxy)-propyl]-5-trifluoromethyl-1,3-dihydro-benzoimidazol-2-ylideneamine;
1-(4-Bromo-benzyl)-5-fluoro-3-[3-(4-fluoro-phenoxy)-propyl]-1,3-dihydro-benzoimidazol-2-ylideneamine;
3-[4-(4-Biphenyl-2-ylmethyl-piperazin-1-yl)-benzyl]-1-[3-(4-fluoro-phenoxy)-propyl]-5-methyl-1,3-dihydro-benzoimidazol-2-ylideneamine;
3-[4-(4-Biphenyl-2-ylmethyl-piperazin-1-yl)-benzyl]-5-fluoro-1-[3-(4-fluoro-phenoxy)-propyl]-1,3-dihydro-benzoimidazol-2-ylideneamine;
3-(4-{4-[2-(4-Chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine;
3-{3-[3-(4-Bromo-benzyl)-2-imino-2,3-dihydro-benzoimidazol-1-yl]-propoxy}-benzoic acid ethyl ester;
4-{3-[3-(4-Bromo-benzyl)-2-imino-2,3-dihydro-benzoimidazol-1-yl]-propoxy}-benzoic acid methyl ester;
4-{3-[3-(3-Bromo-benzyl)-2-imino-2,3-dihydro-benzoimidazol-1-yl]-propoxy}-benzoic acid methyl ester;
3-{3-[3-(3-Bromo-benzyl)-2-imino-2,3-dihydro-benzoimidazol-1-yl]-propoxy}-benzoic acid ethyl ester;
3-(3-{3-[4-(4-Biphenyl-2-ylmethyl-piperazin-1-yl)-benzyl]-2-imino-2,3-dihydro-benzoimidazol-1-yl}-propoxy)-benzoic acid ethyl ester;
3-(3-{3-[4-(4-Biphenyl-2-ylmethyl-piperazin-1-yl)-benzyl]-2-imino-2,3-dihydro-benzoimidazol-1-yl}-propoxy)-benzoic acid;
3-[3-(3-Benzyl-2-imino-2,3-dihydro-benzoimidazol-1-yl)-propoxy]-benzoic acid ethyl ester;
3-{3-[3-(4-Fluoro-phenoxy)-propyl]-2-imino-2,3-dihydro-benzoimidazol-1-ylmethyl}-benzoic acid;
3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid ethyl ester;
3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid;
3-{3-[3-(3-{4-[2-(4-Chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid;
1-[3-(3-Bromo-benzyl)-2-imino-2,3-dihydro-benzoimidazol-1-yl]-3-(4-fluoro-phenoxy)-propan-2-ol;
1-[3-(4-Bromo-benzyl)-2-imino-2,3-dihydro-benzoimidazol-1-yl]-3-(4-fluoro-phenoxy)-propan-2-ol;
1-(3-Benzyl-2-imino-2,3-dihydro-benzoimidazol-1-yl)-3-phenoxy-propan-2-ol;
1-{3-[3-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;
3-{3-[3-(3-Bromo-benzyl)-2-imino-2,3-dihydro-benzoimidazol-1-yl]-propoxy}-benzoic acid;

3-{3-[3-(4-Bromo-benzyl)-2-imino-2,3-dihydro-benzoimidazol-1-yl]-propoxy}-benzoic acid; and N-(3-{3-[3-(3-Bromo-benzyl)-2-imino-2,3-dihydro-benzoimidazol-1-yl]-propoxy}-benzoyl)-methanesulfonamide;

or a tautomer, or pharmaceutically acceptable salt thereof.

10. A pharmaceutical composition comprising a compound according to claim 1 and a pharmaceutically acceptable carrier.

\* \* \* \* \*

UNITED STATES PATENT AND TRADEMARK OFFICE
CERTIFICATE OF CORRECTION

Page 1 of 1

PATENT NO. : 8,759,520 B2
APPLICATION NO. : 13/132429
DATED : June 24, 2014
INVENTOR(S) : East et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Twenty-eighth Day of July, 2015

Michelle K. Lee
*Director of the United States Patent and Trademark Office*